(12) United States Patent
Brooks et al.

(10) Patent No.: US 7,053,041 B1
(45) Date of Patent: May 30, 2006

(54) METHODS AND COMPOSITIONS USEFUL FOR INHIBITION OF $\alpha_v\beta_5$ MEDIATED ANGIOGENESIS

(75) Inventors: Peter C. Brooks, West Harrison, NY (US); David A. Cheresh, Encinitas, CA (US); Martin Friedlander, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/194,552

(22) PCT Filed: May 30, 1997

(86) PCT No.: PCT/US97/09099

§ 371 (c)(1),
(2), (4) Date: Mar. 23, 1999

(87) PCT Pub. No.: WO97/45447

PCT Pub. Date: Dec. 4, 1997

Related U.S. Application Data

(60) Provisional application No. 60/018,773, filed on May 31, 1996, provisional application No. 60/015,869, filed on May 31, 1996.

(51) Int. Cl.
| | |
|---|---|
| *A01N 61/00* | (2006.01) |
| *A01N 37/18* | (2006.01) |
| *A61K 31/00* | (2006.01) |
| *A61K 38/00* | (2006.01) |

(52) U.S. Cl. .................... 514/2; 514/1; 514/4; 514/8; 514/9; 514/11; 514/14; 530/300; 530/317; 530/321; 530/326; 530/385; 530/386; 530/387.1; 436/64; 436/86; 424/184.1; 424/185.1

(58) Field of Classification Search ............ 530/321, 530/326, 385, 386, 387.1, 300, 317, 350; 514/9, 11, 14; 424/184.1, 185.1; 436/64, 436/86

See application file for complete search history.

(56) References Cited

U.S. PATENT DOCUMENTS

| | | | |
|---|---|---|---|
| 4,517,686 A | 5/1985 | Ruoslahti | |
| 4,578,079 A | 3/1986 | Ruoslahti | |
| 4,589,881 A | 5/1986 | Pierschbacher | |
| 4,614,517 A | 9/1986 | Ruoslahti | |
| 4,661,111 A | 4/1987 | Ruoslahti | |
| 4,683,291 A | 7/1987 | Zimmerman . | |
| 4,792,525 A | 12/1988 | Ruoslahti | |
| 4,879,237 A | 11/1989 | Rudslahti | |
| 4,988,621 A | 1/1991 | Ruoslahti | |
| 5,041,380 A | 8/1991 | Ruoslahti | |
| 5,061,693 A | 10/1991 | Nutt | |
| 5,135,919 A | 8/1992 | Folkman et al. | |
| 5,567,693 A * | 10/1996 | Backer et al. | |
| 5,575,815 A | 11/1996 | Slepian et al. | |
| 5,849,692 A | 12/1998 | Jonczyk et al. | |
| 5,866,540 A | 2/1999 | Jonczyk et al. | |
| 5,968,902 A | 10/1999 | Scarborough et al. | |
| 5,981,478 A | 11/1999 | Ruoslahti et al. | |
| 6,001,961 A | 12/1999 | Jonczyk et al. | |
| 6,204,280 B1 | 3/2001 | Gante et al. | |

FOREIGN PATENT DOCUMENTS

| | | |
|---|---|---|
| EP | 0 578 083 A2 | 6/1993 |
| EP | 0 770 622 A | 5/1997 |
| WO | 89/06536 | 7/1989 |
| WO | 95/14714 | 6/1995 |
| WO | 95/28426 | 10/1995 |
| WO | 97/14716 | 4/1997 |

OTHER PUBLICATIONS

Friedlander et al. Definition of Two Angiogenic Pathways by Distinct Alpha v Integrins. Science 270:1500-1502.*
Collier et al. H-ras Oncogene-transformed Human bronchial epithelial cells (TBE-1) secrete a single metalloprotease capable of degrading basement membrane collagen. The Journal of Biological Chemistry. 263(14):6579-6587.*
Chen et al. Isolation and Characterization of a 70-kDa metalloprotease (gelatinase) that is elevated in rous sarcoma virus-transformed chicken embryo fibroblasts. Journal of Biological Chemistry. 266(8):5113-5121.*
Amino acid database; Accession #Q90611.*
Amino acid database, Accession #A28153.*
Lazar et al. Transforming growth factor alpha: mutation of aspartic acid 47 and leucine 48 results in different biological activities. Molecular and Cellular Biology 8(3):1247-1252, Mar. 1988.*
Hammes, et al., Subcutaneous injection of a cyclic peptide antagonist of vitronectin receptor-type integrins inhibits retinal neovascularization, 1996, *Nature Med.*, 2(5):529-533.
Brooks, et al., Integrin $\alpha v\beta 3$ antagonist promote tumor regression by inducing apoptosis of angiogenic blood vessels, 1994, *Cell*, 79:1157-1164.
Clark, et al, Transient functional expression of $\alpha v\beta 3$ on vascular cells during wound repair, 1996, *Am. J Pathol.*, 148:1407-1421.
Bauer, et al., In vitro model of angiogenesis using a human endothelium-derived permanent cell line: contributions of induced gene expression, G-proteins and integrins, 1992, *J. Cell. Physiol.*, 153:437-449.

(Continued)

Primary Examiner—Alana M. Harris
(74) Attorney, Agent, or Firm—Thomas Fitting; Michael J. McCarthy

(57) ABSTRACT

The present invention describes methods for inhibiting angiogenesis in tissues using vitronectin $\alpha_v\beta_5$ antagonists. The $\alpha_v\beta_5$-mediated angiogenesis is correlated with exposure to cytokines including vascular endothelial growth factor, transforming growth factor-$\alpha$ and epidermal growth factor. Inhibition of $\alpha_v\beta_5$-mediated angiogenesis is particularly preferred in vascular endothelial ocular neovascular diseases, in tumor growth and in inflammatory conditions, using therapeutic compositions containing $\alpha_v\beta_5$ antagonists.

42 Claims, 26 Drawing Sheets

OTHER PUBLICATIONS

Ingber, Extracellular matrix as a solid state regulator of angiogenesis: identification of new targets for anti-cancer therapy, 1992, *Seminars in Cancer Biology*, 3:57-63.

Hardan, et al., Inhibition of metastatic cell colonization in murine lungs and tumor-induced morbidity by non-peptidic Arg-Gly-Asp mimetics, 1993, *Int. J. Cancer*, 55:1023-1028.

Haynes, Integrins: versatility, modulation, and signaling in cell adhesion, 1992, *Cell*, 69:11-25.

Lehmann, et al., A monoclonal antibody inhibits adhesion to fibronectin and vitronectin of a colon carcinoma cell line and recognizes the integrins αvβ3, αvβ5 and αvβ6, 1994, *Cancer Res.*, 54:2102-2107.

Pierschbacher, et al., Influence of stereochemistry of the sequence Arg-Gly-Asp-Xaa on binding specificity in cell adhesion, 1987, *J. Biol. Chem.*, 262:17294-17296.

Folkman, et al., Angiogenesis, 1992, *J. Biol. Chem.*, 267:10931-10934.

Teicher, et al., Potentiation of cytotoxic cancer therapies by TNP-470 alone and with other anti-angiogenic agents, 1994, *Intl. J. Cancer*, 57:920-925.

Drake, et al., A antago nist of integrin αvβ3 prevent maturation of blood vessels during embryonic neovascularization, 1995, *J. Cell Sci.*, 108:2655-2661.

Folkman, et al., Inhibition of angiogenesis, 1992, *Cancer Bio.*, 3:89-96.

Aumailley, et al., Arg-Gly-Asp constrained within cyclic pentapeptides: strong and selective inhibitors of cell adhesion to vitronectin and laminin-fragment P1, 1991, *FEBS*, 291(1):50-54.

Choi, et al., Inhibition of neointimal hyperplasia by blocking αvβ3 integrin with a small peptide antagonist GpenGRGDSPCA, 1994, *J. Vasc. Surg.*, 19:125-134.

Matsuno, et al., Inhibition of integrin function by a cyclic RGD-containing peptide prevents neointima formation, 1994, *Circulation*, 90(5):2203-2205.

Timar, et al., The antimetabolite tiazofurin (TR) inhibits glycoconjugate biosynthesis and invasiveness of tumour cells, 1996, *Eur. J. Cancer*, 32A(1):152-159.

Aimes, et al., Cloning of a 72 kDa matrix metalloproteinase (gelatinase) from chicken fibroblasts using gene family PCR: expression of the gelatinase increases upo n malignant transformation, 1994, Biochem J., 300:729-736.

Friedlander, et al., Definition of two angiogenic pathways by distint αv integrins, 1995, *Science*, 270:1500-1502.

Pfaff, et al., Comparison of disintegrins with limited variation in the RGD loop in their binding to purified integrins αIIbβ3, αvβ3 and α5β1 and in cell adhesion inhibition, 1994, *Cell Adhes. Commun.*, 2(6):491-501.

Smith, et al., Interaction of integrins αvβ3 and glycoprotein IIb-IIIa with fibrinogen, 1990, *J. Biol. Chem.*, 265:12267-12271.

Mueller, et al., Pre-clinical therapy of human melanoma with morpholino-doxorubicin conjugated to a monoclonal antibody directed against an integrin on melanoma cells, *Antibosy, Immunoconjugates, and Radiopharmaceuticals*, 1991, 4(2):99-106.

Ossowski, et al., Experimental model for quantitative study of metastasis, 1980, *Cancer Res.*, 40:2300-2309.

Klein, et al., Basic fibroblast growth factor modulates integrin expression in microvascular endothelial cells, 1993, *Mol. Biol. Cell*, 4:973-982.

Brooks, et al., "Subtractive Immunization Yields Monoclonal Antibodies that Specificaly Inhibit Metastasis", J. Cell Biology, 122: 1351-1359 (1993).

Brooks et al., Requirement of Vascular Integrin Alpha v Beta 3 for Angiogenesis *Science*, 264: 569-571 (1994).

Brown, et al., "Expression of Vascular Permeability Factor (Vascular Endothelial Growth Factor) and its Receptors in Breast Cancer", Human Path., 26:86 (1995).

Cheng, et al., "Human Microvascular Endothelial Cells express Integrin-Related Complexes that Mediate Adhesion to the Extracellular Matrix", *J. Cell Physiol.*, 139: 275-286 (1989).

Cheresh, David A., "Human endothelial cells synthesize and express an Arg-Gly-Asp-directed adhesion receptor involved in Attachment to fibrinogen and von Willebnrand factor", Proc. Natl. Acad. Sci., USA, 84: 6471-6475 (1987).

Davis, et al., "Identification of Endothelial Cell Vascular Formation",J. Cellular Biochemistry, 51: 206-218 (1993).

Horton, Michael, "Current Ststus Review Vitronectin receptor: tissue specific expression or adaptation to culture?", Int. J. Exp Path., 71: 741-759 (1990).

Janat, et al., "regulation of Vascular Smooth Muscle Cell Integrin Expression by Transforming Growth Factor beta 1 By Platelet-Derived Growth Factor-BB", J. Cellular Physiol., 151: 588-595 (1992).

Nicosia, et al., "Rapid Communication: Inhibition of Angiogenesis in vitro by Arg-Gly-Asp-Containing Synthetic Peptide", Am. J. Path., 138: 829-833 (1991).

Pasqualini, et al., "A study of the structure, function and distribution of beta 5 integrins using novel anti-beta 5 moniclonal antibodies", J. Cell Science, 105; 101-111 (1993).

Pfaff, et al., "Selective Recognition of Cyclic RGD Peptides of NMR Defined Conformation by AIIbB3, avB3, and Integrins", J. Biol. Chem., 269: 20233-20238 (1994).

Wayner, et al., "Integrins avB3 and avB5 Contribute to Cell Attachment to Vitronectin but Differentially Distribute on the Cell Surface", Journ. od Cell Biol., 113; 919-929 (1991).

\* cited by examiner

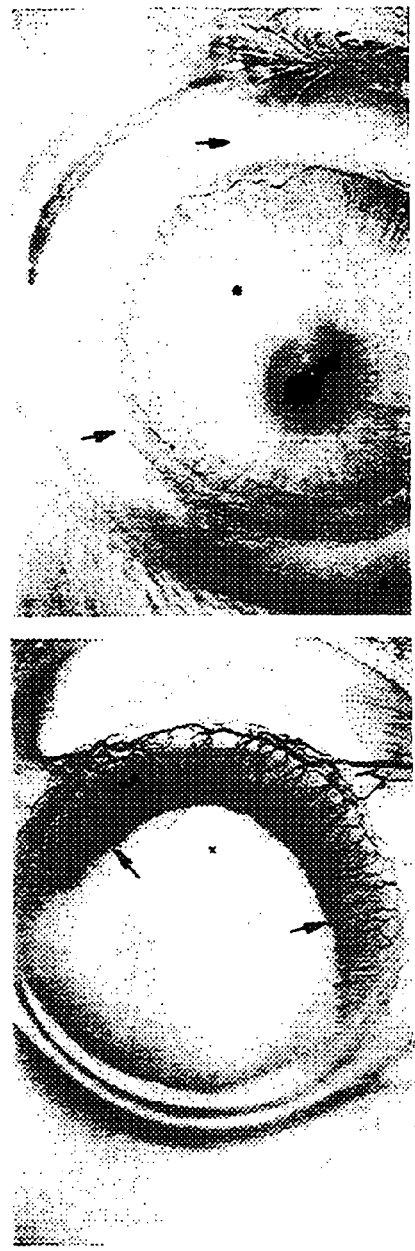

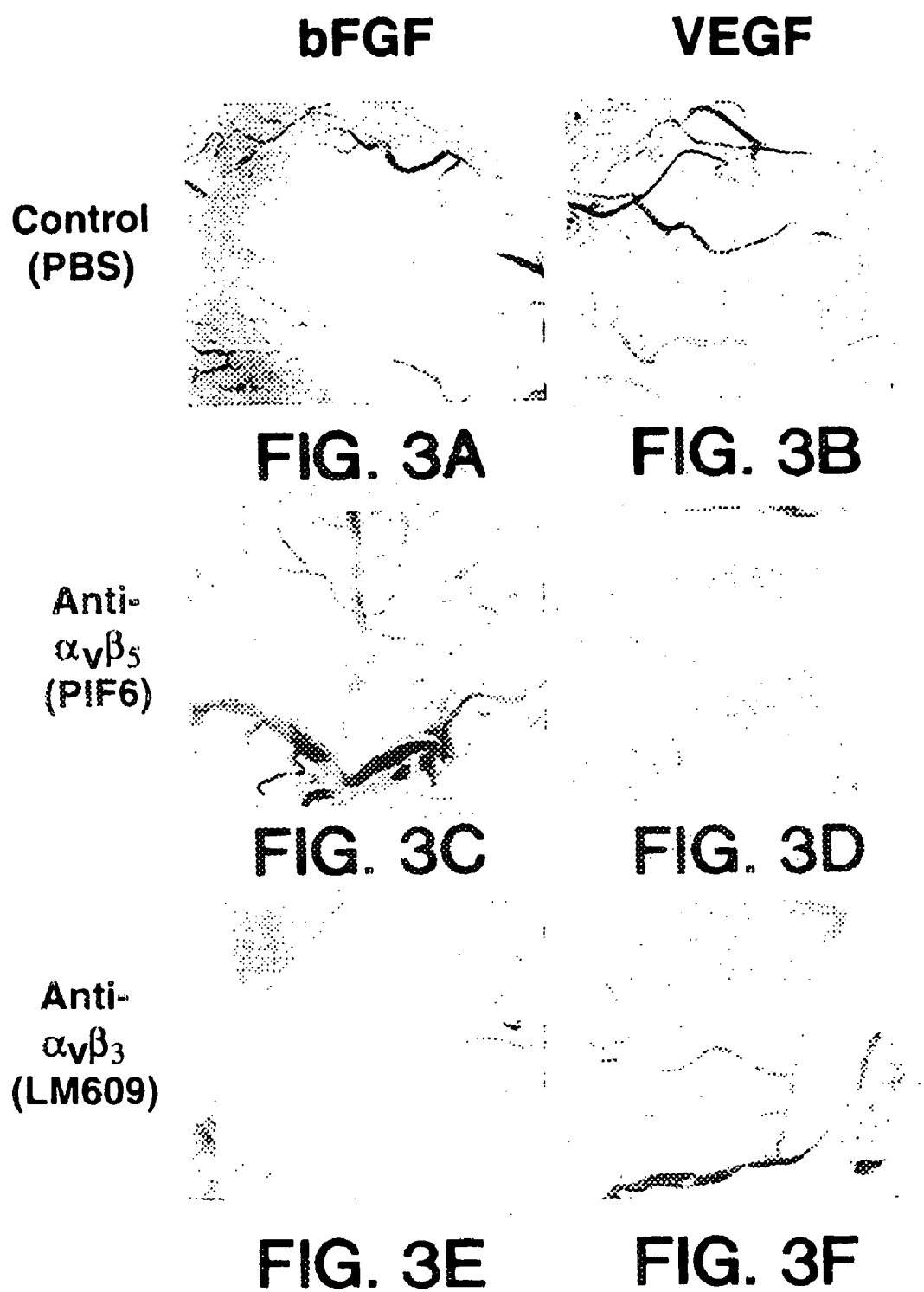

bFGF VEGF

No Peptide

Cyclic Peptide (RGDfV)

Cyclic Peptide (RADfV)

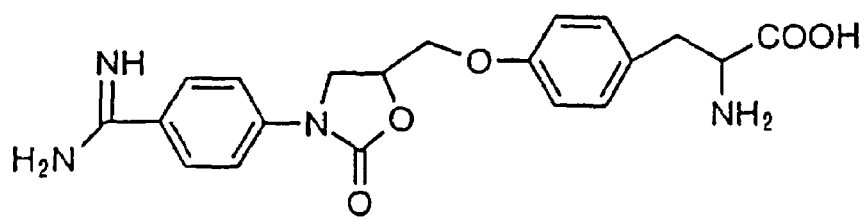
COMPOUND 15
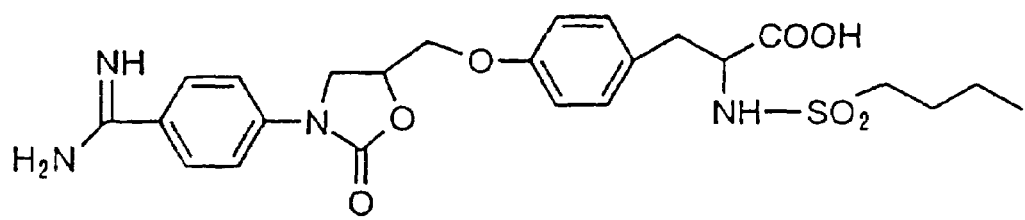
COMPOUND 16
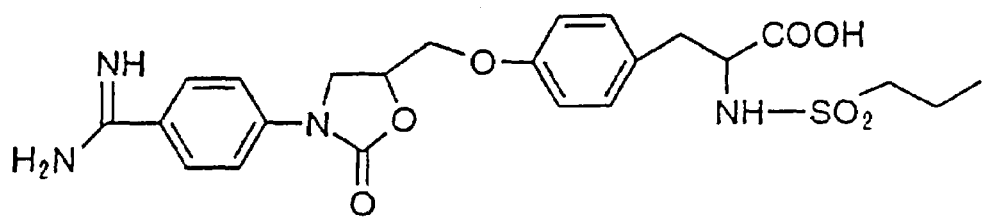
COMPOUND 17
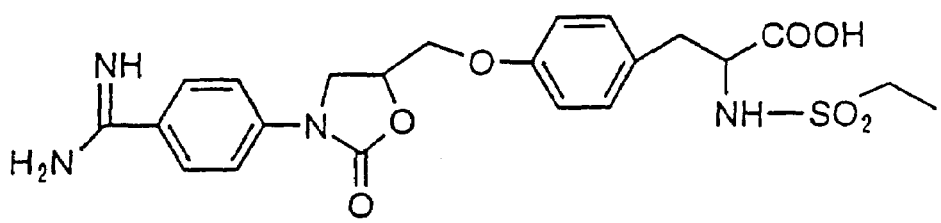
COMPOUND 18
FIG. 14

```
TCAATTACTGGACCAGTCAGGTACTGGCACCCAAACATTAAGTACCAGTACTGTACACATCTGATAATTTAAAAGTGTTTGCCTCCTCAACATACAAAAG  +2091
ATGTTTACGTATCTATTCTGGTACAATTTTCAGTTTGTGCTAGTCATGAACATGCTAGTAGCAGAACACGCAGGTTCTTATTCCCCTGGTGCTTG       +2191
AAGAAGCATTGAAATCATTGGAGACTGGACCAGAGACCCCTGTGTTAAATCCATCCAAATAGCCTCAAGTAGATGAAGTACCAGCAGTGCACTTGATTTTT +2291
TTTTAATTTTTTTTTAAATACAACACTCTTTGTTGTTAATGTTTGTGTTAATGATAGATAGACCCTCTTGCGAGTTTGATCATTACTGCCATTTATTACA  +2391
TAATGATACAAAGACTGTCAAAGGCACAGTTGCCACGGGACATCATGGCAAGAAACATGGCAAGAAACTGTATTAAAGTATTGTT                 +2491
TTAAAGTACTTTCTATTTTTAAAACCTTAGTCACAGAAGTCAACTTAGCAATTTGCTTCCTGCACTTGTTTATTTCTGTTCTTTATAATTGAGTTTGTT   +2591
GATGTTTTAAATCAATGTATTATACAGAAGGTGTTCCTTTCACATATGATGGAATGTTTCTCATTAAAAAAAAAAAGGTTAAAAAAATCCAGAAAACAAT  +2691
CTTTCTGCTTAGGCAACATGCCAATGCTACAAATTAAATTACACTGTCAAAAAAAAAAAAACGGTTAAC                                 +2791
GTCCCAAACATGAAATGCCAATGCTACAAATTAAATTACACTGTCAAAAAAAAAAAAACGGTTAAC                                    +2864
```

FIG. 15D

| | |
|---|---|
| APSPIIKFPGDVAPKTDKELAVQYLNTFYG | 30 |
| CPKESCNLFVLKDTLKKMQKFFGLPQTGDL | 60 |
| DQNTIETMRKPRCGNPDVANYNFFPRKPKW | 90 |
| DKNQITYRIIGYTPDLDPETVDDAFARAFQ | 120 |
| VWSDVTPLRFSRIHDGEADIMINFGRWEHG | 150 |
| DGYPFDGKDGLLAHAFAPGTGVGGDSHFDD | 180 |
| DELWTLGEGQVVRVKYGNADGEYCKFPFLF | 210 |
| NGKEYNSCTDTGRSDGFLWCSTTYNFEKDG | 240 |
| KYGFCPHEALFTMGGNAEGQPCKFPFRFQG | 270 |
| TSYDSCTTEGRTDGYRWCGTTEDYDRDKKY | 300 |
| GFCPETAMSTVGGNSEGAPCVFPFTFLGNK | 330 |
| YESCTSAGRSDGKMWCATTANYDDDRKWGF | 360 |
| CPDQGYSLFLVAAHEFGHAMGLEHSQDPGA | 390 |
| LMAPIYTYTKNFRLSQDDIKGIQELYGASP | 420 |
| DIDLGTGPTPTLGPVTPEICKQDIVFDGIA | 450 |
| QIRGEIFFFKDRFIWRTVTPRDKPMGPLLV | 480 |
| ATFWPELPEKIDAVYEAPQEEKAVFFAGNE | 510 |
| YWIYSASTLERGYPKPLTSLGLPPDVQRVD | 540 |
| AAFNWSKNKKTYIFAGDKFWRYNEVKKKMD | 570 |
| PGFPKLIADAWNAIPDNLDAVVDLQGGGHS | 600 |
| YFFKGAYYLKLENQSLKSVKFGSIKSDWLG | 630 |
| C | 631 |

FIG. 16

METHODS AND COMPOSITIONS USEFUL FOR INHIBITION OF $\alpha_v\beta_5$ MEDIATED ANGIOGENESIS

CROSS-REFERENCE TO RELATED APPLICATIONS

This application claims priority to International Application PCT/US97/09099, filed May 30, 1997, Provisional Application Ser. No. 60/018,773, filed May 31, 1996, Provisional Application Ser. No. 60/015,869, filed May 31, 1996, which is a CIP of International Application PCT/US96/13194, filed Aug. 13, 1996, now abandoned, and U.S. application Ser. No. 08/514,799, filed Aug. 14, 1995, now abandoned.

This invention was made with government support under Contract Nos. CA50826, CA45726, HL54444, T32 AIO7244-11 and F32 CA72192 by the National Institutes of Health. The government has certain rights in the invention.

TECHNICAL FIELD

The present invention relates generally to the field of medicine, and relates specifically to methods and compositions for inhibiting $\alpha_v\beta_5$-mediated angiogenesis of tissues using antagonists of the vitronectin receptor $\alpha_v\beta_5$.

BACKGROUND

Integrins are a class of cellular receptors known to bind extracellular matrix proteins, and therefore mediate cell-cell and cell-extracellular matrix interactions, referred generally to as cell adhesion events. However, although many integrins and their respective ligands are described in the literature, the biological function of many of the integrins remains elusive. The integrin receptors constitute a family of proteins with shared structural characteristics of noncovalent heterodimeric glycoprotein complexes formed of $\alpha$ and $\beta$ subunits.

The vitronectin receptor, named for its original characteristic of preferential binding to vitronectin, is now known to refer to three different integrins, designed $\alpha_v\beta_1$, $\alpha_v\beta_3$ and $\alpha_v\beta_5$. Horton, *Int. J. Exp. Pathol.*, 71:741–759 (1990). $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The specific cell adhesion roles these three integrins play in the many cellular interactions in tissues are still under investigation. However, it is clear that there are different integrins with different biological functions as well as different integrins and subunits having shared biological specificities.

One important recognition site in a ligand for many integrins is the arginine-glycine-aspartic acid (RGD) tripeptide sequence. RGD is found in all of the ligands identified above for the vitronectin receptor integrins. This RGD recognition site can be mimicked by polypeptides ("peptides") that contain the RGD sequence, and such RGD peptides are known inhibitors of integrin function. It is important to note, however, that depending upon the sequence and structure of the RGD peptide, the specificity of the inhibition can be altered to target specific integrins.

For discussions of the RGD recognition site, see Pierschbacher et al., *Nature*, 309:30–33 (1984), and Pierschbacher et al., *Proc. Natl. Acad. Sci. USA*, 81:5985–5988 (1984). Various RGD polypeptides of varying integrin specificity have also been described by Grant et al., *Cell*, 58:933–943 (1989), Cheresh, et al., *Cell*, 58:945–953 (1989), Aumailley et al., *FEBS Letts.*, 291:50–54 (1991), and Pfaff et al., *J. Biol. Chem.*, 269:20233–20238 (1994), and in U.S. Pat. Nos. 4,517,686, 4,578,079, 4,589,881, 4,614,517, 4,661,111, 4,792,525, 4,683,291, 4,879,237, 4,988,621, 5,041,380 and 5,061,693.

Angiogenesis, also referred to as neovascularization, is a process of tissue vascularization that involves the growth of new developing blood vessels into a tissue. The process is mediated by the infiltration of endothelial cells and smooth muscle cells. The process is believed to proceed in any one of three ways: 1) The vessels can sprout from pre-existing vessels; 2) De novo development of vessels can arise from precursor cells (vasculogenesis); or 3) Existing small vessels can enlarge in diameter. Blood et al., *Bioch. Biophys. Acta*, 1032:89–118 (1990). Vascular endothelial cells are known to contain at least five RGD-dependent integrins, including the vitronectin receptor ($\alpha_v\beta_3$ or $\alpha_v\beta_5$), the collagen Types I and IV receptor ($\alpha_1\beta_1$), the laminin receptor ($\alpha_2\beta_1$), the fibronectin/laminin/collagen receptor ($\alpha_3\beta_1$) and the fibronectin receptor ($\alpha_5\beta_1$). Davis et al., *J. Cell. Biochem.*, 51:206–218 (1993). The smooth muscle cell is known to contain at least six RGD-dependent integrins, including $\alpha_5\beta_1$, $\alpha_v\beta_3$ and $\alpha_v\beta_5$.

Angiogenesis is an important process in neonatal growth, but is also important in wound healing and in the pathogenesis of a large variety of clinically important diseases including tissue inflammation, arthritis, psoriasis, cancer, diabetic retinopathy, macular degeneration and other neovascular eye diseases. These clinical entities associated with angiogenesis are referred to as angiogenic diseases. Folkman et al., *Science*, 235:442–447 (1987). Angiogenesis is generally absent in adult or mature tissues, although it does occur in wound healing and in the corpus luteum growth cycle. See, for example, Moses et al., *Science*, 248:1408–1410 (1990).

Inhibition of cell adhesion in vitro using monoclonal antibodies immunospecific for various integrin $\alpha$ or $\beta$ subunits have implicated the vitronectin receptor $\alpha_v\beta_3$ in cell adhesion of a variety of cell types including microvascular endothelial cells. Davis et al., *J. Cell. Biol.*, 51:206–218 (1993). In addition, Nicosia et al., *Am. J. Pathol.*, 138:829–833 (1991), described the use of the RGD peptide, GRGDS, to inhibit the in vitro formation of "microvessels" from rat aorta cultured in collagen gel.

However, the inhibition of formation of "microvessels" in vitro in collagen gel cultures is not a model for inhibition of angiogenesis in a tissue because it is not shown that the microvessel structures are the same as capillary sprouts or that the formation of the microvessel in collagen gel culture is the same as new-vascular growth into an intact tissue, such as arthritic tissue, tumor tissue or disease tissue where inhibition of angiogenesis is desirable.

The role of $\alpha_v\beta_3$ in angiogenesis was recently confirmed. See, Brooks, et al. *Science*, 264:569–571 (1994). The integrin was shown to be expressed on blood vessels in human wound granulation tissue but not in normal skin. Monoclonal antibodies against the $\alpha_v\beta_1$ receptor inhibited angiogenesis induced by the growth factors (cytokines) basic fibroblast growth factor (bFGF) and tumor necrosis factor-$\alpha$ (TNF-$\alpha$), as well as by melanoma fragments. However, the antagonists only inhibited new and not preexisting vessels. In addition, specific linear and cyclic RGD-containing peptides were also shown to inhibit neovascularization.

It has been proposed that inhibition of angiogenesis would be a useful therapy for restricting tumor growth. Inhibition of angiogenesis has been proposed by (1) inhibition of release of "angiogenic molecules" such as bFGF (basic fibroblast growth factor), (2) neutralization of angiogenic molecules, such as by use of anti-bFGF antibodies, and (3) inhibition of endothelial cell response to angiogenic stimuli. This latter strategy has received attention, and Folkman et al., *Cancer Biology*, 3:89–96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood et al., *Bioch. Biophys. Acta.*, 1032: 89–118 (1990), Moses et al., *Science*, 248:1408–1410 (1990), Ingber et al., *Lab. Invest.*, 59:44–51 (1988), and U.S. Pat. Nos. 5,092,885, 5,112,946, 5,192,744, and 5,202,352.

However, the role of the integrin $\alpha_v\beta_5$ in angiogenesis has neither been suggested or identified until the present invention nor have any of the inhibitors of angiogenesis described in the foregoing references been targeted at inhibition of $\alpha_v\beta_5$. Moreover, no references, other than the present invention, have implicated the $\alpha_v\beta_5$ integrin in neovascularization, particularly that induced by the growth factors, vascular endothelial growth factor (VEGF), transforming growth factor-$\alpha$ (TGF-$\alpha$) and epidermal growth factor (EGF).

Although the numbers of growth factors involved in the control of angiogenesis are limited, different levels of control of the process exist for conversion of a quiescent state to a neovascular state. See, D'Amore, *Investigative Ophthal. Visual Sci.*, 35:3974–3979 (1994). While some growth factors involved in angiogenesis are regulated at the synthesis level, others are regulated by the state of activation. These cellular events occur as a quiescent vessel undergoes neovascularization following injury or ischemia.

VEGF, in particular, is thought to be a major mediator of angiogenesis in a primary tumor and in ischemic ocular diseases. For review, see Folkman, *Nature Medicine*, 1:27–31 (1995). VEGF is a 46 kilodalton (kDa) homodimer that is an endothelial cell-specific angiogenic (Ferrara et al., *Endocrin. Rev.*, 13:18–32 (1992)) and vasopermeable factor (Senger et al., *Cancer Res.* 46:5629–5632 (1986)) that binds to high-affinity membrane-bound receptors with tyrosine kinase activity (Jakeman et al., *J. Clin. Invest.*, 89:244–253 (1992)).

Activation of receptor tyrosine kinases has recently been shown to promote integrin-dependent cell migration on extracellular matrix proteins. In particular, Klemke et al., *J. Cell Biol.*, 127:859–866 (1994) have implicated the EGF receptor (EGFR) tyrosine kinase in promoting cell motility but not adhesion of FG human pancreatic carcinoma cells on vitronectin using the $\alpha_v\beta_5$ integrin. The authors provide direct evidence that occupation of EGFR with the EGF ligand activates the tyrosine kinase activation of the EGFR that ultimately stimulates a protein kinase C (PKC)-dependent pathway leading to the induction of $\alpha_v\beta_5$-dependent cell migration of vitronectin substrate on which the cells are normally unable to migrate. Thus, the Klemke et al. findings provide evidence for correlating the presence of cytokines, specifically EGF, with integrin activity in cell migration. Activation of PKC has been shown to be involved in the regulation of angiogenesis in the chick chorioallantoic membrane model system. See, Tsopanoglou et al., *J. Vasc. Res.* 30:202–208 (1993). The authors identified specific activators and inhibitors of PKC that respectively stimulated and inhibited angiogenesis in the model system.

However, neither Klemke et al. nor Tsopanoglou et al. discussed above describe the role of cytokines and expression and/or activation of the $\alpha_v\beta_5$ integrin in promoting angiogenesis in various conditions and disease states and inhibition thereof with $\alpha_v\beta_5$-specific antagonists.

Recent experimental evidence has shown in a monkey model system of eye disease that retinal ischemia induced by retinal vein occlusion resulted in a rapid rise of VEGF in the aqueous chambers of the eye. This rise coincided with the iris neovascularization that was observed as described by Miller et al., *Am. J. Path.*, 145:574–584 (1994). Additional data in an mouse model system of proliferative retinopathy in which hypoxia is induced, VEGF messenger RNA was shown to increase within 6–12 hours of relative hypoxia that remained elevated until neovascularization developed. As the new blood vessels declined, so did the VEGF expression as described by Pierce et al., *Proc. Natl. Acad. Sci., USA*, 92:905–909 (1995).

Thus, the recent data as demonstrated in animal models of ischemia have correlated the induction of VEGF with that of ischemia followed by neovascularization. VEGF, as well as other growth factors, have also been implicated in other conditions and disease states involving neovascularization as reviewed by Folkman, *Nature Medicine*, 1:27–31 (1995).

The Folkman et al. reference also summarizes the current clinical approaches used to control undesirable angiogenesis. Patients in clinical trials have received therapeutic treatments with angiogenic inhibitors including platelet factor 4, a fumagillin-derivative, carboxy-aminotriazole, and the like. However, no references or current therapeutic references correlate the expression of $60_v\beta_5$ with angiogenesis, particularly that induced by VEGF. Thus, prior to the present invention, no one has described nor utilized a therapeutic regimen with $\alpha_v\beta_5$ antagonists to control angiogenesis in a tissue undergoing angiogenesis correlated with the presence and activation of $\alpha_v\beta_5$.

Therefore, other than the studies reported here on $\alpha_v\beta_3$ and the relationship with growth factors to angiogenesis. Applicants are unaware of any other demonstration that angiogenesis could be inhibited in a tissue using inhibitors of $\alpha_v\beta_5$-mediated cell adhesion. In particular, it has never been previously demonstrated that $\alpha_v\beta_5$ function is required for angiogenesis in a tissue or that $\alpha_v\beta_5$ antagonists can inhibit angiogenesis in a tissue, particularly in ocular neovascular diseases.

BRIEF DESCRIPTION OF THE INVENTION

The present invention demonstrates that in addition to an $\alpha_v\beta_3$-requiring angiogenesis pathway in tissues, a separate novel $\alpha_v\beta_5$-dependent pathway also exists. Thus, the invention describes inhibitors of $\alpha_v\beta_5$ that can inhibit angiogenesis. The invention further describes that $\alpha_v\beta_5$-mediated activity in promoting angiogenesis is correlated with growth factor (cytokine) activation of growth factor receptor tyrosine kinases and protein kinase C (PKC). The growth factors (cytokines) that function in this manner include vascular endothelial growth factor (VEGF), transforming growth factor-$\alpha$ (TGF-$\alpha$), epidermal growth factor (EGF), and the like.

The invention therefore describes methods for inhibiting angiogenesis in a tissue comprising administering to the tissue a composition comprising an angiogenesis-inhibiting amount of an $\alpha_v\beta_5$ antagonist.

The tissue to be treated can be any tissue in which inhibition of angiogenesis is desirable, such as diseased tissue where neovascularization is occurring. Exemplary tissues include ocular tissue undergoing neovascularization, inflamed tissue, solid tumors, metastases, tissues undergoing restenosis, and the like tissues. In preferred embodiments, the neovascularization associated with expression of $\alpha_v\beta_5$ is the result of exposure to the growth factors, VEGF, TGF-$\alpha$ and EGF.

Particularly preferred are therapeutic methods directed to inhibiting VEGF-induced vascularization in tissues such as the eye where angiogenesis is pronounced in diseases, including diabetic retinopathy (also called proliferative diabetic retinopathy), age-related macular degeneration, presumed ocular histoplasmosis, retinopathy of prematurity, sickle cell retinopathy and neovascular glaucoma. In further preferred embodiments, the therapeutic methods are directed to inhibiting angiogenesis that occurs in corneal neovascular disorders that include corneal transplantation, herpetic keratitis, luetic keratitis, pterygium, neovascular pannus associated with contact lens use, and the like.

An $\alpha_v\beta_5$ antagonist for use in the present methods is capable of binding to $\alpha_v\beta_5$ and competitively inhibiting the ability of $\alpha_v\beta_5$ to bind to the natural vitronectin ligand. Preferably, the antagonist exhibits specificity for $\alpha_v\beta_5$ over other integrins. In a particularly preferred embodiment, the $\alpha_v\beta_5$ antagonist inhibits binding of vitronectin or other RGD-containing ligands to $\alpha_v\beta_5$ but does not substantially inhibit binding of vitronectin to $\alpha_v\beta_3$ or $\alpha_{IIb}\beta_3$. A preferred $\alpha_v\beta_5$ antagonist can be a fusion polypeptide, a linear or cyclic polypeptide, a derivatized polypeptide, a monoclonal antibody or a functional fragment thereof, or an organic molecule that is a mimetic of an $\alpha_v\beta_5$ ligand that is also referred to as an organic mimetic, all of which specifically interacts with $\alpha_v\beta_5$.

Administration of the $\alpha_v\beta_5$ antagonists of this invention includes intraocular, intravenous, transdermal, intrasynovial, intramuscular and oral administration. In other preferred embodiments, administration is coordinated with a chemotherapeutic regimen to control tumorigenesis and cancer metastasis.

BRIEF DESCRIPTION OF THE DRAWINGS

In the drawings forming a portion of this disclosure:

FIGS. 1A–1D illustrate inhibition of cytokine-induced rabbit corneal angiogenesis by $\alpha_v$ integrin antibody antagonists. Induction of angiogenesis by treatment with either bFGF or VEGF and effects of treatment thereof with the $\alpha_v$ integrin antibody antagonists, P1F6 ($\alpha_v\beta_5$) and LM609 ($\alpha_v\beta_3$), are described in Example 4. OD and OS are respectively the right and left eyes of an experimental rabbit. Large arrows indicate corneal angiogenesis with edema while small arrows point to normal conjunctival limbal vessels. FIGS. 1A and 1B show induction of angiogenesis with bFGF while FIGS. 1C and 1D show that with VEGF. Rabbit corneas in FIGS. 1A and 1C show treatment with P1F6 while FIGS. 1B and 1D show treatment with LM609.

FIGS. 3A–3F photographically illustrate the effects of anti-integrin antibody treatment on the chick CAM preparation. The results are described in Example 6A. Angiogenesis is either induced with bFGF or VEGF followed by intravenous administration of phosphate buffered saline (PBS) as a control or with P1F6 or LM609 monoclonal antibodies described in the legend for FIG. 1. CAMs treated with bFGF are shown in FIGS. 3A, 3C and 3E while CAMs treated with VEGF are shown in FIGS. 3B, 3D and 3F. Control CAMs receiving intravenous injections of PBS are shown in FIGS. 3A and 3B. The P1F6 antibody was used to treat CAMs shown in FIGS. 3C and 3D while the LM609 antibody was used to treat CAMs in FIGS. 3E and 3F.

FIGS. 4A and 4B respectively show bFGF- and VEGF-induced angiogenesis. The results are discussed in Example 4.

FIGS. 6A and 6B respectively show bFGF- and VEGF-induced angiogenesis. The results are discussed in Example 6.

FIGS. 7A–7E respectively show angiogenesis induced with bFGF, TNF-$\alpha$, VEGF, TGF-$\alpha$ and PMA.

FIG. 14 shows the chemical structures of Compound 15, Compound 16, Compound 17 and Compound 18. The detailed synthesis of said compounds are described in Example 10O–R.

FIGS. 15A, 15B, 15C and 15D show the consecutive cDNA sequence of chicken MMP-2 along with the deduced amino acid sequence shown on the second line, as shown in FIGS. 15A, 15B and 15C. The third and fourth lines respectively show the deduced amino acid sequence of human and mouse MMP-2 as described in Example 7. The chicken cDNA sequence is listed in SEQ ID NO 23 along with the encoded amino acid sequence that is also presented separately as SEQ ID NO 24. The numbering of the first nucleotide of the 5' untranslated region and region encoding the proenzyme shown in FIG. 15A as a negative number is actually presented as number 1 in Sequence Listing making the latter appear longer than the figure; however, the nucleotide sequence is the figure is identical in length and sequence to that as presented in the listing with the exception of the numbering. Accordingly, references to nucleotide position for chicken or human MMP-2 in the specification, such as in primers for use in amplifying MMP-2 fragments, are based on the nucleotide position as indicated in the figure and not as listed in the Sequence Listing.

FIG. 16 shows the amino acid residue sequence of mature human MMP-2 protein having 631 residues. Amino acid residue positions of human MMP-2-derived fragments correspond to those in the figure. The amino acid residue sequence is listed in SEQ ID NO 25.

DETAILED DESCRIPTION OF THE INVENTION

A. DEFINITIONS

Figure 2B:
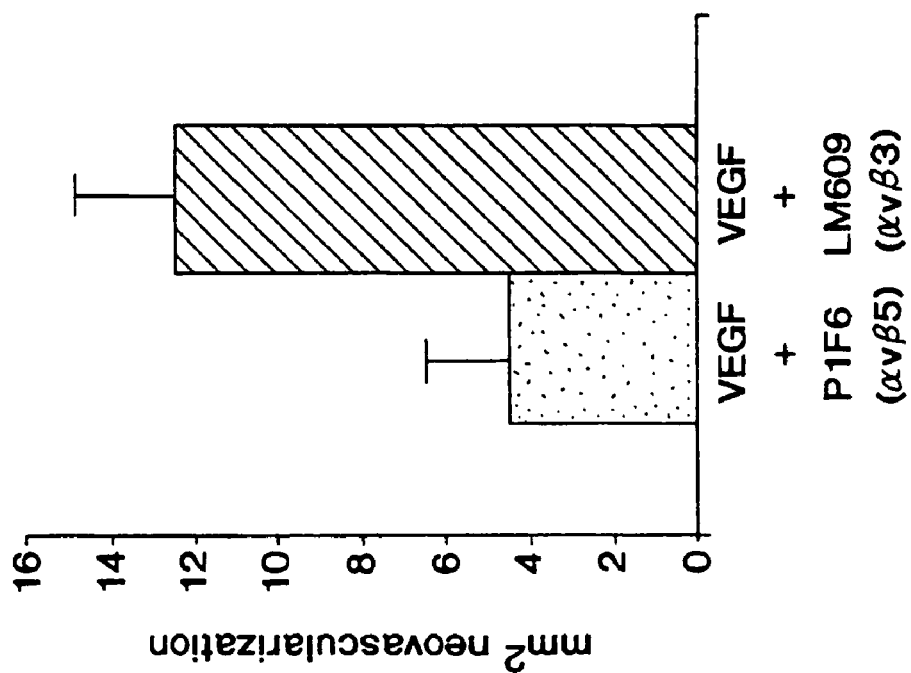
FIGS. 2A and 2B are histograms showing the mean neovascular area in mm$^2$ +/– the standard error (n=8 for each of two series) after induction respectively with either bFGF or VEGF followed by mAb treatment with either P1F6 or LM609. The results are discussed in Example 4.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822 (b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |
| In addition the following have the meanings below: | | |
| BOC tert-butyloxycarbonyl | | |
| DCCI dicylcohexylcarbodiimide | | |
| DMF dimethylformamide | | |
| OMe methoxy | | |
| HOBt 1-hydroxybezotriazole | | |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: A linear series of amino acid residues connected to one another by peptide bonds between the alpha-amino group and carboxy group of contiguous amino acid residues.

Peptide: A linear series of no more than about 50 amino acid residues connected one to the other as in a polypeptide.

Cyclic peptide: refers to a compound having a heteroatom ring structure that includes several amide bonds as in a typical peptide. The cyclic peptide can be a "head to tail" cyclized linear polypeptide in which a linear peptide's n-terminus has formed an amide bond with the terminal carboxylate of the linear peptide, or it can contain a ring structure in which the polymer is homodetic ore heterodetic and comprises amide bonds and/or other bonds to close the ring, such as disulfide bridges, thioesters, thioamides, guanidino, and the like linkages.

Protein: A linear series of greater than 50 amino acid residues connected one to the other as in a polypeptide.

Fusion protein: refers to a polypeptide containing at least two different polypeptide domains operatively linked by a typical peptide bond ("fused"), where the two domains correspond to peptides no found fused in nature.

Synthetic peptide: A chemically produced chain of amino acid residues linked together by peptide bonds that is free of naturally occurring proteins and fragments thereof.

B. GENERAL CONSIDERATIONS

The present invention relates generally to the discovery that angiogenesis is mediated by the specific vitronectin receptor $\alpha_v\beta_5$, and that inhibition of $\alpha_v\beta_5$ function inhibits angiogenesis. This discovery is important because of the role that angiogenesis plays in a variety of disease processes. By inhibiting angiogenesis, one can intervene in the disease, ameliorate the symptoms, and in some cases cure the disease. Where the growth of new blood vessels is the cause of, or contributes to, the pathology associated with a disease, inhibition of angiogenesis will reduce the deleterious effects of the disease. Examples include rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of new blood vessels in response to ischemia, resulting in growth factor-induced angiogenesis, growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, only new vessel growth contains substantial $\alpha_v\beta_5$, and therefore the therapeutic methods do not adversely effect mature vessels.

The discovery that inhibition of $\alpha_v\beta_5$ alone will effectively inhibit angiogenesis allows for the development of therapeutic compositions with potentially high specificity, and therefore relatively low toxicity. Although the invention discloses the use of peptide-based reagents which have the ability to inhibit one or more integrins, one can design other reagents which more selectively inhibit $\alpha_v\beta_5$. Therefore, certain peptide-based reagents do not have the side effect of inhibiting other biological processes other that those mediated by $\alpha_v\beta_5$.

For example, as shown by the present teachings, it is possible to prepare monoclonal antibodies highly selective for immunoreaction with $\alpha_v\beta_5$, and not $\alpha_v\beta_1$, $\alpha_v\beta_3$, or $\alpha_{IIb}\beta_3$, that are similarly selective for inhibition of $\alpha_v\beta_5$ function. In addition, RGD-containing peptides can be designed to be selective for inhibition of $\alpha_v\beta_5$, as described further herein.

Prior to the discoveries of the present invention, it was not known that angiogenesis, and any of the processes dependent on angiogenesis, could be inhibited in vivo by the use of reagents that antagonize the biological function of $\alpha_v\beta_5$.

C. METHODS FOR INHIBITION OF ANGIOGENESIS

The invention provides for a method of inhibiting angiogenesis in a tissue, and thereby inhibiting events in the tissue which depend upon angiogenesis. Generally, the method comprises administering to the tissue a composition comprising an angiogenesis-inhibiting amount of an $\alpha_v\beta_5$ antagonist.

The target tissue used in practicing the methods of this invention is defined as $\alpha_v\beta_5$-containing tissue that is characterized by the detectable presence of $\alpha_v\beta_5$ integrin receptor. In other words, an $\alpha_v\beta_5$-containing tissue is defined by the presence of the $\alpha_v\beta_5$ receptor complex in the cell membranes. Such tissues include epithelially and mesenchymally derived cells. The presence of the receptor can be determined by a number of means including immunoreactivity of the receptor with an anti-$\alpha_v\beta_5$ integrin receptor antibody, wherein the immunoreaction is detected in tissues by microscopy, by immunoprecipitation, by competition in ligand binding assays and the like techniques. Preferred antibodies for use in detecting the presence of $\alpha_v\beta_5$ in a tissue are described below and in Example 1. For example, the distribution of $\alpha_v\beta_5$ in kidney, skin and ocular tissues by immunofluorescence microscopy is described in Example 2.

In the context of the methods of this invention, an $\alpha_v\beta_5$-containing tissue is also characterized as one that has an indicia of angiogenesis. As described earlier, angiogenesis includes a variety of processes involving neovascularization of a tissue including "sprouting", vasculogenesis, or vessel enlargement, all of which angiogenesis processes are mediated by and dependent upon the expression of $\alpha_v\beta_5$. With the exception of traumatic wound healing, corpus luteum formation and embryogenesis, it is believed that the majority of angiogenesis processes are associated with disease processes and therefore the use of the present therapeutic methods are selective for the disease and do not have deleterious side effects.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

Eye diseases characterized by neovascularization present a particularly preferred target for therapy. Ocular neovascularization is the most common pathological change observed in the vast majority of eye diseases that result in catastrophic loss of vision. The growth of new blood vessels from the preexisting choroidal, retinal or paralimbal vessels can lead to edema, hemorrhage or fibrovascular membrane formation resulting in disruption of the normal anatomic relationships of the eye and concomitant loss of normal visual function.

Eye diseases characterized by angiogenesis include corneal neovascular disorders that include corneal transplantation, herpetic keratitis, luetic keratitis, pterygium, neovascular pannus associated with contact lens use, and the like. Additional eye diseases also include diabetic retinopathy (DR), age-related macular degeneration (ARMD), presumed ocular histoplasmosis (POHS), retinopathy of prematurity (ROP) and neovascular glaucoma and the like. While inhibition of angiogenesis in these diseases would not necessarily cure the underlying disease, it would significantly reduce the visual morbidity associated with them.

For example, 90% of the 300,000 persons having diabetes for over 25 years will have some form of DR that is a retinal disease characterized by leaking and/or proliferating blood vessels. Thirty percent of these patients will in fact have the latter condition that can be ameliorated with the therapeutic methods of this invention. For ARDM, 25% of the population over 65, approximately 630,000, will have some form of the disease with the expectation that by the year 2030, over 6.3 million individuals will have ARDM. As a result, having the ability to inhibit $\alpha_v\beta_5$-associated angiogenesis with the therapeutic compositions and methods of this invention has great medicinal value.

Thus, methods which inhibit angiogenesis in a diseased tissue ameliorate symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as are described in the Examples for detecting $\alpha_v\beta_5$-immunopositive nascent and immature vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

In particular, the methods and $\alpha_v\beta_5$ antagonist compositions of this invention are therapeutically useful for inhibiting angiogenesis that has been induced by growth factors, also referred to as cytokines. Under physiological conditions, angiogenesis is highly regulated and as previously published by Brooks et al., *Science*, 264:569–5761 (1994), has been shown to be activated by specific angiogenic molecules such as basic fibroblast growth factor (bFGF). Negative regulators of angiogenesis have also been described. Angiogenesis is thus regulated by an intricate balance between local stimulators and inhibitors. See, D'Amore, *Investigative Ophthal. Visual Sci.*, 35:3974–3979 (1994).

When the physiologic balance of angiogenic stimulators and inhibitors that tightly control the normally quiescent capillary vascular is disturbed, as occurs is certain disease states, capillary endothelial cells are induced to proliferate, migrate and ultimately differentiate to form new blood vessels.

Angiogenesis is characterized as an event cascade having a set of early events followed by a set of late events as reviewed by Leibovich, "Role of Cytokines in the Process of Tumor Angiogenesis", in "Human Cytokines: Their Role in Disease and Therapy", eds. Aggarwal and Puri, Chapter 35, Blackwell Science, Inc. (1995). The early events are preceded by the delivery of angiogenic growth factors and cytokines delivered from an extravascular source. The early events then proceed in the target microvasculature with the disruption of intercellular junctions, induction of expression of endothelial cell activation antigens and a proteolytic phenotype, and initiation of endothelial cell migration in a directional manner. The late events are characterized with autocrine and paracrine expression of growth factor and cytokine genes within the cells, endothelial cells, pericytes and smooth muscle cells, of the developing capillary bud. These cells in turn modulate the interactions of the cells with the extracellular matrix resulting in the formation of new functional capillary loops from existing mature vessels.

As discussed herein and in the Background, reports in the literature describe an association between the appearance of growth factors, including those associated with an increase of $\alpha_v\beta_5$ expression, namely VEGF, TGF-$\alpha$ and EGF, with the expansion of a tumor mass and in the onset of angiogenesis in proliferative neovascular eye diseases, both in humans and experimental animals.

Thus, VEGF, EGF, TGF-$\alpha$, among many others, are considered growth factors which are characterized by their properties of stimulating cellular growth. Growth factors are proteins that are secreted by one cell that act on the secreting cell or another cell. Their ability to act is dependent on the presence of growth factor receptors that are usually transmembrane proteins. Growth factors such as VEGF are also referred to generally as cytokines that are defined as polypeptide hormones, secreted by a cell, that affect growth and metabolism either of the same (autocrine) or of another (paracrine) cell. The term cytokine is not limited to molecules produced by cells of the immune system and the biological response modifiers of the same system. Thus, the term cytokine is a broad category of which one subcategory based on the type of biological response is stimulatory growth factors or enhancers such as VEGF, bFGF, EGF, TGF-$\alpha$, and the like. For review see, Aggarwal et al., "Common and Uncommon Features of Cytokines and Cytokine Receptors: An Overview", in "Human Cytokines: Their Role in Disease and Therapy", eds. Aggarwal and Puri, Chapter 1, Blackwell Science, Inc. (1995).

In the present invention, $\alpha_v\beta_5$-specific antagonists, and not growth factor antagonists such as antibodies against VEGF, are contemplated for use in inhibiting angiogenesis in a tissue. In preferred embodiments, the $\alpha_v\beta_5$ antagonists described herein are useful for inhibiting growth factor-induced angiogenesis in which the expression of the $\alpha_v\beta_5$ integrin receptor is induced. Preferred growth factors in this context include VEGF, EGF, TGF-$\alpha$ and the like.

As discussed in the Background, the growth factors EGF and VEGF are both known to bind to their cellular receptors that act as tyrosine kinases. Activation of the EGF receptor has further been shown to be correlated with activation of protein kinase C that results in activation of $\alpha_v\beta_5$ to allow for migration of specific cells on a vitronectin substrate. Thus, the mechanism of action between exposure to cytokines or growth factors and the coordinate response in integrin expression or activation is a complex biological process. As shown in the present invention (see Example 6A), treatment of tissues in either the rabbit eye model or the chick chorioallantoic model with the cytokine VEGF results in the $\alpha_v\beta_5$-potentiated angiogenesis that is dependent on activation of protein kinase C.

In a particularly preferred embodiment, the present invention contemplates the use of $\alpha_v\beta_5$ antagonists for inhibiting angiogenesis in any tissue in which angiogenesis has been induced by VEGF. For example, ischemia of the retina in various animal model systems has been shown to result in the upregulation of VEGF that is secreted from Muller cells, the production of which consequently induces neovascularization of tissues within the eye. See, Miller et al., *Am. J. Path.*, 145:574–584 (1994) and Pierce et al., *Proc. Natl. Acad. Sci., USA*, 92:905–909 (1995).

Thus, in the present invention, a tissue to be treated is a retinal tissue of a patient with diabetic retinopathy, macular degeneration, neovascular glaucoma or the like diseases as discussed above and the angiogenesis to be inhibited is retinal tissue angiogenesis where there is neovascularization of retinal tissue. Exemplary tissues, including corneal tissues, from patients with ocular neovascularization conditions or diseases are described above and in the Examples.

An exemplary model system for assessing the effects of an $\alpha_v\beta_5$ antagonist of this invention for treating retinal angiogenesis is the murine model of retinal neovascularization as described in Example 9.

In another related embodiment, a tissue to be treated is an inflamed tissue and the angiogenesis to be inhibited is inflamed tissue angiogenesis where there is neovascularization of inflamed tissue. In this class, the method contemplates inhibition of angiogenesis in arthritic tissues, such as in a patient with chronic articular rheumatism, in immune or non-immune inflamed tissues, in psoriatic tissue and the like.

The cytokines, interleukin 1 and tumor necrosis factor-$\alpha$, are thought to be associated with rheumatoid arthritis with their direct role in joint destructions based on the induction of adhesion molecule expression on endothelial cells and on enzyme release. See, Arend et al., *Arthritis & Rheumatism*, 38:151–160 (1995). Therapeutic regimens have been proposed for blocking both the cytokines with cytokine-specific inhibitors as well as targeting cell adhesion molecules that are expressed in the condition. See, Haskard et al., *Cell Adhesion Comm.*, 2:235–238 (1994).

Thus, inhibition of angiogenesis in arthritic conditions by addressing and directing the therapy to the involvement of the $\alpha_v\beta_5$ adhesion molecule is another preferred embodiment of the invention as prior to this invention.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues.

The role of the complex cytokine network that exists in solid human tumors is the subject of a review by Leek et al., *J. Leukocyte Biol.*, 56:423–435 (1994), the disclosure of which is hereby incorporated by reference. A number of cytokines including VEGF, acidic as well as basic FGF (bFGF), TGF-$\alpha$ and -$\beta$, EGF, TNF-$\alpha$, platelet derived endothelial cell growth factor, angiogenin, interferons $\alpha$ and $\gamma$, interleukins 1, 6 and 8 and the like are thought to influence various cellular mechanisms of angiogenesis in malignant tissues and cell lines. For example, in addition to its localization of various kinds of tumors, VEGF has recently been shown to be linked to angiogenesis in breast carcinoma as described by Brown et al. *Human Path.*, 26:86–91 (1995).

Tumors that secrete various cytokines and therein induce localized angiogenesis in response, specifically in the present invention with the cytokines VEGF, TGF-$\alpha$ and EGF and the resultant $\alpha_v\beta_5$-mediated angiogenesis, are identifiable by screening tumor tissue samples with anti-cytokine antibodies. Such methods are familiar to one of ordinary skill in the art for either cultured or biopsied tumor tissue samples. Antibodies against the above-described cytokines are commercially available through Oncogene Sciences (Uniondale, N.Y.) or Upstate Biotech Incorporated (Lake Placid, N.Y.). The screening of selected tumor tissues by these means thereby allows one to assess the potential of angiogenesis inhibitory activity by the $\alpha_v\beta_5$ antagonists of this invention.

Exemplary tumor tissue angiogenesis, and inhibition thereof, is described in the Examples.

Inhibition of tumor tissue angiogenesis is still another preferred embodiment of the invention because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases. In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferable to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods can also apply to inhibition of tumor tissue growth, to inhibition of tumor metastases formation, and to regression of established tumors. For the latter, the diminishment of a tumor mass is evaluated in the rabbit eye assay model as described for use in this invention or with a model system of a chimeric mouse:human model in which skin of a mouse having severe combined immunodeficiency (SCID) is replaced with human neonatal foreskin as described by Yan et al., *J. Clin. Invest.*, 91:986–996 (1993), the disclosure of which is hereby incorporated by reference. The latter model presents an additional in vivo model to investigate angiogenesis and inhibition thereof with the methods of this invention. Exemplary results with the rabbit tumor model and an $\alpha_v\beta_5$ antagonists of this invention are presented in Examples 5C and 6D while results for inbition of angiogenesis in the SCID mouse model is described in Example 8.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures. For inhibition of restenosis, the $\alpha_v\beta_5$ antagonist is typically administered after the angioplasty procedure for from about 2 to about 28 days, and more typically for about the first 14 days following the procedure.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases, particularly agricultural and domestic mammalian species, is sought with respect to the methods of this invention.

The present method for inhibiting angiogenesis in a tissue, and therefore for also practicing the methods for treatment of angiogenesis-related diseases, comprises contacting a tissue in which angiogenesis is occurring, or is at risk for occurring, with a composition comprising a therapeutically effective amount of an $\alpha_v\beta_5$ antagonist capable of inhibiting $\alpha_v\beta_5$ binding to its natural ligand. Thus, the method comprises administering to a patient a therapeutically effective amount of a physiologically tolerable composition containing an $\alpha_v\beta_5$ antagonist of the invention.

The dosage ranges for the administration of the $\alpha_v\beta_5$ antagonist depend upon the form of the antagonist, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

An $\alpha_v\beta_5$ antagonist is a molecule that blocks or inhibits the physiologic or pharmacologic activity of $\alpha_v\beta_5$ by inhibiting the binding activity of the receptor to its ligand, namely vitronectin. Preferred $\alpha_v\beta_5$ antagonists can either be a monoclonal antibody, a peptide or an organic-based molecule that is a mimetic of an $\alpha_v\beta_5$ ligand.

A therapeutically effective amount is an amount of $\alpha_v\beta_5$ antagonist sufficient to produce a measurable inhibition of angiogenesis in the tissue being treated, i.e., an angiogenesis-inhibiting amount. Inhibition of angiogenesis can be measured in situ by immunohistochemistry, as described herein, or by other methods known to one skilled in the art.

Insofar as an $\alpha_v\beta_5$ antagonist can take the form of an $\alpha_v\beta_5$ ligand organic mimetic, an RGD-containing peptide, an anti-$\alpha_v\beta_5$ monoclonal antibody, or fragment thereof, or an $\alpha_v\beta_5$ receptor mimetic it is to be appreciated that the potency, and therefore an expression of a "therapeutically effective" amount can vary. However, as shown by the present assay methods, one skilled in the art can readily assess the potency of a candidate $\alpha_v\beta_5$ antagonist of this invention.

Potency of an $\alpha_v\beta_5$ antagonist can be measured by a variety of means including inhibition of angiogenesis in the CAM assay, in the in vivo rabbit eye assay, and by measuring inhibition of binding of natural ligand to $\alpha_v\beta_5$, all as described herein, and the like assays.

A preferred $\alpha_v\beta_5$ antagonist has the ability to substantially inhibit binding of a natural ligand such as vitronectin to $\alpha_v\beta_5$ in solution at antagonist concentrations of less than 0.5 micromolar ($\mu$M), preferably less than 0.1 $\mu$M, and more preferably less than 0.05 $\mu$M. By "substantially" is meant that at least a 50 percent reduction in binding of vitronectin is observed by inhibition in the presence of the $\alpha_v\beta_5$ antagonist, and at 50% inhibition is referred to herein as an $IC_{50}$ value.

A more preferred $\alpha_v\beta_5$ antagonist exhibits selectivity for $\alpha_v\beta_5$ over other integrins. Thus, a preferred $\alpha_v\beta_5$ antagonist substantially inhibits vitronectin binding to $\alpha_v\beta_5$ but does not substantially inhibit binding of vitronectin to another integrin, such as $\alpha_v\beta_1$, $\alpha_v\beta_3$ or $\alpha_{IIb}\beta_3$. Particularly preferred is an $\alpha_v\beta_5$ antagonist that exhibits a 10-fold to 100-fold lower $IC_{50}$ activity at inhibiting vitronectin binding to $\alpha_v\beta_5$ compared to the $IC_{50}$ activity at inhibiting vitronectin binding to another integrin. Exemplary assays for measuring $IC_{50}$ activity at inhibiting vitronectin binding to an integrin are described in the Examples.

A therapeutically effective amount of an $\alpha_v\beta_5$ antagonist of this invention in the form of a monoclonal antibody is typically an amount such that when administered in a physiologically tolerable composition is sufficient to achieve a plasma concentration of from about 0.01 microgram ($\mu$g) per milliliter (ml) to about 100 $\mu$g/ml, preferably from about 1 $\mu$g/ml to about 5 $\mu$g/ml, and usually about 5 $\mu$g/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antagonist is in the form of a fragment of a monoclonal antibody, the amount can readily be adjusted based on the mass of the fragment relative to the mass of the whole antibody. A preferred plasma concentration in molarity is from about 2 micromolar ($\mu$M) to about 5 millimolar (mM) and preferably about 100 $\mu$M to 1 mM antibody antagonist.

A therapeutically effective amount of an $\alpha_v\beta_5$ antagonist of this invention in the form of a polypeptide, or other similarly-sized small molecule $\alpha_v\beta_5$ ligand mimetic, is typically an amount of polypeptide such that when administered in a physiologically tolerable composition is sufficient to achieve a plasma concentration of from about 0.1 microgram ($\mu$g) per milliliter (ml) to about 200 $\mu$g/ml, preferably from about 1 $\mu$g/ml to about 150 $\mu$g/ml. Based on a polypeptide having a mass of about 500 grams per mole, the preferred plasma concentration in molarity is from about 2 micromolar ($\mu$M) to about 5 millimolar (mM) and preferably about 100 $\mu$M to 1 mM polypeptide antagonist. Stated differently, the dosage per body weight can vary from about 0.1 mg/kg to about 300 mg/kg, and preferably from about 0.2 mg/kg to about 200 mg/kg, in one or more dose administrations daily, for one or several days.

The monoclonal antibodies, polypeptides or organic mimetics of this invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies, polypeptides or organic mimetics of this invention can be administered intraocularly, intravenously, intraperitoneally, intramuscularly, subcutaneously, intracavity, transdermally, and can also be delivered by peristaltic means.

The therapeutic compositions containing an $\alpha_v\beta_5$ antagonist of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier, or vehicle.

In one preferred embodiment as shown in the Examples, the $\alpha_v\beta_5$ antagonist is administered in a single dosage intravenously.

The compositions are administered in a manner compatible with the dosage formulation and in a therapeutically effective amount. The quantity to be administered and timing of administration depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimens for administration are also variable but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

D. THERAPEUTIC COMPOSITIONS

The present invention contemplates therapeutic compositions useful for practicing the therapeutic methods described herein. Therapeutic compositions of the present invention contain a physiologically tolerable carrier together with an $\alpha_v\beta_5$ antagonist as described herein, dissolved or dispersed therein as an active ingredient. In a preferred embodiment, the therapeutic $\alpha_v\beta_5$ antagonist composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Particularly preferred is the HCl salt when used in the preparation of cyclic polypeptide $\alpha_v\beta_5$ antagonists.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an $\alpha_v\beta_5$ antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

E. ANTAGONISTS OF INTEGRIN $\alpha_v\beta_5$ $\alpha_v\beta_5$ antagonists are used in the present methods for inhibiting angiogenesis in tissues, and can take a variety of forms that include compounds which interact with $\alpha_v\beta_5$ in a manner such that functional interactions with the natural $\alpha_v\beta_5$ ligands are interfered. Exemplary antagonists include analogs or mimetics of $\alpha_v\beta_5$ derived from the ligand binding site on $\alpha_v\beta_5$, mimetics of a natural ligand of $\alpha_v\beta_5$ that mimic the structural region involved in $\alpha_v\beta_5$-ligand binding interactions, polypeptides having a sequence corresponding to a functional binding domain of the natural ligand specific for $\alpha_v\beta_5$, particularly corresponding to the RGD-containing domain of a natural ligand of $\alpha_v\beta_5$, and antibodies which immunoreact with either $\alpha_v\beta_5$ or the natural ligand, all of which exhibit antagonist activity as defined herein.

1. Polypeptides

In one embodiment, the invention contemplates $\alpha_v\beta_5$ antagonists in the form of polypeptides. A polypeptide (peptide) $\alpha_v\beta_5$ antagonist can have the sequence characteristics of either the natural ligand of $\alpha_v\beta_5$ or $\alpha_v\beta_5$ itself at the region involved in $\alpha_v\beta_5$-ligand interaction and exhibits $\alpha_v\beta_5$ antagonist activity as described herein. A preferred $\alpha_v\beta_5$ antagonist peptide contains the RGD tripeptide and corresponds in sequence to the natural ligand in the RGD-containing region.

Preferred RGD-containing polypeptides have a sequence corresponding to the amino acid residue sequence of the RGD-containing region of a natural ligand of $\alpha_v\beta_5$ such as vitronectin, for which the sequence is well known.

A particularly preferred $\alpha_v\beta_5$ antagonist peptide preferentially inhibits $\alpha_v\beta_5$ binding to its natural ligand(s) when compared to other integrins, as described earlier. These $\alpha_v\beta_5$-specific peptides are particularly preferred at least because the specificity for $\alpha_v\beta_5$ reduces the incidence of undesirable side effects such as inhibition of other integrins. The identification of preferred $\alpha_v\beta_5$ antagonist peptides having selectivity for $\alpha_v\beta_5$ can readily be identified in a typical inhibition of binding assay, such as the ELISA assay described in the Examples.

A polypeptide of the present invention typically comprises no more than about 100 amino acid residues, preferably no more than about 60 residues, more preferably no more than about 30 residues. Peptides can be linear or cyclic, although particularly preferred peptides are cyclic. Preferred peptides are described in the Examples.

Where the polypeptide is greater than about 100 residues, it is typically provided in the form of a fusion protein or protein fragment, as described herein.

It should be understood that a subject polypeptide need not be identical to the amino acid residue sequence of a $\alpha_v\beta_5$ natural ligand, so long as it includes a sequence necessary for antagonizing the binding of an $\alpha_v\beta_5$ ligand to $\alpha_v\beta_5$ and is able to function as an $\alpha_v\beta_5$ antagonist in an assay such as those described herein.

A subject polypeptide includes any analog, fragment or chemical derivative of a polypeptide whose amino acid residue sequence is shown herein so long as the polypeptide is an $\alpha_v\beta_5$ antagonist. Therefore, a present polypeptide can be subject to various changes, substitutions, insertions, and deletions where such changes provide for certain advantages in its use. In this regard, an $\alpha_v\beta_5$ antagonist polypeptide of this invention corresponds to, rather than is identical to, the sequence of a recited peptide where one or more changes are made and it retains the ability to function as an $\alpha_v\beta_5$ antagonist in one or more of the assays as defined herein.

Thus, a polypeptide can be in any of a variety of forms of peptide derivatives, that includes amides, conjugates with proteins, cyclic peptides, polymerized peptides, analogs, fragments, chemically modified peptides, and the like derivatives.

The term "analog" includes any polypeptide having an amino acid residue sequence substantially identical to a sequence specifically shown herein in which one or more residues have been conservatively substituted with a functionally similar residue and which displays the $\alpha_v\beta_5$ antagonist activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

A "chemical derivative" refers to a subject polypeptide having one or more residues chemically derivatized by reaction of a functional side group. In addition to side group derivitations, a chemical derivative can have one or more backbone modifications including $\alpha$-amino substitutions such as N-methyl, N-ethyl, N-propyl and the like, and $\alpha$-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A particularly preferred derivative is a cyclic peptide according to the formula cyclo(Arg-Gly-Asp-D-Phe-NMe-Val), abbreviated c(RGDf-NMeV), in which there is an N-methyl substituted $\alpha$-amino group on the valine residue of the peptide and cyclization has joined the primary amino and carboxy termini of the peptide.

The term "fragment" refers to any subject polypeptide having an amino acid residue sequence shorter than that of a polypeptide whose amino acid residue sequence is shown herein.

When a polypeptide of the present invention has a sequence that is not identical to the sequence of an $\alpha_v\beta_5$ natural ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier.

Labels, solid matrices and carriers that can be used with the polypeptides of this invention are described hereinbelow.

Amino acid residue linkers are usually at least one residue and can be 40 or more residues, more often 1 to 10 residues, but do not form $\alpha_v\beta_5$ ligand epitopes. Typical amino acid residues used for linking are tyrosine, cysteine, lysine, glutamic and aspartic acid, or the like. In addition, a subject polypeptide can differ, unless otherwise specified, from the natural sequence of an $\alpha_v\beta_5$ ligand by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of forming salts with the peptides of the present invention include inorganic acids such as trifluoroacetic acid (TFA) hydrochloric acid (HCl), hydrobromic acid, perchloric acid, nitric acid, thiocyanic acid, sulfuric acid, methane sulfonic acid, acetic acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl salt is particularly preferred.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

In addition, a peptide of this invention can be prepared as described in the Examples without including a free ionic salt in which the charged acid or base groups present in the amino acid residue side groups (e.g., Arg, Asp, and the like) associate and neutralize each other to form an "inner salt" compound.

A peptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv. Enzymol.*, 32:221–96, 1969; Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently to generate the final linear polypeptide.

The resultant linear polypeptides prepared, for example, as described above may be reacted to form their corresponding cyclic peptides. An exemplary method for preparing a cyclic peptide is described by Zimmer et al., *Peptides* 1992, pp. 393–394, ESCOM Science Publishers, B.V., 1993. Typically, tertbutoxycarbonyl protected peptide methyl ester is dissolved in methanol and sodium hydroxide solution are added and the admixture is reacted at 20° C. (20C) to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

Alternate methods for cyclic peptide synthesis are described by Gurrath et al., *Eur. J. Biochem.*, 210:911–921 (1992), and described in the Examples.

In addition, the $\alpha_v\beta_5$ antagonist can be provided in the form of a fusion protein. Fusion proteins are proteins produced by recombinant DNA methods as described herein in which the subject polypeptide is expressed as a fusion with a second carrier protein such as a glutathione sulfhydryl transferase (GST) or other well known carrier. Preferred fusion proteins comprise an MMP-2 polypeptide described herein. The preparation of a MMP-2 fusion protein is described in the Examples.

Particularly preferred peptides or derivative peptides for use in the present methods in tissues primarily exhibiting $\alpha_v\beta_5$-associated angiogenesis are described in the Examples, and include the polypeptides shown in SEQ ID NOs 4, 6, 7, 8 and 9.

Also preferred are polypeptides derived from MMP-2 described herein, having sequences shown in SEQ ID Nos 11–22.

2. Monoclonal Antibodies

The present invention describes, in one embodiment, $\alpha_v\beta_5$ antagonists in the form of monoclonal antibodies which immunoreact with $\alpha_v\beta_5$ and inhibit $\alpha_v\beta_5$ binding to its natural ligand as described herein. The invention also describes cell lines which produce the antibodies, methods for producing the cell lines, and methods for producing the monoclonal antibodies.

A monoclonal antibody of this invention comprises antibody molecules that 1) immunoreact with isolated $\alpha_v\beta_5$, and 2) inhibit vitronectin binding to $\alpha_v\beta_5$. Preferred monoclonal antibodies which preferentially bind to $\alpha_v\beta_5$ include a monoclonal antibody having the immunoreaction characteristics of mAb P1F6 and mAb P5H9, which are described in the Examples.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules and those portions of an immunoglobulin molecule that contain the paratope, including those portions known in the art as Fab, Fab', F(ab')$_2$ and F(v), and also referred to as antibody fragments.

In another preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

For example, Fab and F(ab')$_2$ portions (fragments) of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact immunoglobulin molecules are preferred and are utilized as illustrative herein.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody bombing sites, each immunospecific for a different epitope, e.g., a bispecific monoclonal antibody.

A monoclonal antibody is typically composed of antibodies produced by clones of a single cell carried a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature,* 256:495–497 (1975), the description of which is incorporated by reference. Additional methods are described by Zola, *Monoclonal Antibodies: A Manual of Techniques,* CRC Press, Inc. (1987). The hybridoma supernates so prepared can then be screened for the presence of antibody molecules that immunoreact with $\alpha_v\beta_5$ and for inhibition of $\alpha_v\beta_5$ binding to natural ligands.

Briefly, to form the hybridoma from which the monoclonal antibody composition is produced, a myeloma or other self-perpetuating cell lines is fused with lymphocytes obtained from the spleen of a mammal hyperimmunized with a source of $\alpha_v\beta_5$.

It is preferred that the myeloma cell line used to prepare a hybridoma be from the same species as the lymphocytes. Typically, a mouse of the strain 129 G1X$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA), a variation of which is described in the Examples.

A monoclonal antibody of the present invention can also be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.,* 8:396, 1959) supplemented with 4.5 gm/l glucose, 20 mM glutamine, and 20% fetal calf serum. An exemplary inbred mouse strain is the Balb/c.

Other methods of producing a monoclonal antibody, a hybridoma cell or a hybridoma cell culture are also well known. See, for example, the method of isolating monoclonal antibodies from an immunological repertoire as described by Sastry, et al., *Proc. Natl. Acad. Sci., USA,* 86:5728–5732 (1989) and Huse et al., *Science,* 245:1275–1281 (1989).

Also contemplated by this invention is the hybridoma cell, and cultures containing a hybridoma cell that produce a monoclonal antibody of this invention. Particularly preferred is the hybridoma cell line that secretes monoclonal antibody mAb P1F6 and mAb P5H9, the preparation of which is described in the Examples.

The invention contemplates, in one embodiment, a monoclonal antibody that has the immunoreaction characteristics of mAb P1F6 or mAb P5H9.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity and the attendant affinity the antibody exhibits for the epitope are defined by the epitope with which the antibody immunoreacts. The epitope specificity is defined at least in part by the amino acid residue sequence of the variable region of the heavy chain of the immunoglobulin the antibody and in part by the light chain variable region amino acid residue sequence.

Use of the term "having the binding specificity of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens. In addition, human antibodies do not activate the immune system in the same manner as foreign antigens and foreign antibodies. Methods of preparing "humanized" antibodies are generally well known in the art and can readily be applied to the antibodies of the present invention.

Thus, the invention contemplates, in one embodiment, a monoclonal antibody of this invention that is humanized by grafting to introduce components of the human immune system without substantially interfering with the ability of the antibody to bind antigen.

3. $\alpha_v\beta_5$-Specific Mimetics

The present invention demonstrates that $\alpha_v\beta_5$ antagonists generally can be used in the present invention, the antagonists of which can include polypeptides, antibodies and other molecules, designated "mimetics", that have the capacity to interfere with $\alpha_v\beta_5$ function. Particularly preferred are antagonists which specifically interfere with $\alpha_v\beta_5$ function, and do not interfere with function of other integrins.

In this context it is appreciated that a variety of reagents may be suitable for use in the present methods, so long as these reagents possess the requisite biological activity. These reagents are generically referred to a mimetics because they possess the ability to "mimic" an $\alpha_v\beta_5$ ligand involved in the functional interaction of the receptor and ligand by blocking the ligand binding domain in the receptor, and thereby interfere with (i.e., inhibit) normal function. In an alternative embodiment, an $\alpha_v\beta_5$ antagonist may be a mimetic of the receptor rather than its ligand.

A mimetic is any molecule, other than an antibody or ligand-derived peptide, which exhibits the above-description properties. It can be a synthetic peptide, an analog or derivative of a peptide, a compound which is shaped like the binding pocket of the above-described binding domain such as an organic mimetic molecule, or other molecule.

A preferred mimetic of this invention is an organic-based molecule and thus is referred to as organic mimetic. Particularly preferred organic mimetic molecules that function as $\alpha_v\beta_5$ antagonists by being a mimetic to a ligand of $\alpha_v\beta_5$ are Compounds 7, 9, 10, 12, 14, 15, 16, 17 and 18 as described in Example 10.

The design of an $\alpha_v\beta_5$ mimetic can be conducted by any of a variety of structural analysis methods for drug-design known in the art, including molecular modeling, two-dimensional nuclear magnetic resonance (2-D NMR) analysis, x-ray crystallography, random screening of peptide, peptide analog or other chemical polymer or compound libraries, and the like drug design methodologies.

In view of the broad structural evidence presented in the present specification which shows that an $\alpha_v\beta_5$ antagonist can be a fusion polypeptide (e.g., an MMP-2 fusion protein), a small polypeptide, a cyclic peptide, a derivative peptide, an organic mimetic molecule, or a monoclonal antibody, that are diversely different chemical structures which share the functional property of selective inhibition of $\alpha_v\beta_5$, the structure of a subject $\alpha_v\beta_5$ antagonist useful in the present methods need not be so limited, but includes any $\alpha_v\beta_5$ mimetic, as defined herein.

F. METHODS FOR IDENTIFYING ANTAGONISTS OF $\alpha_v\beta_5$

The invention also describes assay methods for identifying candidate $\alpha_v\beta_5$ antagonists for use according to the present methods. In these assay methods candidate molecules are evaluated for their potency in inhibiting $\alpha_v\beta_5$ binding to natural ligands, and furthermore are evaluated for their potency in inhibiting angiogenesis in a tissue.

The first assay measures angiogenesis in the chick chorioallantoic membrane (CAM) and is referred to as the CAM assay. The CAM assay has been described in detail by others, and further has been used to measure both angiogenesis and neovascularization of tumor tissues. See Ausprunk et al., *Am. J. Pathol.*, 79:597–618 (1975) and Ossonski et al., *Cancer Res.*, 40:2300–2309 (1980).

The CAM assay is a well recognized assay model for in vivo angiogenesis because neovascularization of whole tissue is occurring. Actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as tumor tissue. Finally, the assay is particularly useful because there is an internal control for toxicity in the assay system. The chick embryo is exposed to any test reagent. As such, the health of the embryo is an indication of toxicity.

The second assay that measures angiogenesis is the in vivo rabbit eye model and is referred to as the rabbit eye assay. The rabbit eye assay has been described in detail by others and further has been used to measure both angiogenesis and neovascularization in the presence of angiogenic inhibitors such as thalidomide. See D'Amato, et al., *Proc. Natl. Acad. Sci., USA*, 91:4082–4085 (1994).

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent and as such the health of the rabbit is an indication of toxicity of the test reagent.

The third assay measures inhibition of direct binding of the natural ligand, vitronectin, to $\alpha_v\beta_5$, and a preferred embodiment is described in detail in the Examples. The assay typically measures the degree of inhibition of binding of a natural ligand, such as vitronectin, to isolated $\alpha_v\beta_5$ in the solid phase by ELISA, the inhibition of which is mediated by an $\alpha_v\beta_5$-specific inhibition.

Thus, the assay can also be used to identify compounds which exhibit specificity for $\alpha_v\beta_5$ and do not inhibit natural ligands from binding other integrins. The specificity assay is conducted by running parallel ELISA assays where both $\alpha_v\beta_5$ and other integrins are screened concurrently in separate assay chambers for their respective abilities to bind a natural ligand and for the candidate compound to inhibit the respective abilities of the integrins to bind a preselected ligand. Preferred screening assay formats are described in the Examples.

G. ARTICLE OF MANUFACTURE

The invention also contemplates an article of manufacture which is a labelled container for providing an $\alpha_v\beta_5$ antagonist of the invention. An article of manufacture comprises packaging material and a pharmaceutical agent contained within the packaging material.

The pharmaceutical agent in an article of manufacture is any of the $\alpha_v\beta_5$ antagonists of the present invention, formulated into a pharmaceutically acceptable form as described herein according the the disclosed indications. The article of manufacture contains an amount of pharmaceutical agent sufficient for use in treating a condition indicated herein, either in unit or multiple dosages.

The packaging material comprises a label which indicates the use of the pharmaceutical agent contained therein, e.g., for treating conditions assisted by the inhibition of angiogenesis, and the like conditions disclosed herein. The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of $\alpha_v\beta_5$-Specific Monoclonal Antibodies

The monoclonal antibodies, P1F6 and P5H9, were produced using standard hybridoma methods by immunization into RBF/DnJ mice with A549 lung carcinoma cells as described by Wayner et al., *J. Cell Biol.*, 113:919–929 (1991), the disclosure of which is hereby incorporated by reference. Spleens were removed from the immunized mice and fused with Ns-1/FOX-NY myeloma cells. Hybridomas producing antibody directed to carcinoma cell vitronectin receptors were screened by the specific inhibition of UCLA-P3 adhesion to vitronectin-coated surfaces as described by Wayner et al. and cloned by limiting dilution on thymocyte feeder layers.

Both the P1F6 and P5H9 monoclonal antibodies have been shown to specifically immunoreact with the $\alpha_v\beta_5$ complex, and not immunoreact with $\alpha_v$ subunit, with $\beta_5$ subunit, or with other integrins. The P1F6 monoclonal antibody is commercially available from Gibco BRL (Life Technologies, Inc., Gaithersburg, Md.) and the P5H9 monoclonal is available from Dr. E. Wayner at the Fred Hutchinson Cancer Research Institute, Seattle, Wash.

Other $\alpha_v\beta_5$ monoclonal antibodies for use in this invention are similarly derived and characterized as described herein. In addition, $\alpha_v\beta_5$ monoclonal antibodies are produced by fusing spleens isolated from mice that receive immunizations with the $\alpha_v\beta_5$ receptor in either an impure or purified form. Purification of the $\alpha_v\beta_5$ is a procedure well known to one or ordinary skill in the art of integrin biology and has also been described by Smith et al., *J. Biol. Chem.*, 265:11008–11013 (1990), the disclosure of which is hereby incorporated by reference. Once purified, the isolated receptor is prepared as an immunogen for immunizing mice as described in Section E2 and as prepared essentially as described by Kohler and Milstein, *Nature*, 256:495–497 (1975), the disclosure of which is hereby incorporated by reference. The resultant hybridoma clones are screened for reactivity with the immunogen and are then characterized as described in the following Examples.

2. Characterization of the Specificity of the Anti-$\alpha_v\beta_5$ Monoclonal Antibodies and Use in Mapping the Tissue Distribution of $\alpha_v\beta_5$ Expression A. Specificity for Vitronectin The P5H9 monoclonal antibody prepared in Example 1 was shown by Wayner et al., *J. Cell. Biol.*, 113:919–929 (1991) to block attachment of UCLA-P3 carcinoma cells to vitronectin while not affecting cell attachment to collagen or fibronectin. The same cells were also shown to contain only the $\alpha_v\beta_5$ vitronectin receptor and not one with $\alpha_v\beta_3$ specificity, immunoprecipitating a heterodimer consisting of an $\alpha$ chain (160 kD) and a $\beta$ chain (95 kD) with nonreducing conditions. The $\alpha_v\beta_5$ receptor detected by P5H9 was also shown to mediate adhesion of M21 melanoma cells and H2981 carcinoma cells to vitronectin. The P1F6 monoclonal antibody has the same immunoreactivity profile.

B. Immunofluorescence with Anti-Integrin Receptor Antibodies

During wound healing, the basement membranes of blood vessels express several adhesive proteins, including von Willebrand factor, fibronectin, and fibrin. In addition, several members of the integrin family of adhesion receptors are expressed on the surface of cultured smooth muscle and endothelial cells. See, Cheresh, *Proc. Natl. Acad. Sci., USA*, 84:6471 (1987); Janat et al., *J. Cell Physiol.*, 151:588 (1992); and Cheng et al., *J. Cell Physiol.*, 139:275 (1989).

In addition to the structure and function of the integrin $\beta_5$ subunit, the tissue distribution of the subunit by mapping with other anti-$\beta_5$ monoclonal antibodies has been described by Pasqualini et al., *J. Cell Sci.*, 105:101–111 (1993), the disclosure of which is hereby incorporated by reference.

The $\beta_5$ subunit-specific monoclonal antibodies described above, similar to those described in Example 1, were secreted from hybridomas that were prepared using splenocytes from a mouse that received immunizations with the A549 human lung carcinoma cell line. The hybridomas were selected by positive surface staining of A549 cells with the hybridomas culture supernatant and by immunoprecipitation of $\alpha_v\beta_5$ complexes from surface-labeled A549 extracts. The monoclonal antibodies were then used to map the tissue distribution of the $\beta_5$ subunit in normal human thymus, skin and kidney. Four micron thick sections were cut from the frozen tissue blocks on a cryostat microtome for subsequent streptavidin-biotin immunoperoxidase staining with antibodies specific for the $\beta_5$ integrins performed as described in the Pasqualini et al. reference.

Staining of thymic sections showed the distribution of $\beta_5$ on blood vessels. Hassal's corpuscles, cortical and medullary stromal cells, and basement membranes. Skin sections showed $\beta_5$ on the basal layer of the epidermis and on some dermal blood vessel walls, and kidney sections showed staining of glomerular regions, juxtaglomerular apparatus, proximal convoluted tubules and collecting tubules. Thus, the distribution of $\beta_5$ is heterogeneous to different cell types including and, more importantly, on capillary endothelial cells, the staining of which was consistent with staining of cultured umbilical vein endothelial cells.

C. Immunofluorescence of Human Retinal Tissue from Patients with Ocular Disease with Anti-Integrin Receptor Antibodies Ocular neovascularization is the most common pathological change observed in the vast majority of eye diseases that result in catastrophic loss of vision. The growth of new blood vessels from the pre-existing choroidal, retinal or paralimbal vessels can lead to edema, hemorrhage or fibrovascular membrane formation resulting in disruption of the normal anatomic relationships of the eye and concomitant loss of normal visual function.

Under physiological conditions, angiogenesis is highly regulated and has been shown to be activated by specific angiogenic cytokines such as basic fibroblast growth factor (bFGF) and tumor necrosis factor-$\alpha$ (TNF-$\alpha$). As described by Brooks et al., Science, 264:569–571 (1994), monoclonal antibodies against $\alpha_v\beta_3$ have been shown to be block both bFGF- and TNF-$\alpha$-induced angiogenesis in model systems including the CAM model described below. As described in Examples 4–6, monoclonal antibodies against $\alpha_v\beta_5$ block a separate pathway of angiogenesis, specifically that induced by vascular endothelial growth factor (VEGF), transforming growth factor-$\alpha$ (TGF-$\alpha$) and epidermal growth factor (EGF).

Thus, as described herein in the context of the present invention, two pathways of angiogenesis are defined by distinct integrins, $\alpha_v\beta_3$ and $\alpha_v\beta_5$. To investigate the expression and role of these integrins in human ocular disease, epiretinal neovascular membranes and subretinal neovascular membranes were obtained en bloc at vitrectomy from patients with proliferative diabetic retinopathy (PDR). These patients had been followed clinically and were selected for histological evaluation on the basis of having active, proliferative neovascular disease documented by clinical examination and fundus fluorescein angiography. The obtained tissue was frozen immediately in Tissue Tek cryopreservative and sectioned.

When the tissues from these patients were examined by immunofluorescence, the blood vessels were positive for the integrin $\alpha_v\beta_3$ as indicated by immunoreactivity with the mouse monoclonal antibody LM609. The distribution of the integrin appeared to be restricted to blood vessels and coincided with staining for a marker of blood vessels, von Willebrand Factor, as mapped with a rabbit antibody to the factor. The sites of immunoreactivity were visualized with either rhodamine-conjugated anti-mouse immunoglobulin or fluorescein-conjugated anti-rabbit immunoglobulin, the use of both of which allowed co-localization of the integrin location and blood vessel-specific antibodies.

Specimens obtained from normal eyes or patients with atrophic membranes free from actively proliferating blood vessels were negative for the integrin $\alpha_v\beta_3$ by immunofluorescence.

In parallel, the same tissues were analyzed immunohistochemically for the presence and distribution of $\alpha_v\beta_5$ with the anti-$\alpha_v\beta_5$ monoclonal antibody, P1F6, prepared in Example 1. The staining revealed that $\alpha_v\beta_5$ was present on blood vessels that co-localized with the distribution of von Willebrand factor. However, the non-vascular tissue also displayed limited fluorescence with the P1F6 antibody indicating a wider distribution of $\alpha_v\beta_5$. This was in contrast to the presence of $\alpha_v\beta_3$ that was limited to blood vessels.

When immunofluorescent staining of membranes was compared between $\alpha_v\beta_3$ and $\alpha_v\beta_5$ with the respective antibodies LM609 and P1F6, the pattern of staining on the blood vessel wall was virtually identical indicating that both $\alpha_v\beta_3$ and $\alpha_v\beta_5$ are displayed on the surface of newly proliferating human blood vessels present in neovascular eye diseases such as diabetic retinopathy.

The results described herein thus show that the $\alpha_v\beta_5$ integrin receptor is selectively expressed in specific tissue types in which angiogenesis is occurring, such as that seen with neovascular membranes from patients having active, proliferative neovascular disease. These tissues, along with those tissues exposed to particular growth factors as described below in Examples 4–6, therefore provided ideal targets for therapeutic aspects of this invention.

3. Preparation of Synthetic Peptides a. Synthesis Procedure

The cyclic polypeptides used in practicing the methods of this invention were synthesized using standard solid-phase synthesis techniques as, for example, described by Merrifield, Adv. Enzymol., 32:221–296 (1969), and Fields, G. B. and Noble, R. L., Int. J. Peptide Protein Res., 35:161–214 (1990).

Two grams (g) of BOC-Arg-Gly-Asp-D-Phe-Val-OMe (SEQ ID NO 1) were first dissolved in 60 milliliters (ml) of methanol to which was added 1.5 ml of 2 N sodium hydroxide solution to form an admixture. The admixture was then stirred for 3 hours at 20 degrees C. (20C). After evaporation, the residue was taken up in water and acidified to pH 3 with diluted HCl and extracted with ethyl acetate. The extract was dried over $Na_2SO_4$, evaporated again and the resultant BOC-Arg-Gly-Asp-D-Phe-Val-OH (SEQ ID NO 2) was stirred at 20C for 2 hours with 20 ml of 2 N HCl in dioxane. The resultant admixture was evaporated to obtain H-Arg-Gly-Asp-D-Phe-Val-OH (SEQ ID NO 3) that was subsequently dissolved in a mixture of 1800 ml of dichloromethane and 200 ml of dimethylformamide (DMF) followed by cooling to 0C. Thereafter, 0.5 g of dicyclohexylcarbodiimide (DCCI), 0.3 g of 1-hydroxybenzotriazole (HOBt) and 0.23 ml of N-methylmorpholine were added sequentially with stirring.

The resultant admixture was stirred for another 24 hours at 0C and then at 20C for yet another 48 hours. The solution was concentrated and treated with a mixed bed ion exchanger to remove salts. After the resulting resin was removed by filtration, the clarified solution was evaporated and the residue was purified by chromatography resulting in the recovery of cyclo(Arg-Gly-Asp-D-Phe-Val) (also listed in single letter code as c-RGDfV) (SEQ ID NO 4). The lower case letters in the peptide indicate the D form of the amino acid and not the L form as indicated by capital letters.

The cyclic control peptide, cyclo(Arg-Ala-Asp-D-Phe-Val) (also listed in single letter code as RADfV) (SEQ ID NO 5) was prepared as described above. The cyclic peptide c-RADfV (SEQ ID NO 5) has previously been shown to inhibiting binding of fibrinogen to the integrin $\alpha_v\beta_3$, and not inhibit binding of fibrinogen to the integrins $\alpha_{IIb}\beta_3$ or $\alpha_5\beta_1$ (Pfaff, et al., J. Biol. Chem., 269:20233–20238, 1994).

Other peptides that are specifically inhibitory to the binding of natural ligands to $\alpha_v\beta_5$ are similarly prepared as tested for specificity and range of activity as described in the following examples. These include the following peptides that were analogously obtained: cyclo(Gly-D-Arg-Gly-Asp-Phe-Val) (SEQ ID NO 6) and cyclo(Arg-Gly-Asp-Phe-D-Val) (SEQ ID NO 7). The peptides having the amino acid residue sequence Tyr-Thr-Ala-Glu-Cys-Lys-Pro-Gln-Val-Thr-Arg-Gly-Asp-Val-Phe (SEQ ID NO 8) and cyclo (Arg-Gly-Asp-D-Phe-NMeVal) (SEQ ID NO 9) were also synthetically prepared. In SEQ ID NO 9, the prefix "Me" in MeVal signifies that the valine in position 5 is modified by methylation at the alpha amino nitrogen in the amide bond of the valine residue.

b. Alternate Synthesis Procedure i. Synthesis of Cyclo-(Arg-Gly-Asp-DPhe-NmeVal), TFA Salt Fmoc-Arg(Mtr)-Gly-Asp(OBut)-DPhe-NMeVal-ONa (SEQ ID NO 41) is synthesized using solid-phase Merrifield-type procedures by sequentially adding NMeVal, DPhe, Asp(OBut), Gly and Fmoc-Arg(Mtr) in a step-wise manner to a 4-hydroxymethyl-phenoxymethyl-polystyrene resin (Wang type resin) (customary Merrifield-type methods of peptide synthesis are applied as described in Houben-Weyl, l.c., Volume 15/II, Pages 1 to 806 (1974). The polystyrene resin and amino acid residues precursors are commercially available from Aldrich, Sigma or Fluka chemical companies). After completion of sequential addition of the amino acid residues, the resin is then eliminated from the peptide chain using a 1:1 mixture of TFA/dichloromethane which provides the Fmoc-Arg(Mtr)-Gly-Asp(OBut)-DPhe-NMeVal-OH product (SEQ ID NO 42). The Fmoc group is then removed with a 1:1 mixture of piperidine/DMF which provides the crude Arg(Mtr)-Gly-Asp(OBut)-DPhe-NMeVal-OH (SEQ ID NO 43) precursor which is then purified by HPLC in the customary manner.

For cyclization, a solution of 0.6 g of Arg(Mtr)-Gly-Asp(OBut)-DPhe-NMeVal-OH (SEQ ID NO 43) (synthesized above) in 15 ml of DMF (dimethylformamide; Aldrich) is diluted with 85 ml of dichloromethane (Aldrich), and 50 mg of NaHCO₃ are added. After cooling in a dry ice/acetone mixture, 40 μl of diphenylphosphoryl azide (Aldrich) are added. After standing at room temperature for 16 hours, the solution is concentrated. The concentrate is gel-filtered (Sephadex G10 column in isopropanol/water 8:2) and then purified by HPLC in the customary manner. Treatment with TFA (trifluoroacetic acid)/H₂O (98:2) gives cyclo-(Arg-Gly-Asp-DPhe-NmeVal) (SEQ ID NO 9)×TFA which is then purified by HPLC in the customary manner; RT=19.5; FAB-MS (M+H): 589.

ii. Synthesis of "Inner Salt"

TFA salt is removed from the above-produced cyclic peptide by suspending the cyclo-(Arg-Gly-Asp-DPhe-Nme-Val) (SEQ ID NO 9)×TFA in water followed by evaporation under vacuum to remove the TFA. The cyclic peptide formed is referred to as an "inner salt" and is designated cyclo-(Arg-Gly-Asp-DPhe-NMeVal) (SEQ ID NO 9). The term "inner salt" is used because the cyclic peptide contains two oppositely charged residues which intra-electronically counterbalance each other to form an overall noncharged molecule. One of the charged residues contains an acid moiety and the other charged residue contains an amino moiety. When the acid moiety and the amino moiety are in close proximity to one another, the acid moiety can be deprotonated by the amino moiety which forms a carboxylate/ammonium salt species with an overall neutral charge.

iii. HCl Treatment to Give Cyclo-(Arg-Gly-Asp-DPhe-NMeVal) (SEQ ID NO 9)×HCl 80 mg of cyclo-(Arg-Gly-Asp-DPhe-NMeVal) (SEQ ID NO 9) are dissolved in 0.01 M HCl five to six times and freeze dried after each dissolving operation. Subsequent purification by HPLC give cyclo-(Arg-Gly-Asp-DPhe-NMeVal) (SEQ ID NO 9)×HCl; FAB-MS (M+H): 589.

iv. Methane Sulfonic Acid Treatment to Give Cyclo-(Arg-Gly-Asp-DPhe-NMeVal) (SEQ ID NO 9)×MeSO₃H 80 mg of cyclo-(Arg-Gly-Asp-DPhe-NMeVal) (SEQ ID NO 9) are dissolved in 0.01 M MeSO₃H (methane sulfonic acid) five to six times and freeze dried after each dissolving operation. Subsequent purification by HPLC give cyclo-(Arg-Gly-Asp-DPhe-NMeVal) (SEQ ID NO 9)×MeSO₃H; RT=17.8; FAB-MS (M+H): 589.

Alternative methods of cyclization include derivatizing the side group chains of an acyclic peptide precursor with sulfhydryl moieties, and when exposed to slightly higher than normal physiological pH conditions (pH 7.5), intramolecularly forms disulfide bonds with other sulfhydryl groups present in the molecule to form a cyclic peptide. Additionally, the C-terminus carboxylate moiety of an acyclic peptide precursor can be reacted with a free sulfhydryl moiety present within the molecule for producing thioester cyclized peptides.

TABLE I

| Peptide Designation | Amino Acid Sequence | SEQ ID NO |
| --- | --- | --- |
| 62184(66203*) | cyclo(RGDfV) | 4 |
| 62185(69601*) | cyclo(RADfV) | 5 |
| 62181 | cyclo(GrGDFV) | 6 |
| 62187 | cyclo(RGDFv) | 7 |
| 62880 | YTAECKPOVTRGDVF | 8 |
| 121974 (85189*) | cyclo (RGDf-NMeV) | 9 |
| 112784 | cyclo (RGEf-NMeV) | 10 |
| huMMP-2 (410–631)** | | 11 |
| huMMP-2 (439–631)** | | 12 |
| huMMP-2 (439–512)** | | 13 |
| huMMP-2 (439–546)** | | 14 |
| huMMP-2 (510–631)** | | 15 |
| huMMP-2 (543–631)** | | 16 |
| chMMP-2 (410–637)*** | | 17 |
| chMMP-2 (445–637)*** | | 18 |
| chMMP-2 (445–518)*** | | 19 |
| chMMP-2 (445–552)*** | | 20 |
| chMMP-2 (516–637)*** | | 21 |
| chMMP-2 (549–637)*** | | 22 |

*The peptides designated with an asterisk are prepared in HCl and are identical in sequence to the peptide designated on the same line; the peptides without an asterisk are prepared in TFA. Lower case letters indicate a D-amino acid; capital letters indicate a L-amino acid.

Figure 15A:
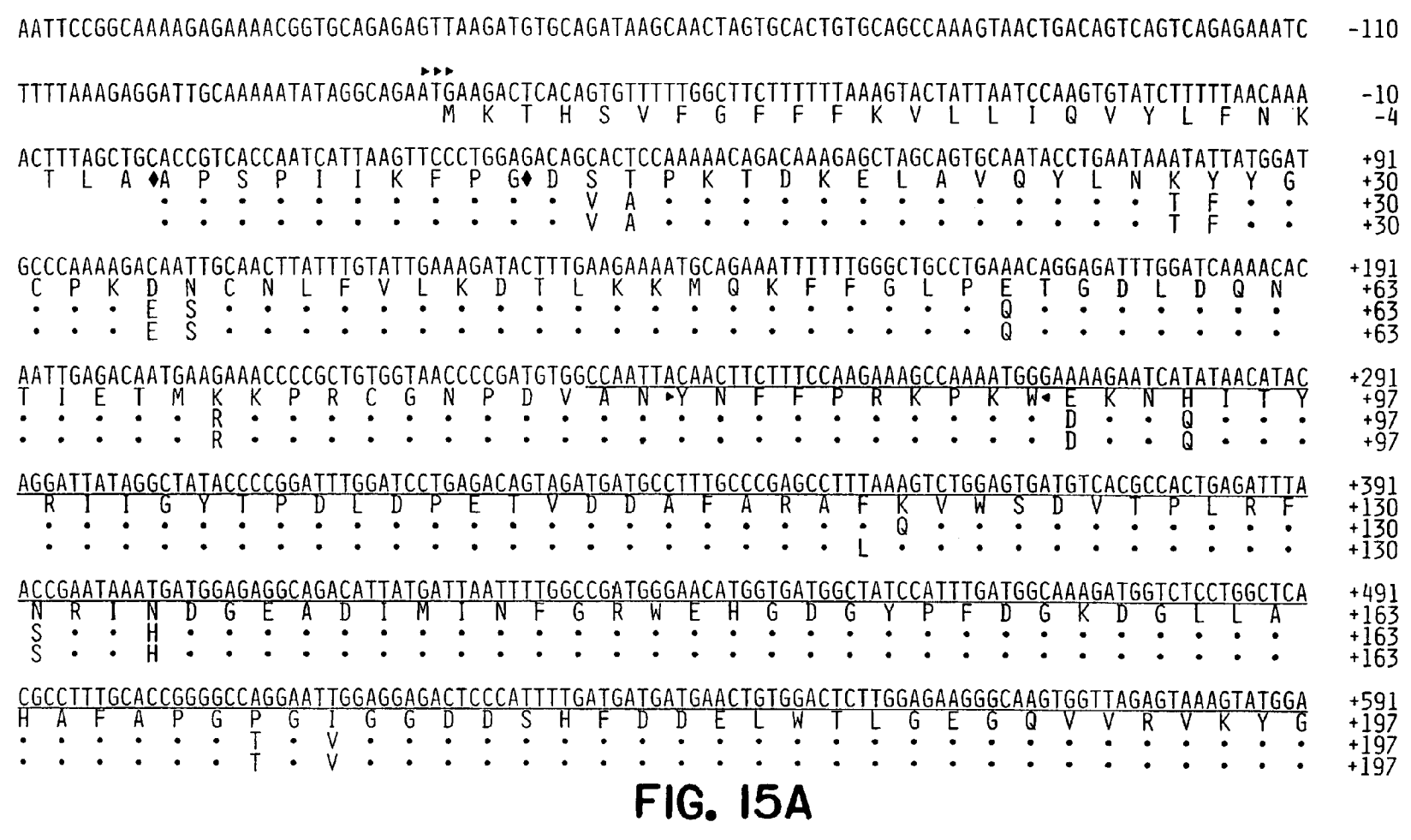
Figure 15B:
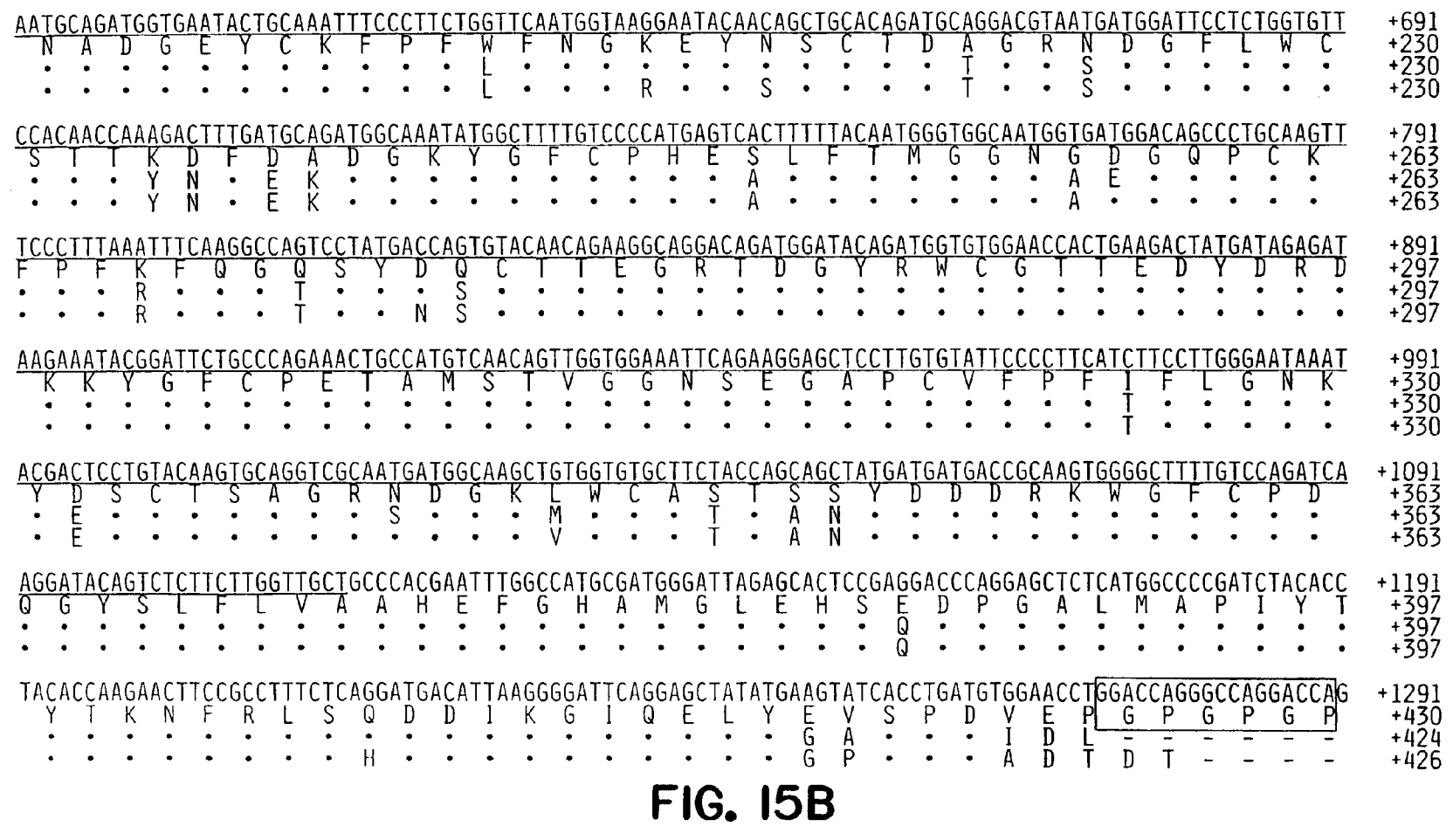
Figure 15C:
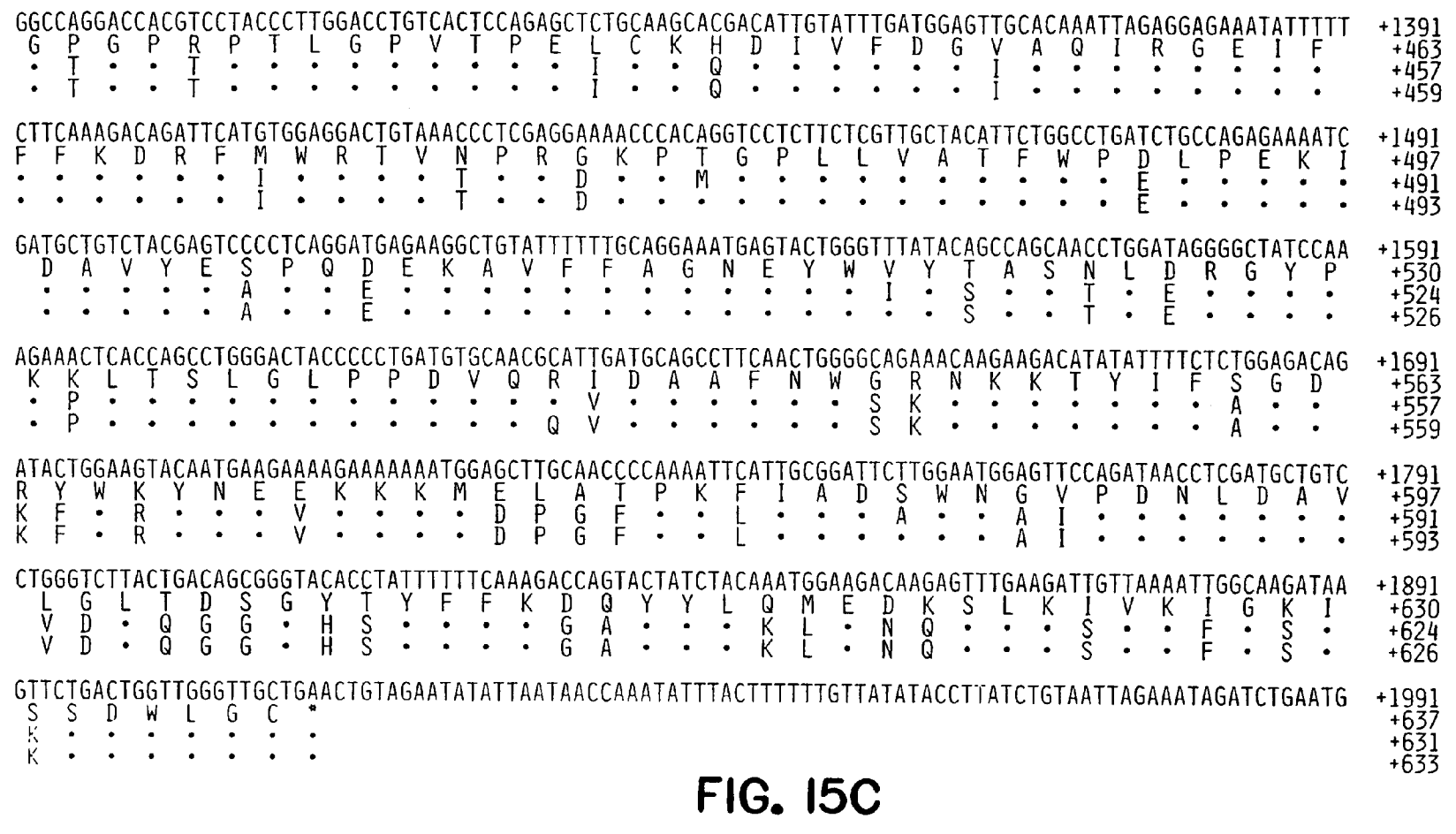

** The human MMP-2 amino acid residue sequences for synthetic peptides are indicated by the corresponding residue positions shown in FIGS. 15A–15C and also in FIG. 16. (MMP-2 refers to a member of the family of matrix metalloproteinase enzymes). The human MMP-2 sequences are listed with the natural cysteine residues but are not listed with engineered cysteine residues as described for the fusion peptides. The non-natural cysteine residues were substituted for the natural amino acid residue at the indicated residue positions in order to facilitate solubility of the synthetic as well as expressed fusion proteins and to ensure proper folding for presentation of the binding site.

*** The chicken MMP-2 amino acid residue sequences for synthetic peptides are indicated by the corresponding residue positions shown in FIGS. 15A–15C. The chicken MMP-2 sequences are listed with the natural cysteine residues but not with the engineered cysteine residues as described for the fusion peptides as described above.

4. Inhibition of Growth Factor-Induced Angiogenesis with $\alpha_v\beta_5$ Antagonists as Measured by In Vivo Rabbit Eye Model Assay The effect of anti-$\alpha_v\beta_5$ antagonists on growth factor-induced angiogenesis can be observed in naturally transparent structures as exemplified by the cornea of the eye. New blood vessels grow from the rim of the cornea, which has a rich blood supply, toward the center of the cornea, which normally does not have a blood vessels. Stimulators of angiogenesis, such as VEGF and TGF-α, when applied to the cornea induce the growth of new blood vessels from the rim of the cornea. Antagonists of angiogenesis, applied to the cornea, inhibit the growth of new blood vessels from the rim of the cornea. Thus, the cornea undergoes angiogenesis through an invasion of endothelial cells from the rim of the cornea into the tough collagen-packed corneal tissue which is easily visible. The rabbit eye model assay therefore provides in vivo model for the direct observation of stimulation and inhibition of angiogenesis following the implantation of compounds directly into the cornea of the eye.

A. In Vivo Rabbit Eye Model Assay

1) Angiogenesis Induced by Growth Factors

Angiogenesis was induced in the in vivo rabbit eye model assay with growth factors and is described in the following.

a. Preparation of Hydron Pellets Containing Growth Factor and Monoclonal Antibodies Hydron polymer pellets containing growth factor and monoclonal antibodies (mAbs) were prepared as described by D'Amato, et al., Proc. Natl. Acad. Sci., 91:4082–4085 (1994). The individual pellets contained 750 ng of the growth factor (also referred to as cytokine), specifically either bFGF or VEGF, bound to sucralfate (carafate) (Carafet, Marion Merrell Down Corporation, Cincinnati, Ohio) to stabilize the cytokines and ensure their slow release into the surrounding tissue. In addition, hydron pellets were prepared which contained either 40 μg of the mAb P1F6 (anti-$\alpha_v\beta_5$) or the control antibody, LM609 (anti-$\alpha_v\beta_3$), in PBS.

All of the mAbs tested were purified from ascites fluid using Protein-A Sepharose CL-4B affinity column chromatography according to well-known methods. The eluted immunoglobulin was then dialyzed against PBS and treated with Detoxi-gel (Pierce Chemicals, Rockford, Ill.) to remove endotoxin. Endotoxin has been shown to be potent angiogenic and inflammatory stimulant. Monoclonal antibodies were therefore tested for the presence of endotoxin with the Chromogenic Limulus Amebocyte Lysate Assay (BioWhittaker, Walkersville, Md.) and only those mAbs without detectable endotoxin were used in the rabbit eye model assay.

The pellets were cast in specially prepared Teflon pegs that had a 2.5 mm core drilled into their surfaces. Approximately 12 μl of casting material was placed into each peg and polymerized overnight in a sterile hood. Pellets were then sterilized by ultraviolet irradiation.

A series of eight animals were used for paired eye experiments where each animal received a Hydron implant containing a preselected cytokine with a preselected antibody or control immunoglobulin. Specifically, for each rabbit, one cornea was surgically implanted with a Hydron pellet containing either bFGF or VEGF in conjunction with mAb P1F6 and the other cornea was treated with either bFGF or VEGF in conjunction with MAb LM609. Individual pellets were implanted into surgically created "pockets" formed in the mid-stroma of the cornea of rabbits. The surgical procedure was done under sterile technique using a Wild model M691 operating microscope equipped with a beamsplitter to which was mounted a camera for photographically recording individual corneas. A 3 mm by 5 mm "pocket" was created in the corneal stroma by making a 3 mm incision to half the corneal thickness with a 69 Beaver blade. The stroma was dissected peripherally using an iris spatula and the pellet was implanted with its peripheral margin 2 mm from the limbus.

During the following 12 days, the cytokines and mAbs diffused from the implanted pellets into the surrounding tissue thereby effecting angiogenesis from the rim of the cornea.

The left and right corneas are respectively referred to as OS and OD. The corneas were then observed for 12 days. Photographs were taken on postoperative day 10, the time at which neovascularization is maximal.

Figure 2A:
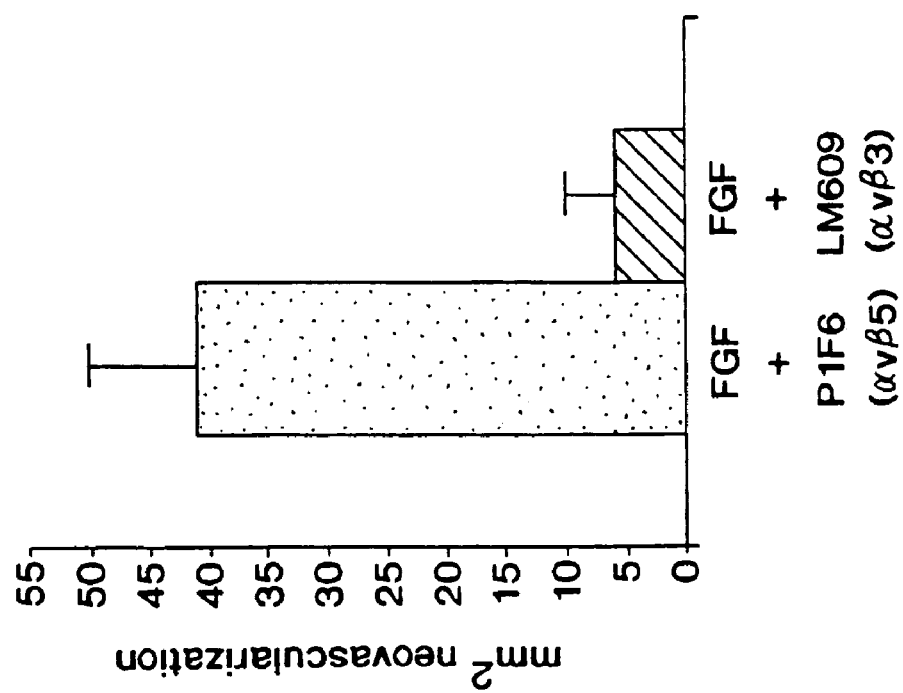

Representative photographic results of the above-treatments with cytokine/mAb admixtures are shown in FIGS. 1A–1D. The parallel quantitation of mAb inhibition of cytokine-induced angiogenesis is shown in FIGS. 2A and 2B. In FIGS. 1A and 1D, in which corneas were respectively exposed to bFGF/P1F6 and VEGF/LM609 combinations, cytokine-induced angiogenesis with edema is prominent as indicated by the large arrows. Therefore, the $\alpha_v\beta_5$ antibody, P1F6, was not effective at inhibiting bFGF-induced angiogenesis. Similarly, the $\alpha_v\beta_3$ antibody, LM609, was not effective at inhibiting VEGF-induced angiogenesis.

In contrast, when the cytokine/mAb combinations of bFGF/LM609 and VEGF/P1F6 were used in the rabbit model, the cytokine-induced angiogenesis was inhibited by the antibodies as shown in FIGS. 1B and 1C, respectively. In these figures, normal conjunctival limbal vessels indicated by the small arrows are shown indicating effectiveness of the integrin antibodies in inhibiting one type of cytokine-induced angiogenesis.

The effects of specific mAb integrin immunoreactivity on the above cytokine-induced angiogenesis is also quantified as shown in FIGS. 2A and 2B. Angiogenesis was stimulated with either bFGF or VEGF as shown respectively in FIGS. 2A and 2B. The treated eyes were photographed daily through a Wild operating microscope outfitted with a Nikon camera. Photographs were recorded on Kodak Ektachrome 64T slide film and images were converted for computer-assisted quantitation using Biorad's Molecular Analyst 1.1 software after acquisition through a Model GS670 imaging densitometer. Histograms illustrating the mean neovascular area +/− the standard error (n=8 for each of two series) after exposure to the mAbs P1F6 or LM609.

As shown in FIG. 2A, LM609 reduced bFGF-induced angiogenesis by 86% ($p<0.005$, paired t-test) when compared to treatment of the paired eye on the same animal with P1F6. When VEGF was used to stimulate angiogenesis as shown in FIG. 2B, the opposite effect was observed where P1F6 reduced the mean area of neovascularization by 60% ($p<0.03$, paired t-test) compared to the LM609-treated eye that had a minimal effect on VEGF-induced angiogenesis.

Significantly, only the newly cytokine-induced blood vessels were effected by exposure to a particular mAb while the pre-existing perilimbal vessels were unaffected by either mAb suggesting that the effects observed are restricted to newly forming blood vessels of the cornea.

Similar assays are performed with synthetic peptides prepared in Example 3 and as described below for use in inhibiting cytokine-induced angiogenesis that is specifically correlated with $\alpha_v\beta_5$ expression.

To confirm these results indicating that angiogenesis induced by a particular cytokine was only effected by one type of anti-integrin antibody, specifically that $\alpha_v\beta_5$ integrin receptor plays a role in VEGF-induced angiogenesis, another neovascular model of the chick chorioallantoic membrane (CAM) was evaluated with the combinations of cytokines and integrin antibodies as shown in the next Example.

b. Treatment with Polypeptides

Each experiment consisted of eight rabbits in which one eye received a pellet comprising 100 nanograms (ng) bFGF and the other eye received a pellet comprising 1 microgram (ug) VEGF. The pellets were inserted into the corneal pocket as described above, and the cytokines subsequently stimulated the growth of new blood vessels into the cornea. Peptides were administered subcutaneously (s.q.) in 1 ml PBS at an initial dosage of 50 ug per kg rabbit the day of pellet insertion, and daily s.q. dosages were given at 20 ug/kg thereafter. After 7 days, the cornea were evaluated as described above.

Rabbits receiving control peptide 69601 showed substantial corneal blood vessel growth at 7 days, in both vFGF and VEGF stimulated eyes. Rabbits receiving peptide 85189 showed less than 50% of the amount of corneal blood vessel growth compared to controls in vFGF-stimulated eyes and nearly 100% inhibition in VEGF-stimulated eyes.

5. Angiogenesis in the Chick Chorioallantoic Membrane (CAM) Preparation

A. Characterization of the Untreated CAM

1) Preparation of the CAM

Angiogenesis can be induced on the chick chorioallantoic membrane (CAM) after normal embryonic angiogenesis has resulted in the formation of mature blood vessels. Angiogenesis has been shown to be induced in response to specific cytokines or tumor fragments as described by Leibovich et al., Nature, 329:630 (1987) and Ausprunk et al., Am. J. Pathol., 79:597 (1975). CAMs were prepared from chick embryos for subsequent induction of angiogenesis and inhibition thereof as described below and in Example 6 with the $\alpha_v\beta_5$ antagonists of this invention.

Ten day old chick embryos were obtained from McIntyre Poultry (Lakeside, Calif.) and incubated at 37C with 60% humidity. A small hole was made through the shell at the end of the egg directly over the air sac with the use of a small crafts drill (Dremel, Division of Emerson Electric Co., Racine, Wis.). A second hole was drilled on the broad side of the egg in a region devoid of embryonic blood vessels determined previously by candling the egg. Negative pressure was applied to the original hole, which resulted in the CAM (chorioallantoic membrane) pulling away from the shell membrane and creating a false air sac over the CAM. A 1.0 centimeter (cm)×1.0 cm square window was cut through the shell over the dropped CAM with the use of a small model grinding wheel (Dremel). The small window allowed direct access to the underlying CAM.

The resultant CAM preparation was then used at 10 days of embryogenesis where angiogenesis has subsided. The preparation was thus used in this invention for inducing renewed angiogenesis in response to cytokine treatment.

2) Histology of the CAM

To analyze the microscopic structure of the chick embryo CAMs, six micron (μm) thick sections were cut from the frozen blocks on a cryostat microtome for immunofluorescence analysis.

Typical of an untreated 10 day old CAM is an area devoid of blood vessels. As angiogenesis in the CAM system is subsiding by this stage of embryogenesis, the system is useful in this invention for stimulating with various cytokines the production of new vasculature from existing vessels from adjacent areas into areas of the CAM currently lacking any vessels.

As shown in the CAM model and in the following Examples, while the blood vessels are undergoing new growth in normal embryogenesis or induced by cytokines, the blood vessels are expressing $\alpha_v\beta_3$ and $\alpha_v\beta_5$.

B. Angiogenesis Induced by Growth Factors

Angiogenesis has been shown to be induced by cytokines or growth factors as described in Example 4A in the rabbit eye model. In the experiments described herein, angiogenesis in the rabbit corneal preparation described in Example 4 was similarly induced by growth factors that were topically applied onto the CAM blood vessels as described herein.

Angiogenesis was induced by placing a 5 millimeter (mm)×5 mm Whatman filter disk (Whatman Filter paper No. 1) saturated with Hanks Balanced Salt Solution (HBSS, GIBCO, Grand Island, N.Y.) or HBSS containing preselected cytokines at a preselected concentration, i.e. one to test the effect on angiogenesis, on the CAM of a 10 day chick embryo in a region devoid of blood vessels and the windows were later sealed with tape. Angiogenesis was monitored by photomicroscopy after 72 hours. CAMs were snap frozen then 6 μm cryostat sections were fixed with acetone and stained by immunofluorescence as described in Example 2B and 2C with 10 μg/ml of selected anti-integrin antibodies, including those directed against $\alpha_v\beta_5$ as described in Example 1.

Previous studies by Brooks et al., Science, 264:569–571 (1994), have shown that blood vessels are readily apparent in both the bFGF and TNF-α treated preparations but are not present in the untreated CAM. The authors have also shown that $\alpha_v\beta_3$ expression was enhanced following bFGF-induced angiogenesis. While the expression of integrin $\beta_1$ did not change from that seen in an untreated CAM, $\beta_1$ was also readily detectable on stimulated blood vessels.

These published findings indicated that in both human and chick, blood vessels involved in angiogenesis show enhanced expression of $\alpha_v\beta_3$. Consistent with this, expression of $\alpha_v\beta_3$ on cultured endothelial cells were induced by various cytokines in vitro as described by Janat et al., J. Cell Physiol., 151:588 (1992); Enenstein et al., Exp. Cell Res., 203:499 (1992) and Swerlick et al., J. Invest. Derm., 99:715 (1993).

In this invention, a separate cytokine-mediated pathway for simulating angiogenesis that is dependent upon expression and activation of a different adhesive integrin receptor, $\alpha_v\beta_5$, has now been determined. The effect of exposure of a CAM as described herein to the cytokines VEGF, TGF-α and EGF in relationship to the expression of $\alpha_v\beta_5$, to angiogenesis and inhibition thereof with $\alpha_v\beta_5$ antagonists is described in Example 6.

C. Angiogenesis Induced by Tumors

To investigate the role of $\alpha_v\beta_5$ in tumor-induced angiogenesis, various $\alpha_v\beta_5$-negative human melanoma and carcinoma fragments are used in the CAM assay that are previously grown and isolated from the CAM of 17 day chick embryo as described by Brooks et al., J. Cell Biol., 122:1351 (1993) and as described herein.

Angiogenesis is induced in the CAM assay system by direct apposition of a tumor fragment on the CAM. Preparation of the chick embryo CAM is identical to the procedure described above. Instead of a filter paper disk, a 50 milligram (mg) to 55 mg in weight fragment of one $\alpha_v\beta_5$-negative tumor resulting from growth of cell line suspensions described below, is placed on the CAM in an area originally devoid of blood vessels.

The cell lines, rabdomyosarcoma, myeloid (HL-60 or KG-1), and lymphoid (T cells—Jurkat, HPB/ALL, PEER, and various B cell lines) as described by Pasqualini et al. *J. Cell Sci.*, 105:101–111 (1993), are used to grow the solid human tumors on the CAMs of chick embryos. A single cell suspension of the various cell lines are first applied to the CAMs in a total volume of 30 µl of sterile HBSS. The windows are sealed with tape and the embryos are incubated for 7 days to allow growth of human tumor lesions. At the end of 7 days, now a 17 day embryo, the tumors are resected from the CAMs and trimmed free of surrounding CAM tissue. The tumors are sliced into 50 mg to 55 mg tumor fragments for use in angiogenesis. The tumor fragments are placed on a new set of 10 day chick embryo CAMs as described in Example 5A in an area devoid of blood vessels.

Tumors grown in vivo on the chick embryo CAMs with and without topical or intravenous application of $\alpha_v\beta_5$-inducing cytokines (VEGF, TGF-$\alpha$, or EGF) are then stained for $\alpha_v\beta_5$ expression with mAbs, P1F6 or P5H9, as previously described.

These CAM tumor preparations are then subsequently treated as described in Examples 6C and 6D for measuring the effects of antibodies and peptides including MMP-2 C-terminal fragments on tumor-induced angiogenesis.

In one embodiment, hamster melanoma cells, CS-1, obtained from Dr. Caroline Damsky from University of California at San Francisco, were used in the CAM assay as described above for formation of melanoma tumors. Following the transfer of approximately a 50 mg CS-1 tumor fragment on a new 10 day chick embryo CAM, separate preparations received an intravenous injections of either 100 µg or 300 µg of P1F6 antibody, LM609 antibody or control CSAT (anti-$\beta1$) antibody. An additional control included a preparation that received no treatment. The results are discussed below in Example 6D.

6. Inhibition of Angiogenesis as Measured in the CAM Assay

A. Inhibition of Growth Factor-Induced Angiogenesis by Intravenous Application of Inhibitors The effect on growth factor-induced angiogenesis with monoclonal antibodies intravenously injected into the CAM preparation was evaluated for use as an in vivo model system of this invention.

Following active neovascularization, once the vessels have stopped developing, the expression of $\alpha_v\beta_5$ diminishes to levels not detectable by immunofluorescence analysis. This regulation of $\alpha_v\beta_5$ expression in blood vessels undergoing angiogenesis as contrasted to the lack of expression in mature vessels provides for the unique ability of this invention to control and inhibit angiogenesis as shown below as modeled in the CAM angiogenesis assay system.

The preparation of the chick embryo CAMs for intravenous injections was essentially as described above.

Angiogenesis was first induced on 10 day old chick embryos by application of growth factor-saturated filter disks. Specifically, in the first assays, angiogenesis was induced by exposure to either bFGF or VEGF, each at a concentration of 150 ng/ml.

For application of growth factors, during the candling procedures, prominent blood vessels were selected and marks were made on the egg shell to indicate their positions. The holes were drilled in the shell, the CAMs were dropped and growth factor-saturated filter papers were then separately placed on the CAMs as described above. The windows were sealed with sterile tape and the embryos were replaced in the incubator.

Twenty four hours later, a second small window was carefully cut on the lateral side of the egg shell directly over prominent blood vessels selected previously. The outer egg shell was carefully removed leaving the embryonic membranes intact. The shell membrane was made transparent with a small drop of mineral oil (Perkin-Elmer Corp, Norwalk, Conn.) which allowed the blood vessels to be visualized easily. Then, phosphate buffered saline (PBS), 75 µg of purified sterile anti-integrin antibodies or 75 µg of synthetic peptides (cyclic peptide RGDfV, SEQ ID NO 4 and control cyclic peptide RADfV, SEQ ID NO 5) in PBS were injected into blood vessels apparent on the growth factor-induced CAMs. The windows were sealed with tape and the embryos were allowed to incubate until 72 hours.

The filter discs and representative surrounding CAM tissues were photographed in a stereomicroscope (FIGS. 3A–3F and FIGS. 5A–5F) and the mean angiogenic index +/− the standard error was determined for 12 CAMs per condition (FIGS. 4A–4B and FIGS. 6A–6B). Angiogenesis was scored for each embryo in a double blind manner by analyzing the number and extent of branching of blood vessels within the area of each disc. The scores ranged from 1 (low) to 4 (high) and the angiogenesis index was determined by subtracting a background of 1 from all data.

Specificity of integrin antibody-mediated inhibition of growth factor-induced angiogenesis in the CAM model mirrored that seen in the rabbit cornea model described above. As respectively shown in FIGS. 3A and 3B, both bFGF and VEGF caused angiogenesis in the control PBS-treated CAM. Treatment with the $\alpha_v\beta_5$-specific antibody, P1F6, however, resulted in inhibition of VEGF-induced angiogenesis as shown in FIG. 3D while no inhibition was detected on bFGF-induced angiogenesis as seen in FIG. 3C. In contrast, the LM609, $\alpha_v\beta_3$-specific antibody inhibited bFGF-induced angiogenesis (FIG. 3E) but had little effect on angiogenesis in the VEGF-induced CAM (FIG. 3F).

Figure 4A:
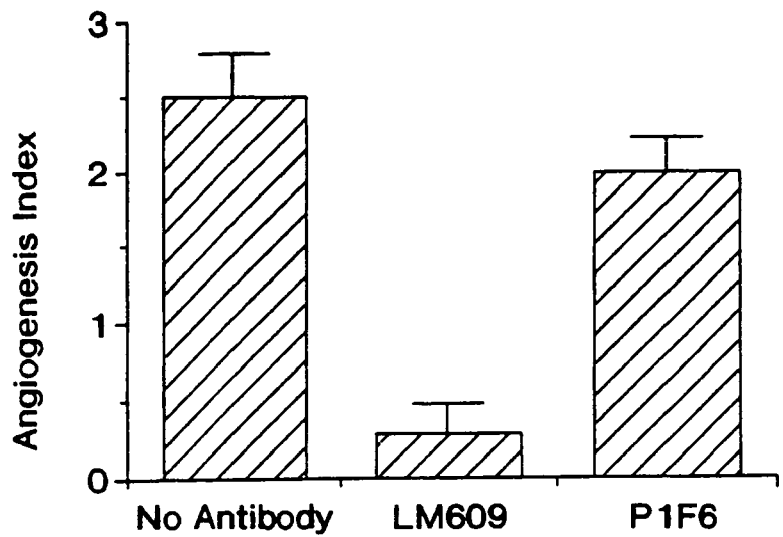
FIGS. 4A and 4B provide in histogram format the quantitation of results shown in FIGS. 3A–3F. The angiogenesis index is plotted on the Y-axis against control or antibody treatment.
Figure 4B:
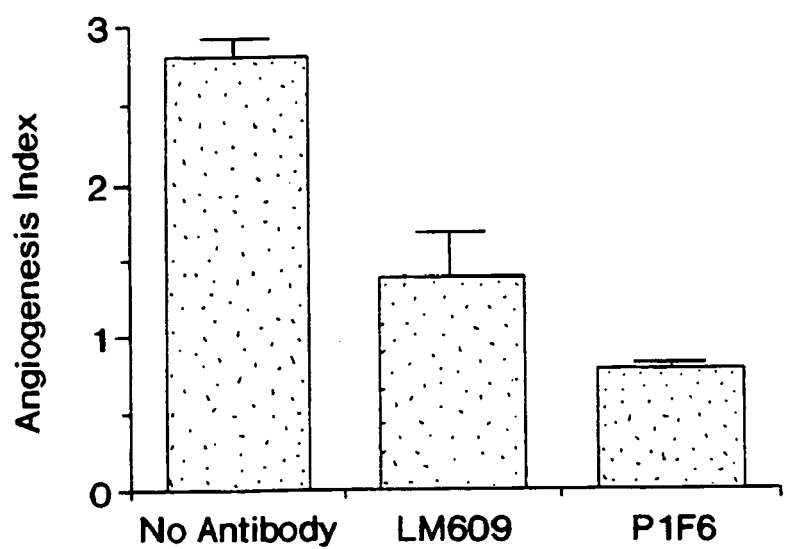

These results are also shown in the bar graphs of FIGS. 4A and 4B, respectively for both bFGF- and VEGF-treated CAMs, in which the angiogenesis index is plotted against exposure to either LM609 or P1F6 along with no antibody exposure as a control. Thus, inhibition of growth factor-induced angiogenesis by integrin-specific antibodies is dependent upon the type of growth factor.

Figure 5A:
FIGS. 5A–5F photographically illustrate the effects of synthetic peptide treatment on the chick CAM preparation as described in Example 6. Angiogenesis is either induced with bFGF or VEGF followed by intravenous administration of phosphate buffered saline (PBS) as a control or with the synthetic cyclic peptides RGDfV (SEQ ID NO 4) or RADfV (SEQ ID NO 5). CAMs treated with bFGF are shown in FIGS. 5A, 5C and 5E while CAMs treated with VEGF are shown in FIGS. 5B, 5D and 5F. Control CAMs receiving intravenous injections of PBS are shown in FIGS. 5A and 5B. The RDGfV peptide was used to treat CAMs shown in FIGS. 5C and 5D while the RADfV peptide was used to treat CAMs in FIGS. 5E and 5F.
Figure 5B:
Figure 5C:
Figure 5D:
Figure 5E:
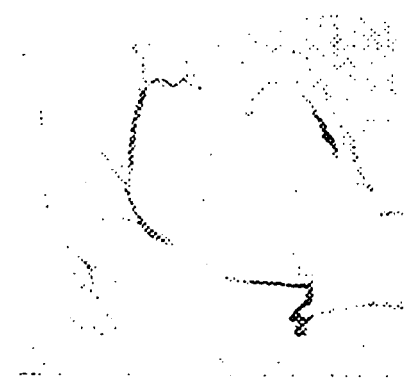
Figure 5F:
Figure 6A:
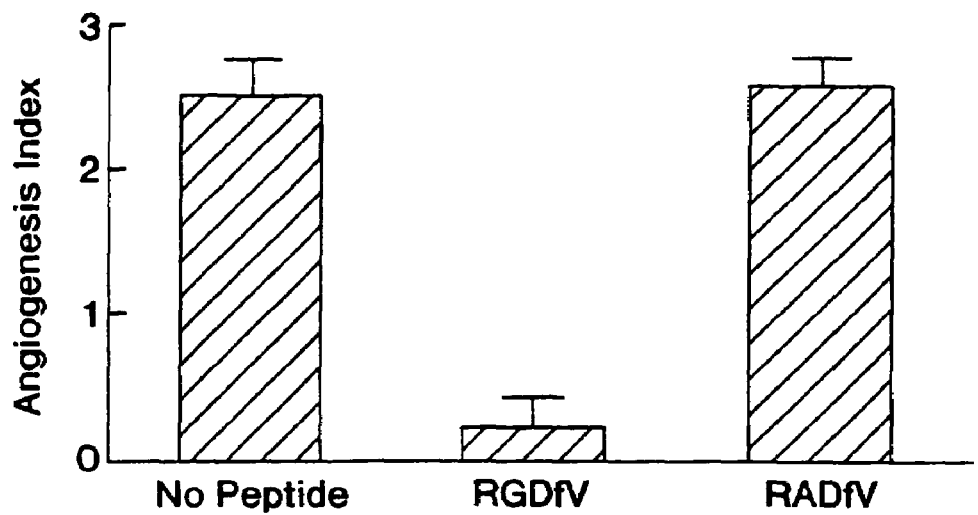
FIGS. 6A and 6B provide, in histogram format, the quantitation of results shown in FIGS. 5A–5F. The angiogenesis index is plotted on the Y-axis against control or antibody treatment.
Figure 6B:
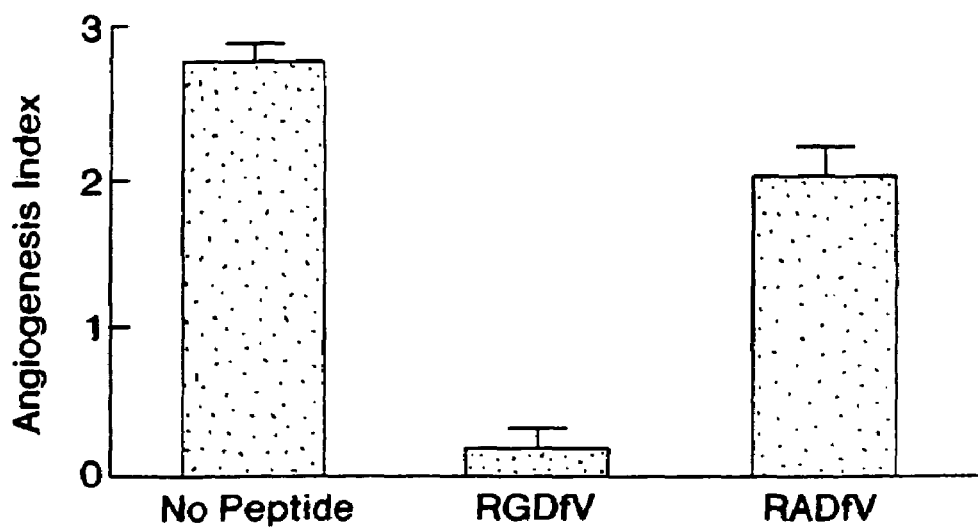

Exposure to RGD-containing peptides supports the above results. In the presence of PBS, as shown in FIGS. 5A and 5B, exposure to both bFGF and VEGF resulted in angiogenesis in the control CAM. In contrast, the cyclic peptide antagonist RGDfV (SEQ ID NO 4), directed to both $\alpha_v\beta_3$ and $\alpha_v\beta_5$, abolished angiogenesis induced by either bFGF or VEGF. The cyclic peptide RADfV (SEQ ID NO 5) did not effect angiogenesis in either the bFGF- or VEGF-treated CAM preparations. The results are also shown in FIGS. 6A and 6B where the angiogenesis index of bFGF- and VEGF-stimulated CAMS are graphed showing exposure to test and control peptides. Thus, these findings together with those in the rabbit corneas indicate that bFGF- and VEGF-induced angiogenesis depend on distinct but homologous $\alpha_v$-specific integrins that however are both inhibitable with the cyclic peptide RGDfV.

In a further assay performed in the CAM model having VEGF-induced angiogenesis, 2 μg of peptides 85189 (SEQ ID NO 9) and the inert salt counterpart 121974 were separately intravenously injected as previously described. The effect of the peptides was assessed in comparison to that of control peptide 69601 (SEQ ID NO 5) and to untreated (labeled as NT) preparations.

Figure 17:
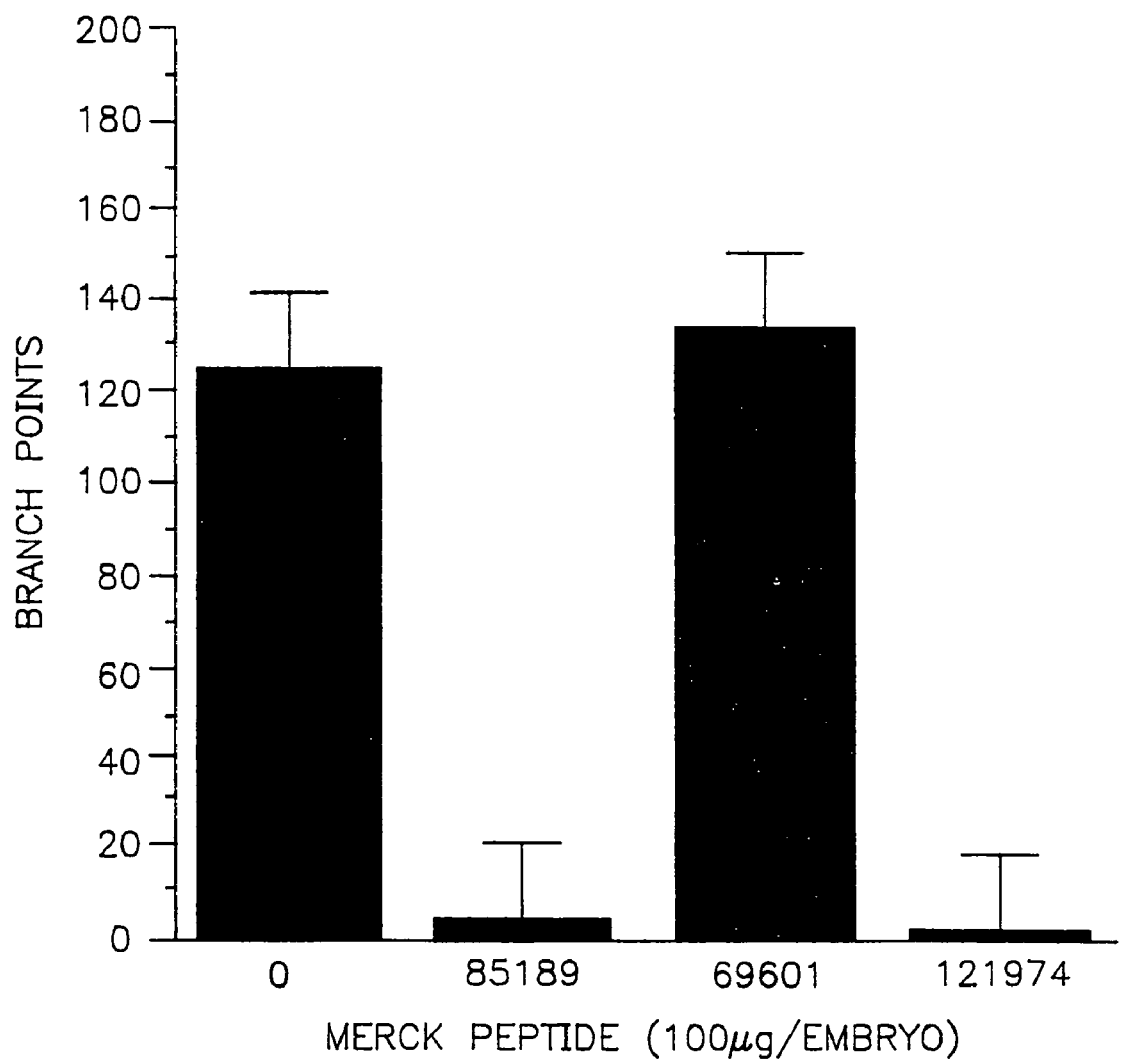
FIG. 17 shows the effects of peptides 85189 and inert salt counterpart 121974 on VEGF-induced angiogenesis in the CAM model as further described in Example 6A. The effect is compared to untreated (labeled as NT) and control (labeled as 69601) peptide treated preparations. The effect on angiogenesis is measured by calculation of the number of branch points as further described in Example 6A.

The effect of the peptides of VEGF-induced angiogenesis is measured through a determination of the number of blood vessel branch points. Thus, angiogenesis or the lack thereof was quantified by counting the number of blood vessels branch points that occur within the confines of the filter discs. The branched blood vessels are considered to correspond primarily to new angiogenic sprouting blood vessels. Quantification was performed in a double blind manner by at least two independent observers. The results are expressed as the Angiogenic Index where the angiogenic index is the number of branch points (VEGF stimulated) minus the number of branch points (control unstimulated) per filter disc. Experiments routinely had 6–10 embryos per condition. As shown in FIG. 17, both peptides 85189 and 121974 completely inhibited angiogenesis as indicated by a reduction of the measurable branch points in comparison to untreated or control peptide-treated preparations.

Additional similar assays are performed with synthetic peptides prepared as described in Example 3 to define peptides that exhibit specificity to $\alpha_v\beta_5$ and not $\alpha_v\beta_3$ correlated angiogenesis. Assays are also performed with the MMP-2 C-terminal fragments prepared as described in Example 3 and 7 and with the organic molecules prepared as described in Example 10.

The specificity of integrin antibody-inhibition of growth factor-induced angiogenesis was further confirmed and strengthened by extending the growth factor angiogenesis induction analyses to include tumor necrosis factor-α (TNF-α), transforming growth factor-α (TGF-α) or the phorbol ester, 4-β-phorbol-12-myristate-13-acetate (PMA).

The above growth factors (cytokines), including bFGF and VEGF, were separately applied at a concentration of 1.0 μg/ml to the 10 day old CAM model as previously described. PMA was used at a concentration of 20 ng/ml.

After 24 hours after growth factor treatment, the antibodies, LM609 and P1F6, or the protein kinase C (PKC) inhibitor, calphostin C, were separately provided to the CAM model, either by a single intravascular dose as described above or by topical administration as described below in the next example. For intravascular injections over the next 3 day consecutive period, the antibodies were used at a concentration of 75 μg per embryo and the calphostin C was at a dosage of 100 nM.

On day 13, filter discs and associated CAM tissue were dissected and analyzed for angiogenesis with a stereo microscope. Angiogenesis was scored in a double blind manner by analyzing the number and extent of branching of the blood vessels within the area of the discs. The scores ranged from low (1) to high (4). The angiogenesis index was determined by subtracting a background score of 1 from all data. Experiments were repeated 2–4 times with 5–6 embryos per condition.

Figure 7A:
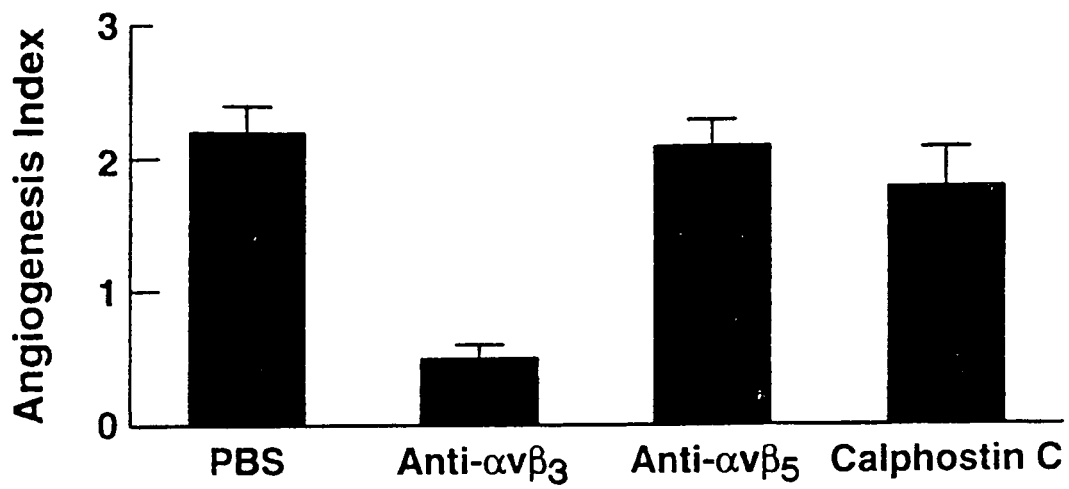
FIGS. 7A–7E show the effects of anti-integrin monoclonal antibodies and calphostin C on CAM angiogenesis induced by the separate cytokines, bFGF, TNF-$\alpha$, VEGF and TGF-$\alpha$. PMA was also evaluated. The assays and results are described in Example 6. The results are plotted in histogram format where angiogenesis index is graphed on the Y-axis and the various control or inhibitors are shown on the X-axis.
Figure 7B:
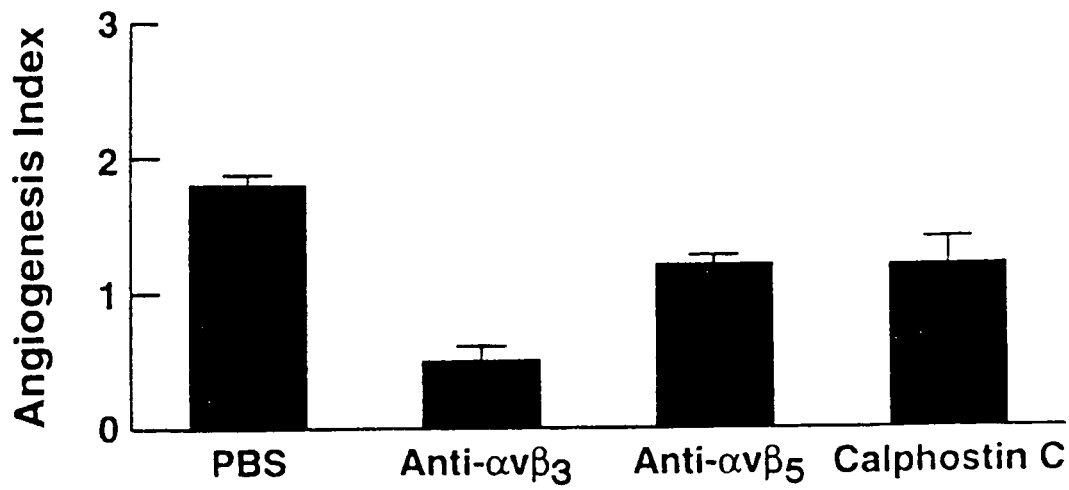
Figure 7C:
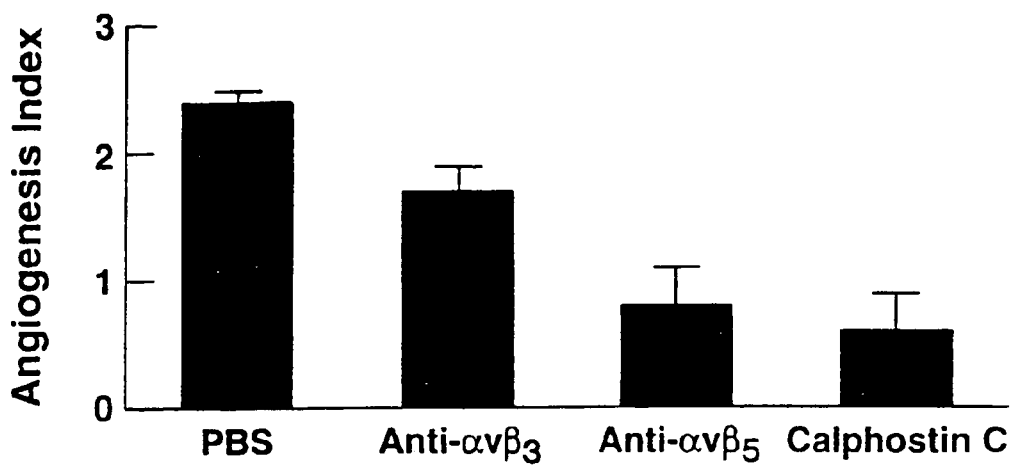
Figure 7D:
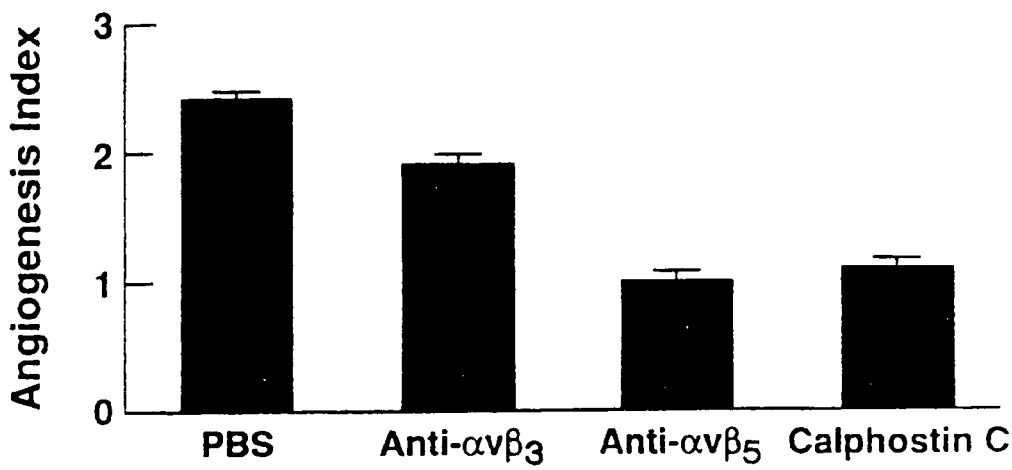
Figure 7E:
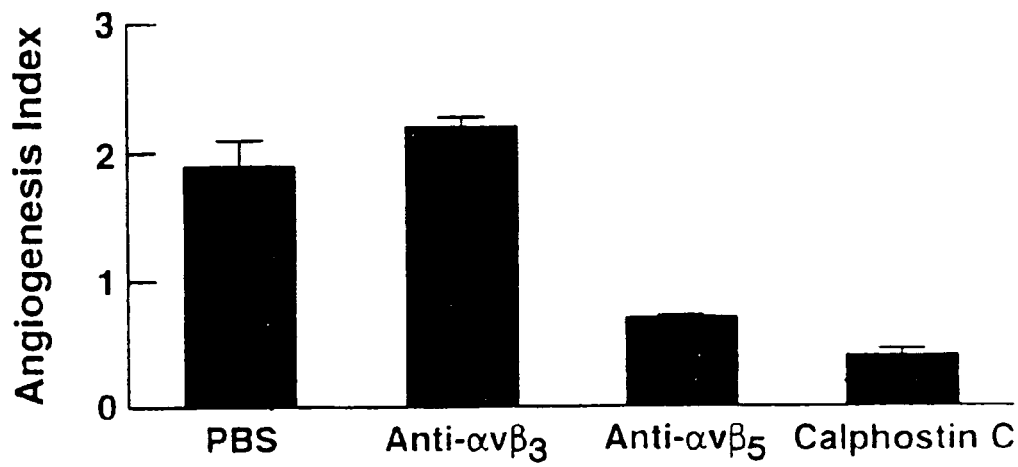

As shown respectively in FIGS. 7A and 7B, the anti-$\alpha_v\beta_3$ antibody, LM609, blocked angiogenesis in response to bFGF and TNF-α whereas the anti-$\alpha_v\beta_5$ antibody, P1F6, had little inhibitory effect. In contrast, as shown respectively in FIGS. 7C–7E, P1F6 was effective at inhibiting angiogenesis induced by VEGF, TGF-α, or PMA whereas LM609 failed to do so.

PMA, a potent inducer of angiogenesis, is capable of activating protein kinase C (PKC), an intracellular family of serine threonine kinases. Therefore, we also examined the effects of calphostin C, a PKC inhibitor, or angiogenesis on the chick CAM. Calphostin C blocked angiogenesis induced by PMA (FIG. 7E) as well as VEGF and TGF-α (respectively shown in FIGS. 7C and 7D) while having minimal effects on bFGF- or TNF-α mediated angiogenesis (respectively shown in FIGS. 7A and 7B).

Together, these results indicate the existence of two separate distinct angiogenesis pathways where one is dependent upon an $\alpha_v\beta_3$-mediated signal that is largely independent of PKC, as previously described by Brooks et al., *Science*, 264:569–571 (1994), and a second pathway is potentiated by an $\alpha_v\beta_5$-mediated transduction signal that critically depends of PKC activation.

In addition to the above experiments, to determine the localization of the P1F6 and LM609 mAbs in CAM tissues that were inoculated intravenously with LM609, the fixed sections are blocked with 2.5% BSA in HBSS for 1 hour at room temperature followed by staining with a 1:250 dilution of goat anti-mouse rhodamine labeled secondary antibody (Tago). The sections are then analyzed with a Zeiss immunofluorescence compound microscope.

B. Inhibition of Growth Factor-Induced Angiogenesis by Topical Application of Inhibitors To determine whether $\alpha_v\beta_5$ plays an active role in angiogenesis, filter disks saturated with growth factors described above are placed on CAMs to induce angiogenesis followed by application of either P1F6 or LM609.

Disks are then treated with 50 ml HBSS containing 25 mg of mAb in a total volume of 25 μl of sterile HBSS at 0, 24, and 48 hours. At 72 hours, CAMs are harvested and placed in a 35 mm petri dish and washed once with 1 ml of PBS. The bottom side of the filter paper and CAM tissue is then analyzed under an Olympus stereo microscope, with two observers in a double-blind fashion. Angiogenesis inhibition is considered significant when CAMs exhibits >50% reduction in blood vessel infiltration of the CAM directly under the disk. Experiments are repeated four times per antibody, with 6 to 7 embryos per condition.

To examine the effects of the integrin antibodies on preexisting mature blood vessels present from normal vessel development adjacent to the areas devoid of vessels, filter disks saturated with mAbs are placed on vascularized regions of CAMs from 10 day embryos that do not receive topical application of cytokine.

CAM assays are also performed with the synthetic peptides of this invention to determine the effect of cyclic and linearized peptides on growth factor induced angiogenesis. Eight μg of peptides, prepared as previously described, are separately presented in a total volume of 25 μl of sterile HBSS. The peptide solution is applied to the CAM preparation immediately and then again at 24 and 48 hrs. At 72 hours the filter paper and surrounding CAM tissue are dissected and viewed as described above.

Similar assays are performed with the MMP-2 fragments and organic molecules prepared as respectively described in Examples 7 and 10.

C. Inhibition of Tumor-Induced Angiogenesis by Topical Application

1) Treatment with Monoclonal Antibodies

In addition to the angiogenesis assays described above where the effects of anti-$\alpha_v\beta_5$ antibody and peptide antagonists were evaluated, the role of $\alpha_v\beta_5$ in tumor-induced angiogenesis is also investigated. As an inducer, $\alpha_v\beta_5$- negative human tissues previously grown and isolated from the CAM of a 17-day chick embryo are used. The fragments are prepared as described in Example 5C.

As described above, mAbs are separately topically applied to the tumor fragments at a concentration of 25 µg in 25 µl of HBSS and the windows are then sealed with tape. The mAbs are added again in the same fashion at 24 hours and 48 hours. At 72 hours, the tumors and surrounding CAM tissues are analyzed as described above.

As described in Example 5C, tumors are initially derived by transplanting human cell lines, which do not express integrin $\alpha_v\beta_5$, onto the CAMs of 10 day old chick embryos.

In order to quantitate the effect of the mAbs on the tumor-induced angiogenesis, blood vessels entering the tumor within the focal plane of the CAM are counted under a stereo microscope by two observers in a double-blind fashion.

The synthetic peptides prepared in Example 3, the MMP-2 preparations described in Example 7 and the organic molecules prepared in Example 10 are similarly topically applied to the tumor-induced angiogenic CAM assay system as described above. The effect of the peptides including the MMP-2 preparations and organic molecules described in this invention on the viability of the vessels is similarly assessed.

D. Inhibition of Tumor-Induced Angiogenesis by Intravenous Application

1) Treatment with Monoclonal Antibodies

Tumor-induced blood vessels prepared above were also treated with mAbs applied by intravenous injection. CS-1 melanoma tumors were placed on the CAMs as described in Example 5C and the windows were sealed with tape and 24 hours later, 100 to 300 µg of purified mAbs were inoculated once intravenously in chick embryo blood vessels as described previously. The chick embryos were then allowed to incubate for 7 days. The extent of angiogenesis was then observed as described in above. After this time period, the tumors were resected and analyzed by their weight to determine the effect of antibody exposure on tumor growth or suppression.

Figure 8:
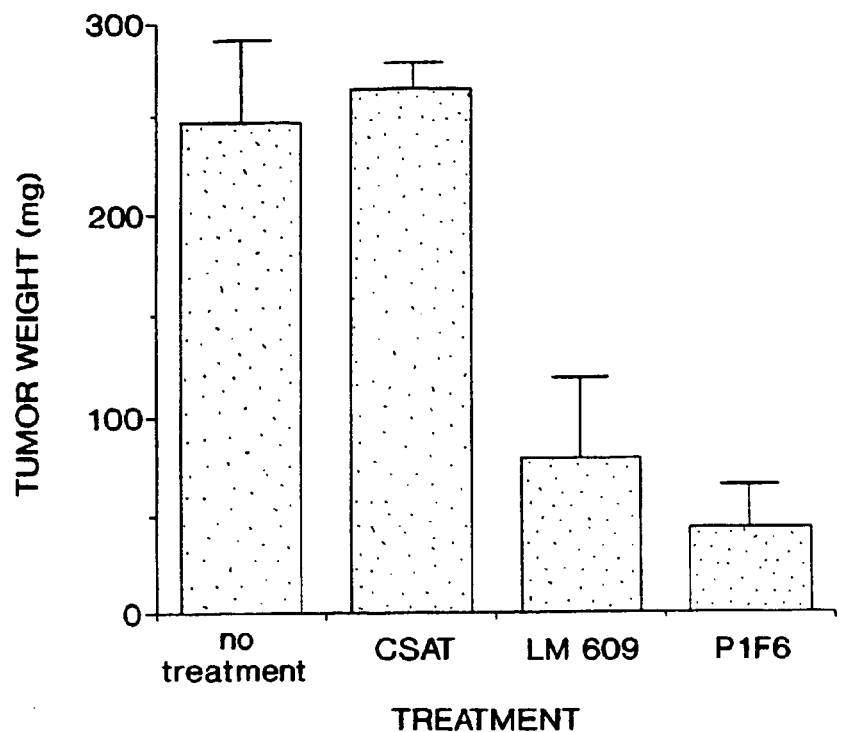
FIG. 8 is a histogram showing the effects of antibody treatment on CS1 melanoma tumor growth in the chick embryo CAM assayed performed as described in Examples 5C and 6D. The weight of the tumors in milligrams (mg) is plotted on the Y-axis against the various treatments indicated on X-axis. CSAT is a control antibody specific for the integrin $\beta_1$ subunit. LM609 and P1F6 are previously described.

The results of treatment of CS-1 tumors with 300 µg of $\alpha_v\beta_5$ specific antibody P1F6 are shown in FIG. 8. The tumor weight was dramatically reduced to less than 50 mg as compared to untreated to CSAT-treated tumors. The $\alpha_v\beta_5$ specific antibody, LM609, also inhibited tumor growth, however, less effective than that with P1F6. Comparable results were obtained with tumors receiving treatment with 100 µg of P1F6. Thus, P1F6 was effective at inhibiting $\alpha_v\beta_5$-mediated angiogenesis in a tumor model on a CAM preparation resulting in a diminution of tumor cell mass.

2) Treatment with Other $\alpha_v\beta_5$ Antagonists

The effects of peptides, MMP-2 preparations or organic molecules on tumor-induced vasculature in the CAM assay system are also assessed. The tumor-CAM preparation is used as described above with the exception that instead of intravenous injection of a mAb, synthetic peptides including MMP-2 preparations prepared as described in Example 7 and organic molecules prepared in Example 10 are separately intravenously injected into visible blood vessels.

In one particular set of assays, additional tumor regression assays were performed with the $\alpha_v\beta_5$-reactive peptide 85189 (SEQ ID NO 9) against 69601 (SEQ ID NO 5) as a control. The assays were performed as described above with the exception that 100 ug of peptide was intravenously injected into the CAM at 18 hourst postimplantation of the various tumors which in this case included UCLAP-3, M21-L and FgM tumor types. After 48 hours more, the tumors were then resected and wet weights were obtained.

Figure 18:
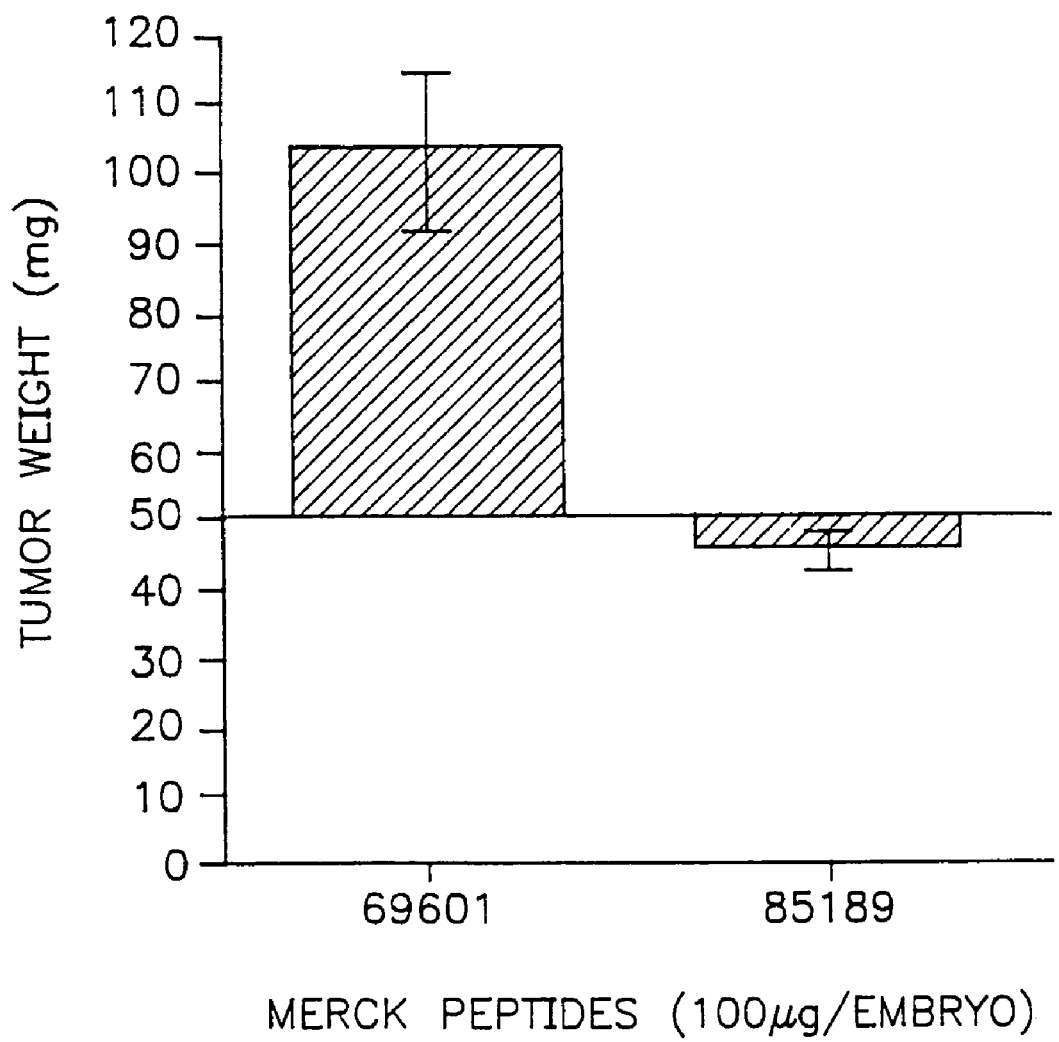
FIGS. 18, 19 and 20 respectively show the reduction in tumor weight for UCLAP-3, M21-L, and FgM tumors following intravenous exposure to control peptide 69601 and antagonist 85189 as further described in Example 6D. The data is plotted with tumor weight on the Y-axis against the peptide treatments on the X-axis.
Figure 19:
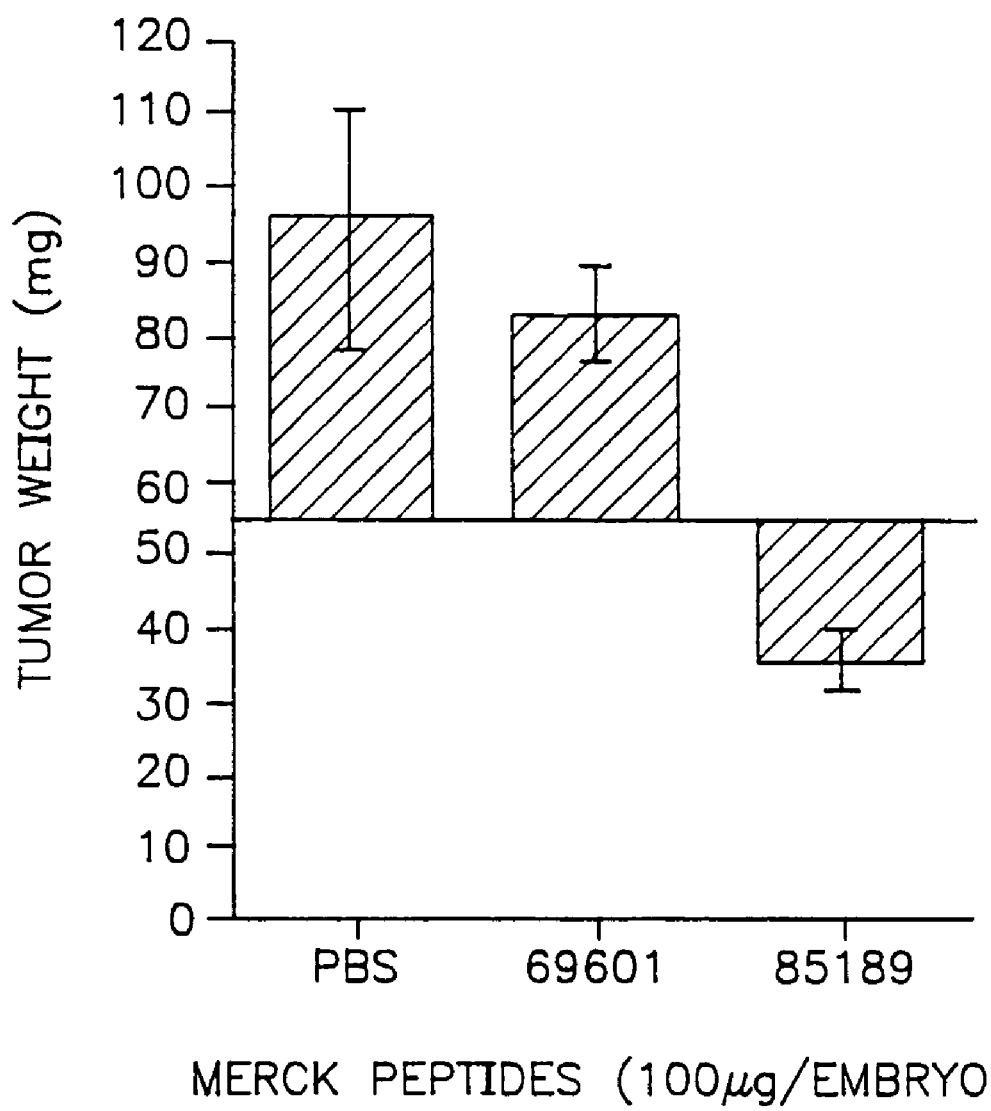
Figure 20:
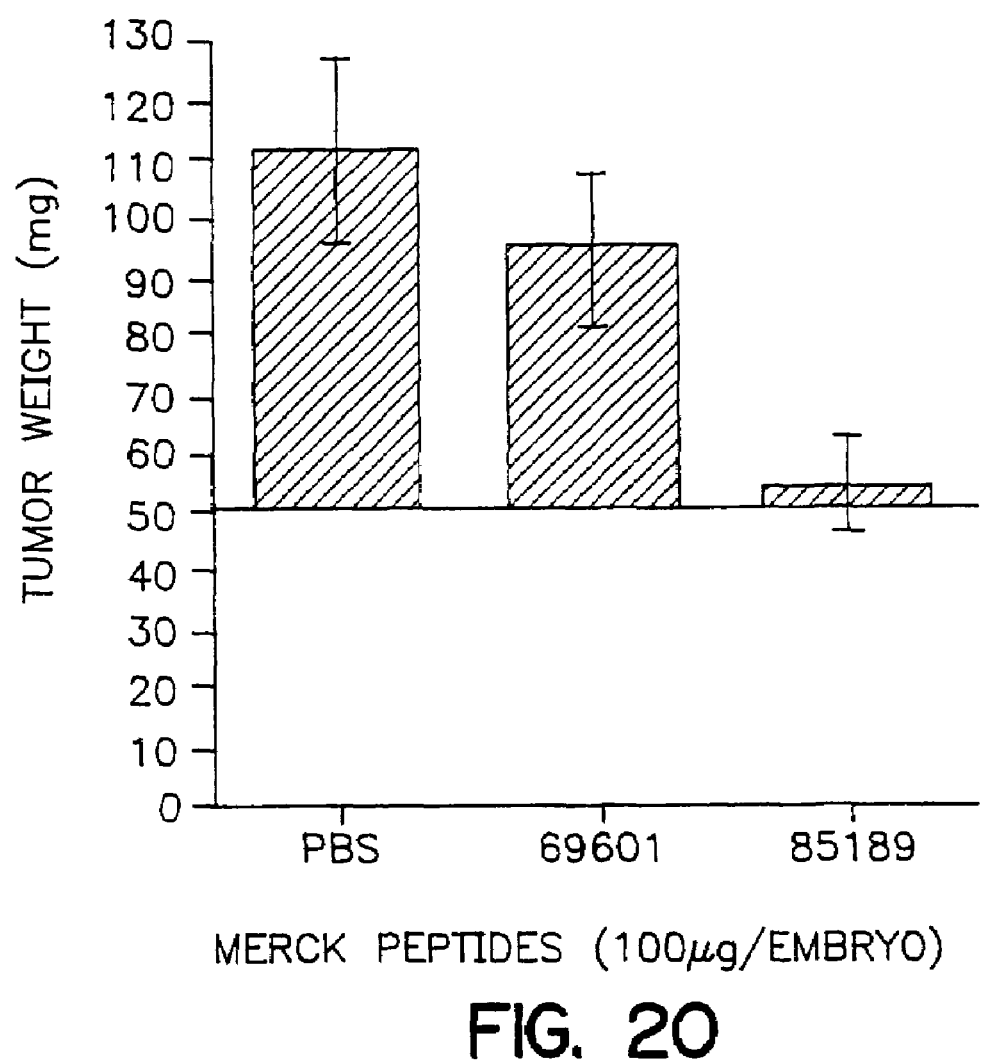

FIGS. 18, 19 and 20 respectively show the reduction in tumor weight for UCLAP-3, M21-L and FgM tumors following intravenous exposure to peptide 85189 in contrast to the lack of effect with either PBS or peptide 69601.

7. Identification of $\alpha_v\beta_5$-Specific Antagonists Detected by Inhibition of Cell Attachment and by a Ligand-Receptor Binding Assay A. Inhibition of Cell Attachment As one means to determine integrin receptor specificity of the antagonists of this invention, inhibition of cell attachment assays are performed as described below.

Briefly, CS-1 hamster melanoma cells lacking expression of $\alpha_v\beta_3$ and $\alpha_v\beta_5$ are first transfected with an plasmid for expressing the $\beta_5$ subunit as previously described by Filardo et al., *J. Cell Biol.*, 130:441–450 (1995). Specificity of potential $\alpha_v\beta_5$ antagonists was determined by the ability to block the binding of $\alpha_v\beta_5$-expressing CS-1 cells to VN or laminin coated plates. As an example of a typical assay, the wells were first coated with 10 ug/ml substrate overnight. After rinsing and blocking with 1% heat-denatured BSA in PBS at room temperature for 30 minutes, peptide 85189 (SEQ ID NO 9) over a concentration range of 0.0001 uM to 100 uM, are separately mixed with CS-1 cells for applying to wells with a cell number of 50,000 cells/well. After a 10–15 minute incubation at 37C, the solution containing the cells and peptides is discarded. The number of attached cells is then determined following staining with 1% crystal violet. Cell associated crystal violet is eluted by the addition of 100 microliters (µl) of 10% acetic acid. Cell adhesion was quantified by measuring the optical density of the eluted crystal violet at a wave length of 600 nm.

Similar assays are performed with fusion proteins or the synthetic peptide counterparts containing various regions of the MMP-2 protein. The MMP-2-derived polypeptides include regions of the C-terminus of MMP-2 active in the binding interaction with $\alpha_v\beta_5$ and thereby capable of inhibiting MMP-2 activation and associated activities. These polypeptides are prepared either as synthetic polypeptides having a sequence derived from the C-terminal domain of MMP-2 as described in Example 1 or as fusion proteins including all or a portion of the C-terminal domain of MMP-2, prepared as described below. MMP-2 C-terminal molecules are presented for both chicken and human specific sequences.

The chicken-derived MMP-2 C-terminal domain, also referred to as the hemopexin domain immediately contiguous with the hinge region, comprises the amino acid residues 445–637 of MMP-2. The complete nucleotide and encoded amino acid sequence of chicken MMP-2 is described below and is shown in FIGS. 15A–15D, with the nucleotide and amino acid sequences respectively listed as SEQ ID NOs 23 and 24. The human MMP-2 nucleotide and encoded amino acid sequence is also described below, with the latter shown in FIG. 16 and SEQ ID NO 25. The C-terminal domain in the human MMP-2 that corresponds to the chicken region of 445–637 begin at amino acid residue 439 and ends with 631 due to six missing residues from the human sequence as shown in FIG. 15C. Both human- and chicken-derived C-terminal MMP-2 synthetic peptides for use in practicing the methods of this invention are listed in Table 1. The amino acid residue sequences of the synthetic peptides are the same as those generated by the recombinant fusion protein counterparts but without the GST fusion component. The C-terminal MMP-2 fusion proteins derived from both chicken and human are prepared as described below.

A MMP-2 fusion protein is a chimeric polypeptide having a sequence of MMP-2 C-terminal domain or a portion thereof fused (operatively linked by covalent peptide bond) to a carrier (fusion) protein, such as glutathione sulfhydryl transferase (GST).

To amplify various regions of chicken and human MMP-2, primer sequences were designed based on the known respective cDNA sequences of chicken and human MMP-2. The complete top strand of the cDNA nucleotide sequence of unprocessed chicken MMP-2, also referred to as progelatinase, is shown in FIGS. 15A–15D along with the deduced amino acid sequence shown on the second line (Aimes et al., *Biochem. J.,* 300:729–736, 1994). The third and fourth lines of the figure respectively show the deduced amino acid sequence of human (Collier et al., *J. Biol. Chem.,* 263:6579–6587 (1988)) and mouse MMP-2 (Reponen et al., *J. Biol. Chem.,* 267:7856–7862 (1992)). Identical residues are indicated by dots while the differing residues are given by their one letter IUPAC lettering. Missing residues are indicated by a dash. The numbering of the amino acid residues starts from the first residue of the proenzyme, with the residues of the signal peptide being given negative numbers. The nucleotide sequence is numbered accordingly in the figure although in the Sequence Listing, the first nucleotide is listed as number 1. The putative initiation of translation (ATG) is marked with three forward arrowheads and the translation termination signal (TGA) is indicated by an asterisk. The amino terminal sequences for the chicken proenzyme and active enzyme are contained with diamonds and single arrowheads. As previously stated, the chicken progelatinase nucleotide and amino acid residue sequences are listed together as SEQ ID NO 23 while the encoded amino acid residue sequence is listed separately as SEQ ID NO 24.

Templates for generating amplified regions of chicken MMP-2 were either a cDNA encoding the full-length mature chicken MMP-2 polypeptide provided by Dr. J. P. Quigley of the State University of New York at Stoney Brook, N.Y. or a cDNA generated from a total cellular RNA template derived by standard techniques from an excised sample of chicken chorioallantoic membrane tissue. For the latter, the cDNA was obtained with MuLV reverse transcriptase and a downstream primer specific for the 3'-terminal nucleotides. 5'ATTGAATTCTTCTACAGTTCA3' (SEQ ID NO 26), the 5' and 3' ends of which was respectively complementary to nucleotides 1932–1912 of the published chick MMP-2 sequence. As described in the FIG. 15 figure legend, the nucleotide positions of the primers described herein correspond to those shown in the figure and not as shown in the Sequence Listing as the latter begins with number 1 and not as a negative number as indicated in the figure. Reverse transcriptase polymerase chain reaction (RT-PCR) was performed according to the specifications of the manufacturer for the GeneAmp RNA PCR Kit (Perkin Elmer). The primer was also engineered to contain an internal EcoRI restriction site.

From either of the above-described cDNA templates, a number of C-terminal regions of chicken MMP-2, each having the natural cysteine residue at position 637 at the carboxy terminus, were obtained by PCR with the 3' primer listed above (SEQ ID NO 26) paired with one of a number of 5' primers listed below. The amplified regions encoded the following MMP-2 fusion proteins, having sequences corresponding to the amino acid residue positions as shown in FIGS. 15B and 15C and also listed in SEQ ID NO 24: 1) 203–637; 2) 274–637; 3) 292–637; 4) 410–637; 5) 445–637. Upstream or 5' primers for amplifying each of the nucleotide regions for encoding the above-listed MMP-2 fusion proteins were designed to encode the polypeptide start sites 3' to an engineered, i.e., PCR-introduced, internal BamHI restriction site to allow for directional ligation into either pGEX-1λT or pGEX-3X expression vectors. The 5' primers included the following sequences, the 5' and 3' ends of which correspond to the indicated 5' and 3' nucleotide positions of the chicken MMP-2 sequence shown in the figure (the amino acid residue position start sites are also indicated for each primer): 1) Nucleotides 599–619, encoding a 203 start site 5'ATGGGATCCACTGCAAATTTC3' (SEQ ID NO 27); 2) Nucleotides 809–830, encoding a 274 start site 5'GCCGGATCCATGACCAGTGTA3' (SEQ ID NO 28); 3) Nucleotides 863–883, encoding a 292 start site 5'GTGGGATCCCTGAAGACTATG3' (SEQ ID NO 29); 4) Nucleotides 1217–1237, encoding a 410 start 5'AGGGGATCCTTAAGGGGATTC3' (SEQ ID NO 30); and 5) Nucleotides 1325–1345, encoding a 445 start site 5'CTCGGATCCTCTGCAAGCACG3' (SEQ ID NO 31).

The indicated nucleotide regions of the template cDNA were subsequently amplified for 35 cycles (annealing temperature 55C) according to the manufacturer's instructions for the Expand High Fidelity PCR System (Boehringer Mannheim). The resulting PCR products were gel-purified, digested with BamHI and EcoRI restriction enzymes, and repurified before ligation into either pGEX-1λT or pGEX-3X vector (Pharmacia Biotech, Uppsala, Sweden) which had been similarly digested as well as dephosphorylated prior to the ligation reaction. The choice of plasmid was based upon the required reading frame of the amplification product. Competent *E. coli* strain BSJ72 or BL21 cells were transformed with the separate constructs by heat shock. The resulting colonies were screened for incorporation of the respective MMP-2 fusion protein-encoding plasmid by PCR prior to dideoxy sequencing of positive clones to verify the integrity of the introduced coding sequence. In addition, verification of incorporation of plasmid was confirmed by expression of the appropriately-sized GST-MMP-2 fusion protein.

Purification of each of the recombinant GST-MMP-2 fusion proteins was performed using IPTG-induced log-phase cultures essentially as described by the manufacturer for the GST Gene Fusion System (Pharmacia Biotech). Briefly, recovered bacteria were lysed by sonication and incubated with detergent prior to clarification and immobilization of the recombinant protein on sepharose 4B-coupled glutathione (Pharmacia Biotech). After extensive washing, the immobilized fusion proteins were separately eluted from the affinity matrix with 10 mM reduced glutathione in 50 mM Tris-HCl, pH 8.0, and dialyzed extensively against PBS to remove residual glutathione prior to use.

Prior attempts to produce fusion proteins between chicken MMP-2 residues 445 and 637 that only had one encoded cysteine residue resulted in insoluble products. Therefore, in order to generate additional soluble MMP-2 fusion proteins derived from the C-terminal region that did not include an endogenous terminal cysteine residue as present in the previously-described fusion protein, nucleotide sequences were introduced into amplified MMP-2 regions to encode a cysteine residue if necessary depending on the particular fusion protein. A cysteine residue is naturally present in the chicken MMP-2 sequence at position 446 and at position 637. In the human sequence, these positions correspond respectively to 440 and 631. Therefore, fusion proteins were designed to contain engineered terminal cysteine residues at the amino- or carboxy-terminus of the chicken MMP-2 sequences of interest so as to provide for disulfide-bonding with the naturally occurring cysteine at the other terminus, as required by the construct. Synthetic MMP-2 fragments for both chicken and human are similarly prepared as previously described in Example 3.

Oligonucleotide primers were accordingly designed to allow for amplification of chicken MMP-2 C-terminal regions for expression of soluble MMP-2/GST fusion proteins. Amplified chicken MMP-2 C-terminal regions included those for encoding amino acid residue positions 445–518, 445–552, 516–637 and 549–637. For fusion proteins containing residue 517, the naturally encoded tyrosine residue was substituted for a cysteine to allow for disulfide bonding with either cysteine at residue position 446 or 637. For fusion proteins containing residue 551, the naturally encoded tryptophan residue was substituted for a cysteine to allow for disulfide bonding with either naturally encoded cysteine at residue position 446 or 637.

Briefly, the pGEX-3X plasmid construct encoding the recombinant GST/MMP-2(410–637) fusion protein prepared above was used as a template for amplification according to the manufacturer's protocol for the Expand High Fidelity PCR Kit (Boehringer Mannheim) utilizing a set of oligonucleotide primers whose design was based on the published chicken MMP-2 sequence (also shown in FIGS. 15A–15D and in SEQ ID NO 23). One upstream primer, designed to encode a chicken MMP-2 protein start site at position 445 after an engineered internal BamHI endonuclease restriction site for insertion into the pGEX-3X GST vector, had the nucleotide sequence (5'CTCGGATCCTCT-GCAAGCACG3' (SEQ ID NO 32)). The 5' and 3' ends of the primer respectively corresponded to positions 1325–1345 of the chicken MMP-2 sequence in FIG. 15C. Another upstream primer, designed to encode a chicken MMP-2 protein start site at position 516 after an engineered internal BamHI restriction site for insertion into the pGEX-1λT GST vector and to encode a cysteine residue at position 517, had the nucleotide sequence (5'GCAGGATCCGAGT-GCTGGGTTTATAC3' (SEQ ID NO 33)). The 5' and 3' ends of the primer respectively corresponded to positions 1537–1562 of the chicken MMP-2 sequence in the figure. A third upstream primer, designed to encode a chicken MMP-2 protein start site at position 549 following an engineered internal EcoRI endonuclease restriction site for insertion into the pGEX-1λT GST vector and to encode a cysteine residue at position 551, had the nucleotide sequence (5'GCAGAATTCAACTGTGGCAGAAACAAG3' (SEQ ID NO 34)). The 5' and 3' ends of the primer respectively corresponded to positions 1639–1665 of the chicken MMP-2 sequence in the figure.

These upstream primers were separately used with one of the following downstream primers listed below to produce the above-described regions from the C-terminal domain of chicken MMP-2. A first downstream primer (antisense), designed to encode a chicken MMP-2 protein termination site at position 518, to encode a cysteine residue at position 517, and to contain an internal EcoRI endonuclease restriction site for insertion into a GST vector, had the nucleotide sequence (5'GTAGAATTCCAGCACTCATTTCCTGC3' (SEQ ID NO 35)). The 5' and 3' ends of the primer, written in the 5'-3' direction, were respectively complementary in part to positions 1562–1537 of the chicken MMP-2 sequence in the figure. A second downstream primer, designed to encode a chicken MMP-2 protein termination site at position 552, to encode a cysteine residue at position 551, and to contain an internal EcoRI endonuclease restric-tion site for insertion into a GST vector, had the nucleotide sequence (5'TCTGAATTCTGCCACAGTTGAAGG3' (SEQ ID NO 36)). The 5' and 3' ends of the primer, written in the 5'-3' direction, were respectively complementary in part to positions 1666–1643 of the chicken MMP-2 sequence in the figure. A third downstream primer, designed to encode a chicken MMP-2 protein termination site at position 637 and to contain an internal EcoRI endonuclease restriction site for insertion into a GST vector, had the nucleotide sequence (5'ATTGAATTCTTCTACAGTTCA3' (SEQ ID NO 37)). The 5' and 3' ends of the primer, written in the 5'-3' direction, were respectively complementary in part to positions 1932–1912 of the chicken MMP-2 sequence in the figure.

The regions of the chicken MMP-2 carboxy terminus bonded by the above upstream and downstream primers, used in particular combinations to produce the fusion proteins containing at least one engineered cysteine residue as described above, were separately amplified for 30 cycles with an annealing temperature of 55C according to the manufacturer's instructions for the Expand High Fidelity PCR System (Boehringer Mannheim). The resulting amplification products were separately purified, digested with BamHI and or EcoRI restriction enzymes as necessary, and repurified before ligation into the appropriate GST fusion protein vector, either pGEX-3X or pGEX-1λT, as indicated above by the reading frame of the upstream oligonucleotide primer. For ligating the amplified MMP-2 products, the vectors were similarly digested as well as dephosphorylated prior to the ligation reaction. Competent *E. coli* strain BL21 cells were then separately transformed with the resultant MMP-2-containing vector constructs by heat shock. Resulting colonies were then screened for incorporation of the appropriate fusion protein-encoding plasmid by PCR and production of the appropriate sized GST-fusion protein prior to dideoxy sequencing of positive clones to verify the integrity of the introduced coding sequence. Purification of recombinant GST fusion proteins were the performed using IPTG-induced log-phase cultures essentially as described above for producing the other GST-MMP-2 fusion proteins.

In addition to the chicken MMP-2 GST-fusion proteins described above, two human MMP-2 GST fusion proteins were produced for expressing amino acid regions 203–631 and 439–631 of the mature human MMP-2 proenzyme polypeptide. The indicated regions correspond respectively to chicken MMP-2 regions 203–637 and 445–637. Human MMP-2-GST fusion proteins were produced by PCR as described above for the chicken MMP-2-GST fusion proteins utilizing a cDNA template that encoded the entire human MMP-2 open reading frame provided by Dr. W. G. Stetler-Stevenson at the National Cancer Institute, Bethesda, Md. Upstream 5' primer sequences were designed based upon the previously published sequence of human MMP-2 (Collier et al., *J. Biol. Chem.*, 263:6579–6587 (1988)) and to encode an introduced internal EcoRI restriction site to allow for insertion of the amplified products into the appropriate expression vector.

One upstream primer, designed to encode a human MMP-2 protein start site at position 203 after an engineered internal EcoRI endonuclease restriction site for insertion into the pGEX-1λT GST vector, had the nucleotide sequence (5'GATGAATTCTACTGCAAGTT3' (SEQ ID NO 38)). The 5' and 3' ends of the primer respectively corresponded to positions 685–704 of the human MMP-2 open reading frame sequence. Another upstream primer, designed to encode a human MMP-2 protein start site at position 439 after an engineered internal EcoRI restriction site for insertion into the pGEX-1λT GST vector, had the nucleotide sequence (5'CACTGAATTCATCTGCAAACA3' (SEQ ID NO 39)). The 5' and 3' ends of the primer respectively corresponded to positions 1392 and 1412 of the human MMP-2 open reading frame sequence.

Each of the above primers were used separately with a downstream primer, having 5' and 3' ends respectively complementary to bases 1998 and 1978 of the human MMP-2 sequence that ends distal to the MMP-2 open reading frame and directs protein termination after amino acid residue 631. The amplified products produced expressed fusion proteins containing human MMP-2 amino acid residues 203–631 (SEQ ID NO 40) and 439–631 (SEQ ID NO 12).

The resulting PCR products were purified, digested with EcoRI and repurified for ligation into a pGEX-1λT plasmid that was similarly digested and dephosphorylated prior to the ligation reaction. Cells were transformed as described above.

Other human MMP-2 fusion proteins containing amino acid residues 410–631 (SEQ ID NO 11), 439–512 (SEQ ID NO 13), 439–546 (SEQ ID NO 14), 510–631 (SEQ ID NO 15) and 543–631 (SEQ ID NO 16) are also prepared as described above for use in the methods of this invention.

B. Ligand-Receptor Binding Assay

The $\alpha_v\beta_5$-immunoreactive antibodies and synthetic peptides prepared respectively in Examples 1 and 3 are screened by measuring their ability to antagonize $\alpha_v\beta_5$, $\alpha_v\beta_3$, and $\alpha_{IIb}\beta_3$ receptor binding activity in purified ligand-receptor binding assays. The method for these binding studies has been described by Barbas et al., *Proc. Natl. Acad. Sci., USA*, 90:10003–10007 (1993), Smith et al., *J. Biol. Chem.*, 265: 11008–11013 (1990) and Pfaff et al., *J. Biol. Chem.*, 269: 20233–20238 (1994), the disclosures of which are hereby incorporated by reference.

A method of identifying antagonists in a ligand-receptor binding assay is described in which the receptor is immobilized to a solid support and the ligand and antagonist are soluble. A ligand-receptor binding assay is also described in which the ligand is immobilized to a solid support and the receptor and antagonists are soluble.

Briefly, selected purified integrins are separately immobilized in Titertek microtiter wells at a coating concentration of 50 nanograms (ng) per well. The purification of the receptors used in the ligand-receptor binding assays are well known in the art and are readily obtainable with methods familiar to one of ordinary skill in the art. After incubation for 18 hours at 4C, nonspecific binding sites on the plate are blocked with 10 milligrams/milliliter (mg/ml) of bovine serum albumin (BSA) in Tris-buffered saline. For inhibition studies, various concentrations of selected antibodies or peptides are tested for the ability to block the binding of $^{125}$I-vitronectin or other labeled ligands to the integrin receptors, $\alpha_v\beta_5$, $\alpha_v\beta_3$, $\alpha_v\beta_1$ and $\alpha_{IIb}\beta_3$.

Although these ligands exhibit optimal binding for a particular integrin, vitronectin for $\alpha_v\beta_5$ and $\alpha_v\beta_3$ and fibrinogen for $\alpha_{IIb}\beta_3$, inhibition of binding studies using either antibodies or peptides to block the binding of vitronectin to either receptor allows for the accurate determination of the amount in micromoles (μM) of peptide necessary to half-maximally inhibit the binding of receptor to ligand. Radiolabeled ligands are used at concentrations of 1 nM and binding is challenged separately with unlabeled synthetic peptides. Following a three hour incubation, free ligand is removed by washing and bound ligand is detected by gamma counting.

Thus, the ligand-receptor assay described herein is used to screen for both circular or linearized synthetic peptides along with monoclonal antibodies and organic molecules that exhibit selective specificity for a particular integrin receptor, specifically $\alpha_v\beta_5$, as used as vitronectin receptor ($\alpha_v\beta_5$) antagonists in practicing this invention.

8. In Vivo Regression of Tumor Tissue Growth With $\alpha_v\beta_5$ Antagonists as Measured by Chimeric Mouse:Human Assay An in vivo chimeric mouse:human model was generated by replacing a portion of skin from a SCID mouse with human neonatal foreskin. The in vivo chimeric mouse:human model was prepared essentially as described in Yan, et al., *J. Clin. Invest.*, 91:986–996 (1993). Briefly, a 2 cm² square area of skin was surgically removed from a SCID mouse (6–8 weeks of age) and replaced with a human foreskin. The mouse was anesthetized and the hair removed from a 5 cm² area on each side of the lateral abdominal region by shaving. Two circular graft beds of 2 cm² were prepared by removing the full thickness of skin down to the fascia. Full thickness human skin grafts of the same size derived from human neonatal foreskin were placed onto the wound beds and sutured into place. The graft was covered with a Band-Aid which was sutured to the skin. Micropore cloth tape was also applied to cover the wound.

After the skin graft was established, the human foreskin was inoculated with melanoma cells. The M21L human melanoma cell line was used to form the solid human tumors on the human skin grafts on the SCID mice. A single cell suspension of $2 \times 10^6$ M21L was injected intradermally into the human skin graft. The mice were then observed for 2 to 4 weeks to allow growth of measurable human tumors.

After a measurable tumor was established, either 250 μg of the peptide (in a volume of 100 μl) having SEQ ID NO 9 (cyclic RGD-containing peptide Arg-Gly-Asp-D-Phe-Asn-NMeVAL) or a control peptide, cyclo Arg-βAla-Asp-D-Phe-Val, were injected intraperitoneally into the mouse 3 times per week over 3 weeks. At the end of this time, the tumor was excised and analyzed by weight and histology.

Figure 9:
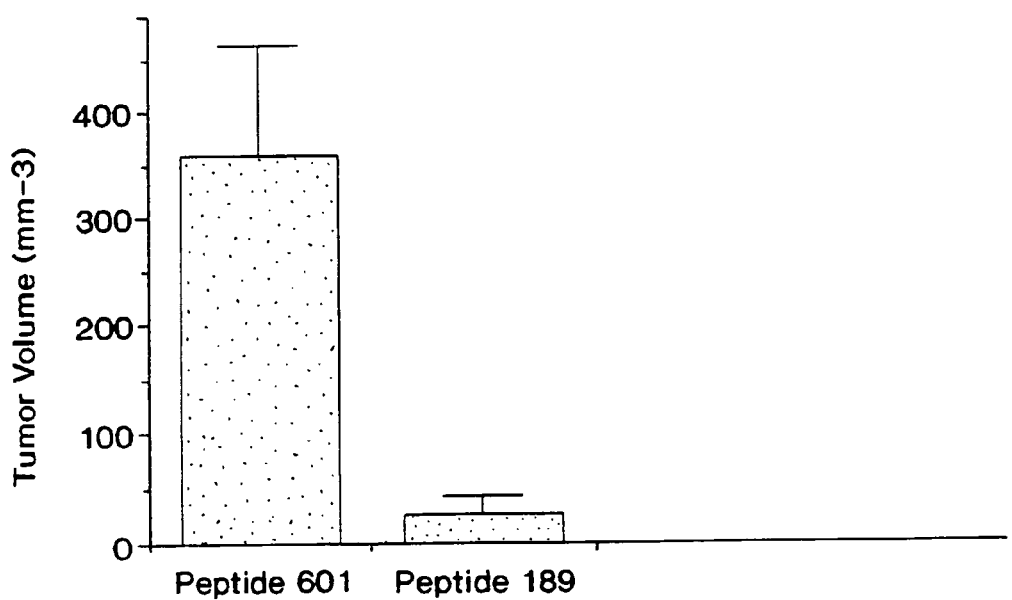
FIG. 9 is a histogram of the effects of control versus an $\alpha_v\beta_5$ peptide antagonist, labeled peptide 189 (SEQ ID NO 9) on melanoma tumor growth as measured by tumor volume in mm$^3$ plotted on the Y-axis. The assay and results are described in Example 8.

The results are shown in FIG. 9 where the tumor volume in mm³ is plotted on the Y-axis against the peptide treatments on the X-axis. The test peptide having SEQ ID NO 9, labeled in the figure as peptide 189, significantly reduced the tumor volume to approximately 25 mm³ compared to control peptide (labeled as peptide 601) where the tumor volume was greater than 300 mm³.

Thus, the blocking of the $\alpha_v\beta_5$ receptor by the intravenous application of $\alpha_v\beta_5$ antagonist peptide 189 resulted in a regression of a melanoma tumor in this model system in the same manner as the CAM and rabbit eye model systems as described previously.

Figure 21:
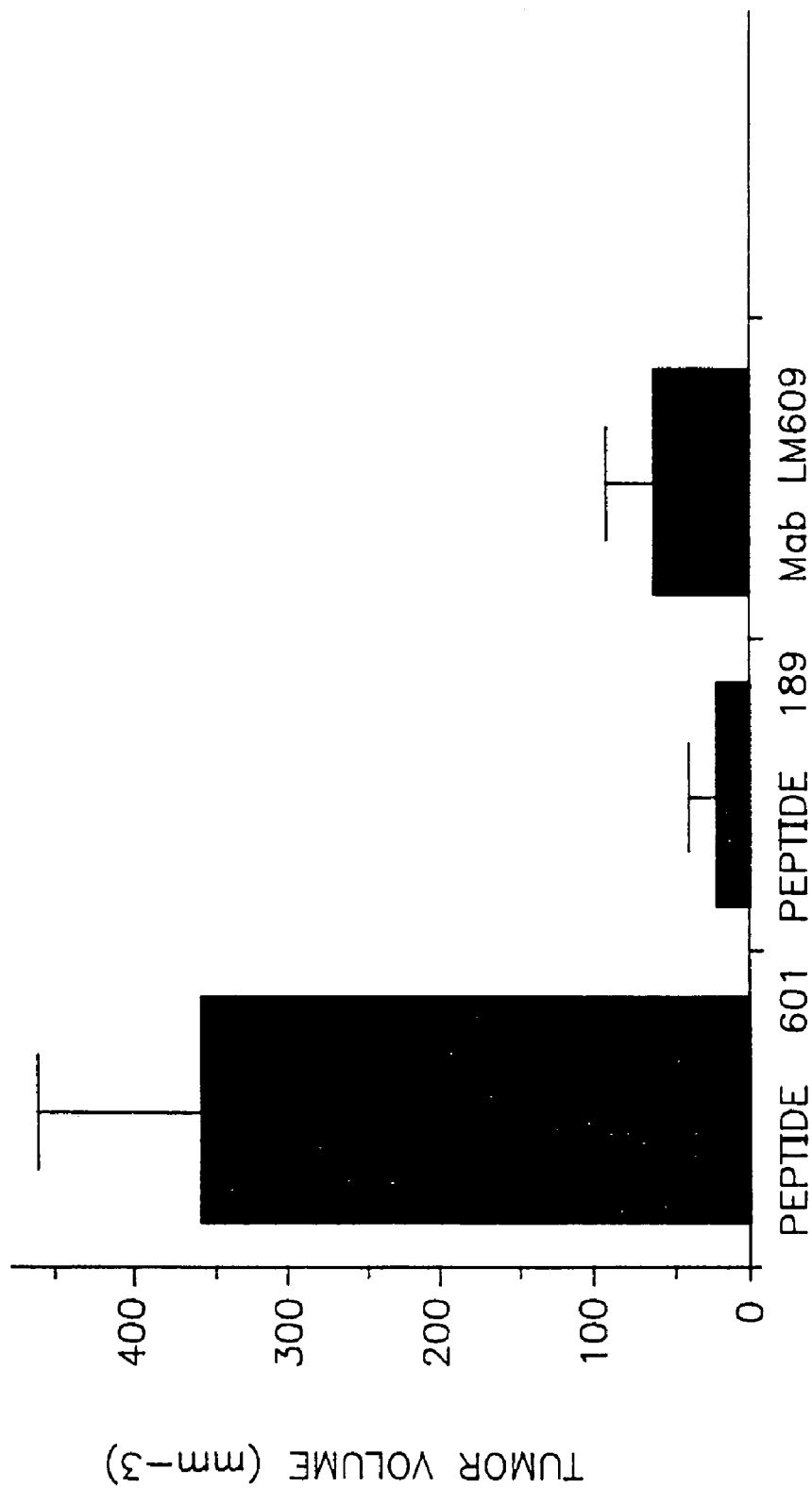
FIG. 21 illustrates the effect of peptides and antibodies on melanoma tumor growth in the chimeric mouse:human model as further described in Example 8. The peptides assessed included control 69601 (labeled 601) and antagonist 85189 (labeled 189). The antibody tested was LM609. Tumor volume in mm$^3$ is plotted on the Y-axis against the various treatments on the X-axis.

In other experiments with M21-L melanoma tumor cells in the mouse:human chimeric assay system, the response with mAB LM609 was compared with the response obtained with the synthetic peptide 85189 (SEQ ID NO 9) as compared to control synthetic peptide 69601 (SEQ ID NO 5). The assays were performed as described above. The results, shown in FIG. 21, demonstrate that the synthetic peptide 85189 reduced tumor volume to below 25 mm³ as compared to control peptide where the tumor volume was approximately 360 mm³. The mAB LM609 also significantly reduced tumor volume to approximately 60 mm³.

Thus, blocking of the $\alpha_v\beta_3$ receptor by the intravenous application of $\alpha_v\beta_3$-specific LM609 antibody and peptides resulted in a regression of a carcinoma in this model system as compared to the other model systems described in this invention.

Figure 22A:
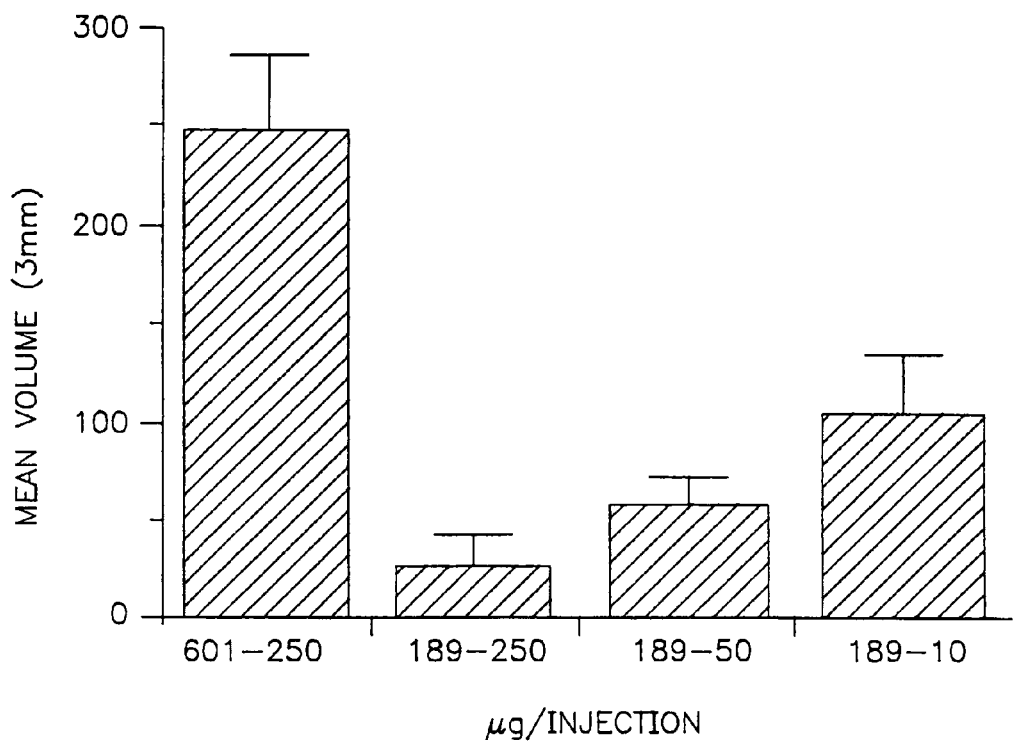
FIGS. 22A and 22B respectively show the effect of antagonist 85189 (labeled 189) compared to control peptide 69601 (labeled 601) in reducing the volume and wet weight of M21L tumors over a dosage range of 10, 50 and 250 μg/injection as further described in Example 8.
Figure 22B:
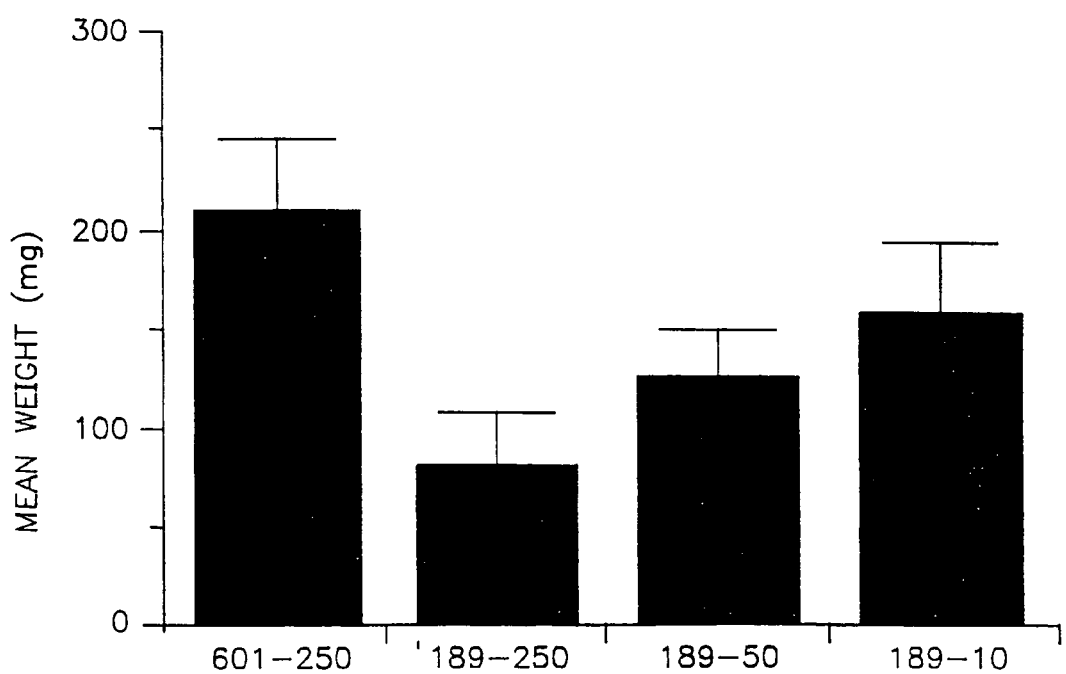

In additional assays with the SCID mice model having measurable M21-L tumors, in a preliminary analysis, a dose response curve was performed for peptides 69601 (control) and 85189 (test) injected over a concentration range of 10 to 250 µg/ml. The mean volume and weight of resected tumors following treatment were determined with the results respectively shown in FIGS. 22A and 22B. Peptide 85189 was effective at inhibiting M21-L tumor growth over the concentration range tested compared to treatment with control peptide with the most effective dosage being 250 µg/ml.

For analyzing peptide 85189 treatment effectiveness over a time course, two treatment regimens were evaluated in the same SCID tumor model. In one assay, treatment with either peptide 85189 or 69601 was initiated on day 6, with day 0 being the day of M21-L tumor injection of $3\times10^6$ cells subcutaneously into mouse skin, with intraperitoneal injections of 250 µg/ml peptide 85189 or control 69601 every other day until day 29. The other assay was identically performed with the exception that treatment was initiated on day 20. At the end of the assays, the tumors were resected and the mean tumor volume in mm$^3$ was determined. The data was plotted as this value +/− the standard error of the mean.

Figure 23A:
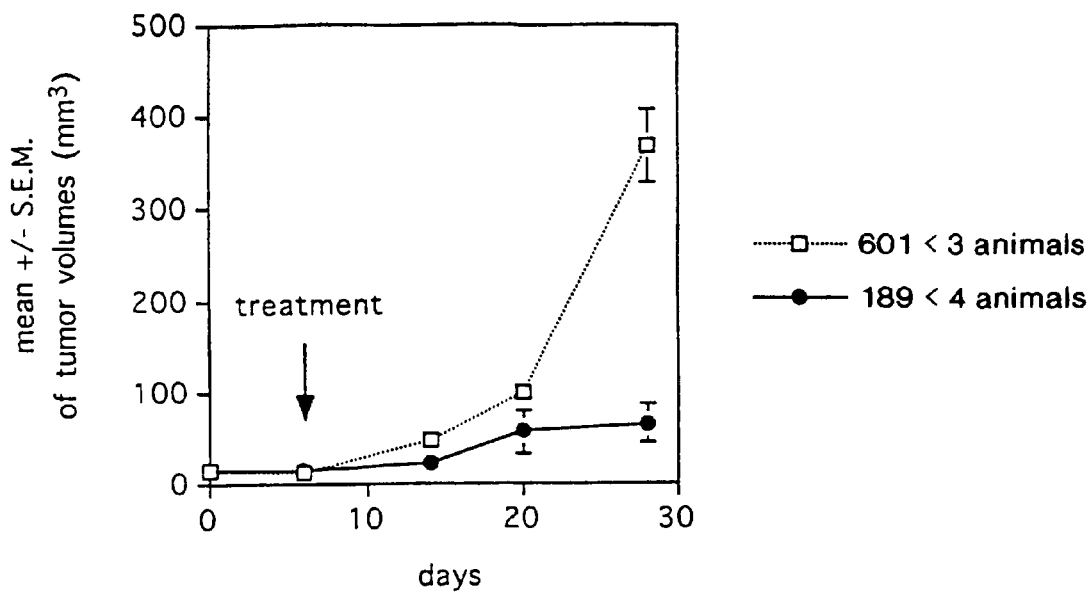
FIGS. 23A and 23B show the effectiveness of antagonist peptide 85189 (labeled 189 with a solid line and filled circles) against control peptide 69601 (labeled 601 on a dotted line and open squares) at inhibiting M21L tumor volume in the mouse:human model with two different treatment regimens as further described in Example 8. Tumor volumes in mm$^3$ is plotted on the Y-axis against days on the X-axis.
Figure 23B:
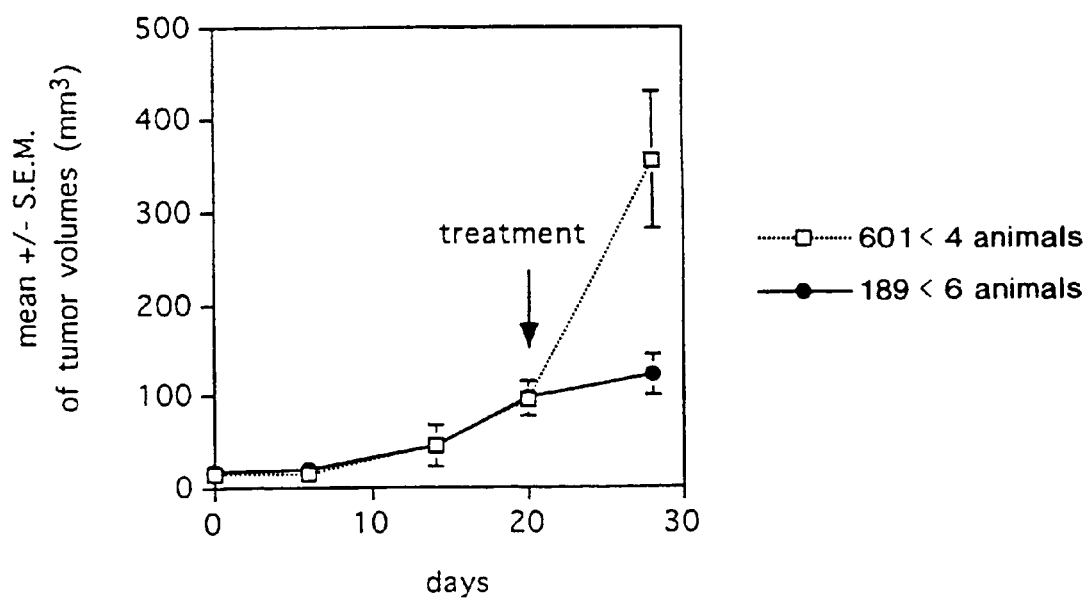

The results of these assays, respectively shown in FIGS. 23A and 23B, indicate that peptide 85189 but not 69601 inhibited tumor growth at various days after treatment was initiated, depending on the particular treatment regimen. Thus, peptide 85189 is an effective $\alpha_v\beta_5$ antagonist of both angiogenesis and thus tumor growth.

The SCID/human chimeric model above is also used for assessing the effectiveness of other $\alpha_v\beta_5$ antagonists of this invention, namely antibodies. MMP-2 preparations, previously prepared, and organic molecules, the latter of which are prepared as described in Example 10.

9. Preparation of a Murine Mouse Model for $\alpha_v\beta_5$-Mediated Retinal Angiogenesis and Inhibition Thereof with $\alpha_v\beta_5$ Antagonists Based on the observation in Example 2C of $\alpha_v\beta_3$ and $\alpha_v\beta_5$ expression in retinal neovascular tissue, a novel mouse model was used to study the effects of systemically administered cyclic peptide antagonists of both integrins on retinal angiogenesis. Newborn mice develop retinal vessels during the first two weeks postnatally during which time the superficial retinal vasculature forms a rich, highly branched network of vessels that originate at the optic nerve head and radiate peripherally to cover the retinal surface in a manner similar to that observed in other mammals and humans (Jiang et al., *Glia.* 15:1–10 (1995).

For the model, newborn mice were injected subcutaneously twice daily for four days starting from day 0 with the cyclic peptide RGDfV (SEQ ID NO 4) (also referred to as peptide 203) or the control peptide RADfV (SEQ ID NO 5). On postnatal day five, globes were removed and fixed in 4.0% paraformaldehyde (PFA) at room temperature.

To quantitate mouse retinal angiogenesis, the distance from the optic nerve head to the most distal point of a single vessel selected in each of six equal sectors around a twelve hour clock was measured. The mean distance was calculated and averaged with similar data obtained from an entire litter. To measure the total volume of retinal blood vessels, the entire specimen was scanned in 2.0 µm optical sections and stored digitally. The "seed" function in Bio-Rad's Lasersharp software was then used to threshold and count cubic pixels in each section. A macro was written to sum the volume of all sections and determine the value for all vascular structures.

With the direct measurement of vessel growth in two dimensions from photographs, systemically, administered peptide antagonist 203 inhibited retinal vasculogenesis, relative to control peptide, by 44% (N=9, p<0.0000001, paired t-test). No statistical difference was seen between untreated newborn mice and five-day old mice receiving peptide 203, thus the peptide effectively inhibits vasculogenesis. In addition, no statistical difference was seen between untreated five-day old mice and the same aged mice receiving control peptide. Thus, inhibition of retinal vasculogenesis in RGDfV-treated newborn mice when compared to untreated counterparts is effectively 100%.

Using a more quantitative analysis taking the three dimensional nature of vessel growth, a 78% reduction in the retinal vascular volume in the peptide 203-treated animals compared to the controls was seen. The mean volume of vessels on postnatal day five in 203-treated animals was $3.6\times10^6$ µm$^3$ and in control-treated animal was $15.7\times10^6$ µm$^3$. The volume occupied by retinal blood vessels in untreated newborn mice was indistinguishable from the five-day old 203-treated animals.

The results obtained above showed that the antagonists specifically blocked new blood vessel formation with no effect on established vessels. The results indicate that the pathology of retinal neovascular disease is distinct from that seen with subretinal neovascular disease and that antagonists of $\alpha_v\beta_5$ are effective for treating patients with blinding eye disease associated with angiogenesis.

Similar assays are performed with the MMP-2 and organic mimetic $\alpha_v\beta_5$ antagonists prepared as respectively described in Example 7 and Example 10.

10. Preparation of Organic Molecule $\alpha_v\beta_5$ Antagonists

The synthesis of organic $\alpha_v\beta_5$ antagonist Compounds 7, 9, 10, 12, 14, 15, 16, 17 and 18 is described below and is also shown in the noted figures. The resultant organic molecules, referred to as organic mimetics of this invention, are then used in the methods for inhibiting $\alpha_v\beta_5$-mediated angiogenesis.

For each of the syntheses described below, optical rotations were measured on Perkin-Elmer 241 spectrophotometer UV and visible spectra were recorded on a Beckmann DU-70 spectrometer. $^1$H and $^{13}$C NMR spectra were recorded at 400 and 500 MHz on Bruker AMX-400 and AMX-500 spectrometer. High-resolution mass spectra (HRMS) were recorded on a VG ZAB-ZSE mass spectrometer under fast atom bombardment (FAB) conditions. Column chromatography was carried out with silica gel of 70–230 mesh. Preparative TLC was carried out on Merck Art. 5744 (0.5 mm). Melting points were taken on a Thomas Hoover apparatus.

Figure 10:
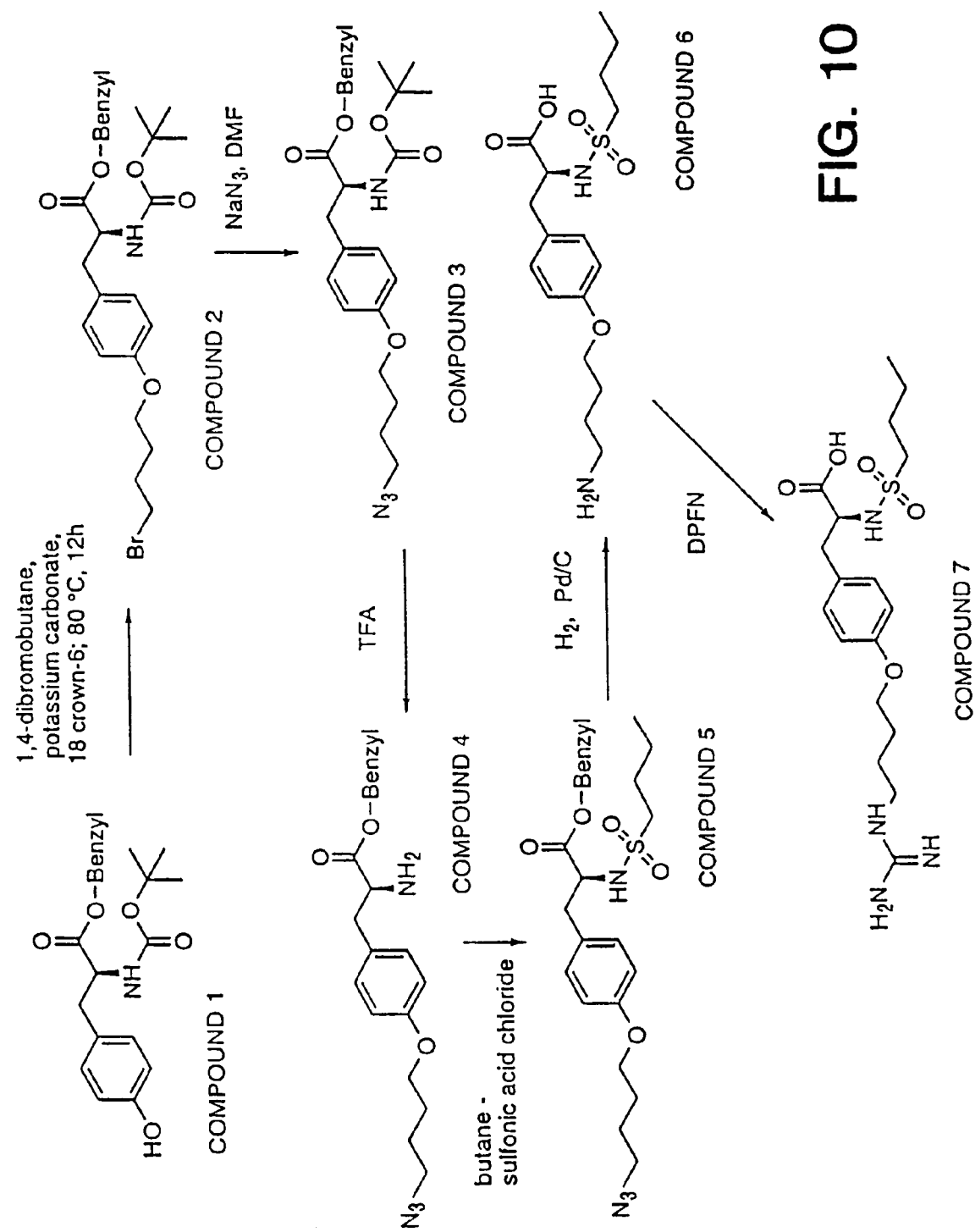
FIG. 10 illustrates the synthesis of Compound 7 as described in Example 10A–G.

A. Compound 1; t-Boc-L-tyrosine Benzyl Ester as Illustrated in FIG. 10

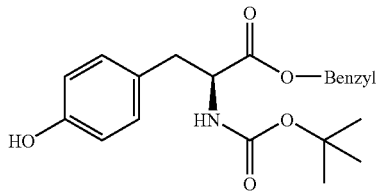

COMPOUND 1

To a solution of N-(tert-butoxycarbonyl)-L-tyrosine(t-Boc-L-tyrosine) (1.0 equivalents; Aldrich) in 0.10 M (M) methylene chloride was added dicyclohexylcarbodiimide (DCC) (1.5 equivalents) at 25° C. and allowed to stir for 1 hour. Next, 1.5 equivalents benzyl alcohol was added and the mixture was stirred for an additional 12 hours at 25° C. The reaction mixture was then diluted with ethyl acetate (0.10 M) and washed twice (2×) with water, once (1×) with brine and dried over magnesium sulfate. The solvent was then removed in vacuo and the crude product was then purified by silica gel column chromatography. Compound 1, t-Boc-L-tyrosine benzyl ester can also be commercially purchased from Sigma.

B. Compound 2; (S)-3-(4-(4-Bromobutyloxy)phenyl-2-N-tert-butyloxycarbonyl-propionic Acid Benzyl Ester as Illustrated in FIG. 10 Step i

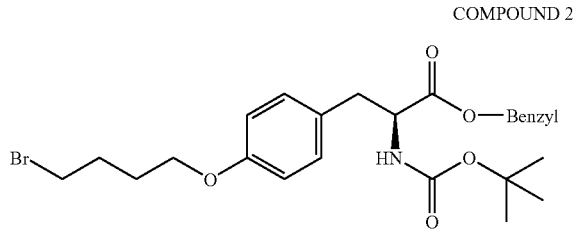

COMPOUND 2

A mixture of t-Boc-L-tyrosine benzyl ester (2 grams, 5.38 mmol; synthesized as described above), 1,4-dibromobutane (1.9 ml, 16.2 mmol; Aldrich), potassium carbonate (5 g) and 18-crown-6 (0.1 g; Aldrich), was heated at 80° C. for 12 hours. After cooling, the precipitate was filtered off and the reaction mixture was evaporated to dryness in vacuo. The crude product was then purified by crystallization using 100% hexane to yield 2.5 g (92%) of Compound 2.

C. Compound 3; (S)-3-(4-(4-Azidobutyloxy)phenyl-2-N-tert-butyloxycarbonyl-propionic Acid Benzyl Ester as Illustrated in FIG. 10 Step ii

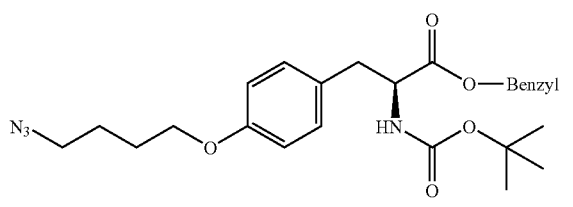

COMPOUND 3

Compound 2 (2.5 g, 4.9 mmol) was stirred with sodium azide (1.6 g, 25 mmol) in dimethylformamide (DMF) (20 ml) at 25° C. for 12 hours. The solvent was then evaporated and the residue was treated with water (approx 10 ml) and extracted twice with ethyl acetate. The organic layers were combined, dried via magnesium sulfate and evaporated to yield 2.0 grams (90%) of Compound 3 as a colorless syrup (FAB-MS: 469 (M+H$^+$).

D. Compound 4; (S)-3-(4-(4-Azidobutyloxy)phenyl-2-amino-propionic Acid Benzyl Ester as Illustrated in FIG. 10 Step iii

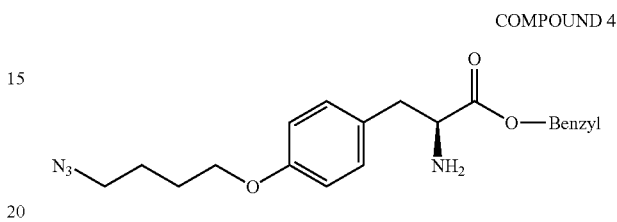

COMPOUND 4

Compound 3 (2.0 g (4.4 mmol)) was dissolved in trifluoroacetic acid (TFA; 2 ml) and stirred for 3 hours at room temperature. Evaporation in vacuo yielded 1.6 grams (quantitative) of Compound 4 as a colorless syrup that was used without further purification for the next step. FAB-MS: 369 (M$^+$H$^+$).

E. Compound 5; (S)-3-(4-(4-Azidobutyloxy)phenyl-2-butylsulfonamido-propionic Acid Benzyl Ester as Illustrated in FIG. 10 Step iv

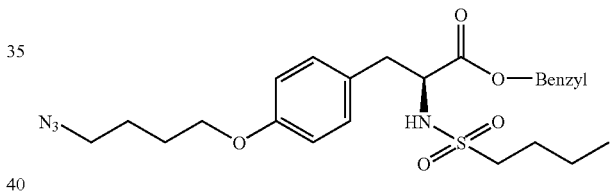

A mixture of Compound 4 (1.6 g; 4.3 mmol), butane sulfonic acid chloride (0.84 ml; 6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of Compound 5 as an amorphous solid.

F. Compound 6; (S)-3-(4-(4-Aminobutyloxy)phenyl-2-butylsulfonamido-propionic Acid as Illustrated in FIG. 10 Step v

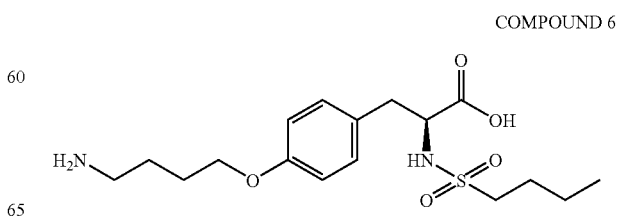

COMPOUND 6

Compound 5 (1.3 g (2.6 mmol) was dissolved in 20 ml of ethyl acetate/methanol/water 5/3/1 and 0.2 ml trifluoroacetic acid (TFA) and hydrogenated under hydrogen (1 atmosphere; Parr Shaker apparatus) at 25° C. in the presence of 100 mg palladium (10% on charcoal). After 3 hours, the catalyst was filtered off and the solvent was evaporated to yield Compound 6 as an oily residue. After lyophilization from water 1.0 gram (quantitative) of Compound 6 was obtained as a white powder. FAB-MS: 373 ($M^+H^+$).

G. Compound 7; (S)-3-(4-(4-Guanidinobutyloxy)phenyl-2-butylsulfonamido-propionic Acid as Illustrated in FIG. 10 Step vi

COMPOUND 7

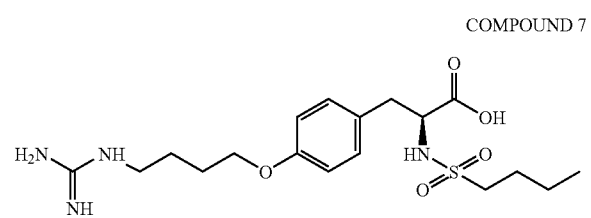

Compound 6 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60° C. for 12 hours. After cooling, the solvent was evaporated in vacuo, and the residue was purified by HPLC (Lichrocart RP-18, gradient acetonitrile/water+0.3% TFA 99:1 to 1:99) to yield 50 mg (25%) of Compound 7 as a white, amorphous powder, after lyophilization. FAB-MS: 415 ($M^+H^+$), m.p.: 70° C.

Figure 11:
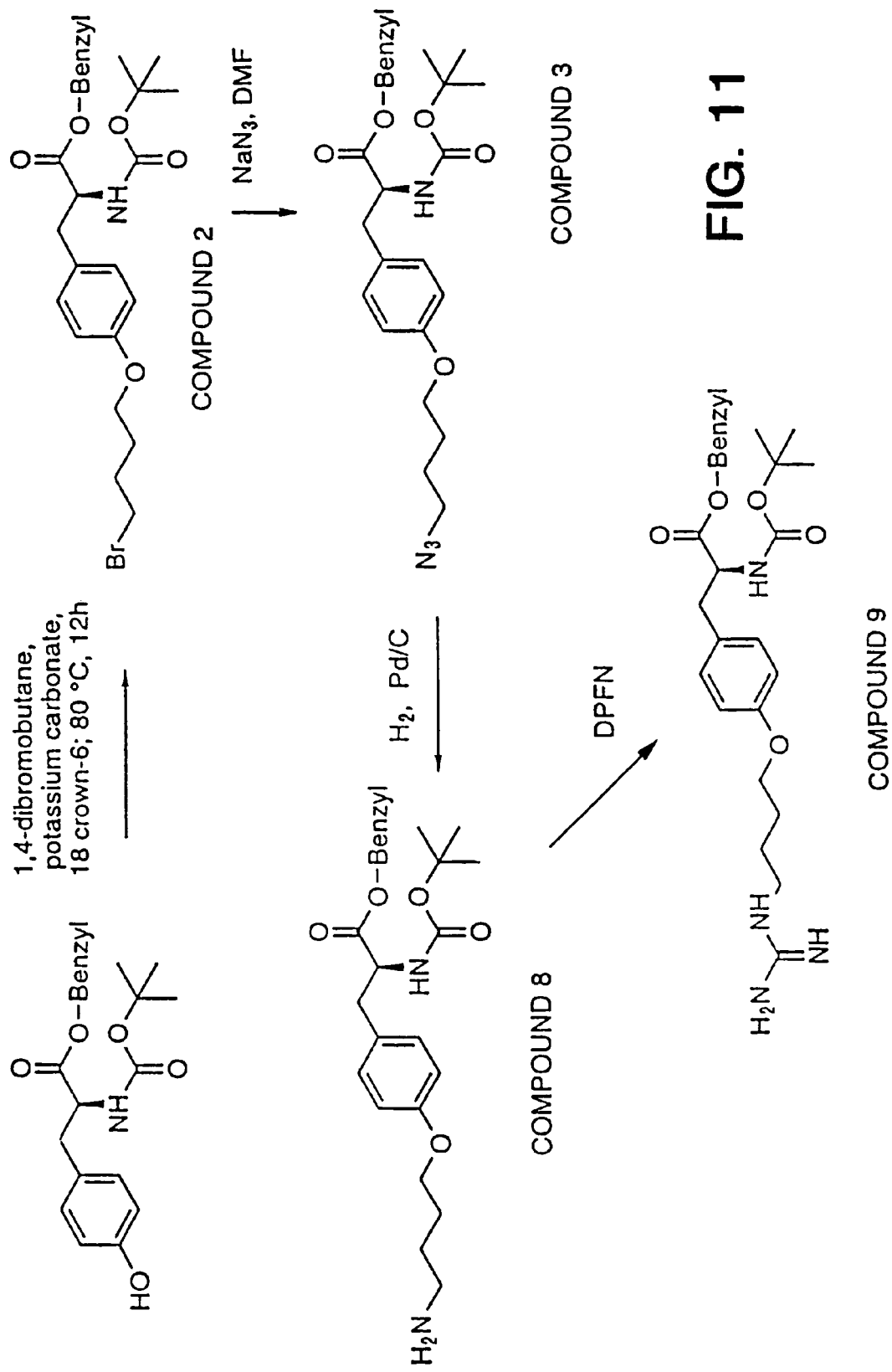
FIG. 11 illustrates the synthesis of Compound 9 as described in Example 10A–C; H–I.

H. Compound 8; (S)-3-(4-(4-Aminobutyloxy)phenyl-2-N-tert,butyloxycarbonyl-propionic Acid as Illustrated in FIG. 11 Step iii

COMPOUND 8

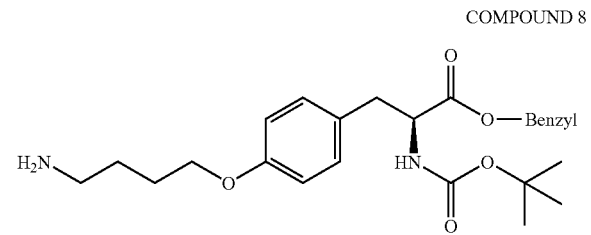

Compound 3 (0.5 g (1.07 mmol) was dissolved in 10 ml of ethyl acetate/methanol/water 5/3/1 and 0.1 ml trifluoroacetic acid (TFA) and hydrogenated under hydrogen (1 atmosphere; Parr Shaker apparatus) at 25° C. in the presence of 30 mg palladium (10% on charcoal). After 3 hours, the catalyst was filtered off and the solvent was evaporated to yield Compound 8 as an oily residue. After lyophilization from water 370 milligram (quantitative) of Compound 8 was obtained as a white powder. FAB-MS: 353 ($M^+H^+$).

I. Compound 9; (S)-3-(4-(4-Guanidinobutyloxy)phenyl-2-N-tert,butyloxycarbonyl-propionic Acid as Illustrated in FIG. 11 Step iv

COMPOUND 9

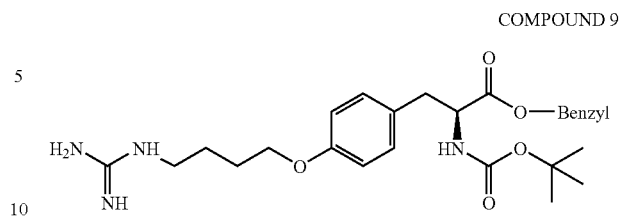

Compound 8 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60° C. for 12 hours. After cooling, the solvent was evaporated in vacuo, and the residue was purified by HPLC (Lichrocart RP-18, gradient acetonitrile/water+0.3% TFA 99:1 to 1:99) to yield 160 mg (90%) of Compound 9 as a white, amorphous powder, after lyophilization. FAB-MS: 395 ($M^+H^+$).

Figure 12:
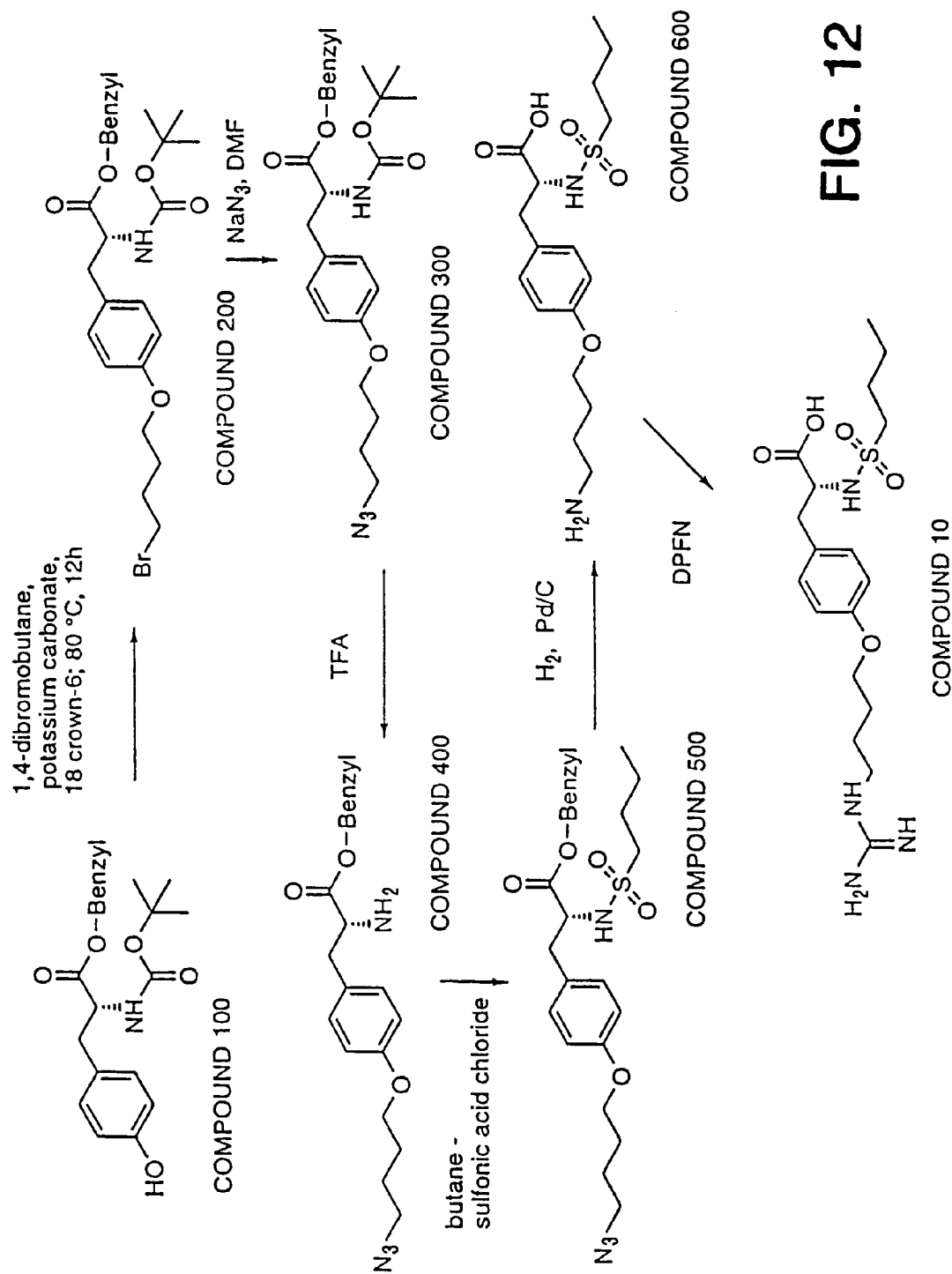
FIG. 12 illustrates the synthesis of Compound 10 as described in Example 10J.

J. Compound 10; (R)-3-(4-(4-Guanidinobutyloxy)phenyl-2-butylsulfonamido-propionic Acid as Illustrated in FIG. 12 Steps i–vi

COMPOUND 10

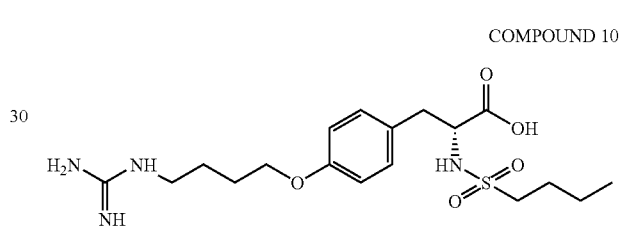

The identical reaction sequence to synthesize Compound 7 was used to prepare the D-tyrosine analog 10 of which 205 mg were obtained as a white amorphous material FAB-MS: 415 ($M^+H^+$) as follows using intermediate Compounds 100–600 to form Compound 10:

1) Compound 100; t-Boc-D-tyrosine Benzyl Ester as Illustrated in FIG. 12

COMPOUND 100

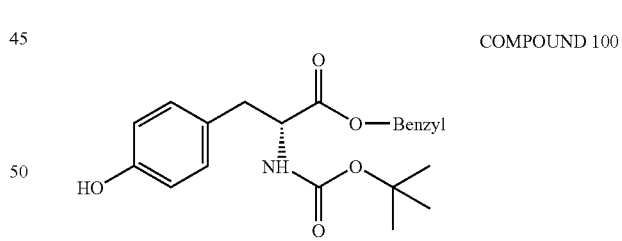

To a solution of N-(tert-butoxycarbonyl)D-tyrosine(t-Boc-L-tyrosine) (1.0 equivalents; Aldrich) in 0.10 M methylene chloride was added dicyclohexylcarbodiimide (DCC) (1.5 equivalents) at 25° C. and allowed to stir for 1 hour. Next, 1.5 equivalents benzyl alcohol was added and the mixture was stirred for an additional 12 hours at 25° C. The reaction mixture was then diluted with ethyl acetate (0.10 M) and washed 2× with water, 1× with brine and dried over magnesium sulfate. The solvent was then removed in vacuo and the crude product was then purified by silica gel column chromatography.

2) Compound 200; (R)-3-(4-(4-Bromobutyloxy)phenyl-2-N-tert-butyloxycarbonyl-propionic Acid Benzyl Ester as Illustrated in FIG. 12 Step i

COMPOUND 200

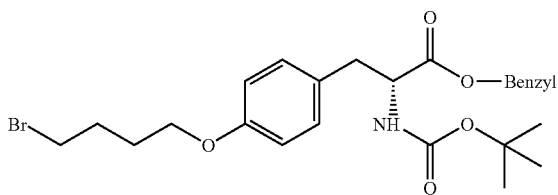

A mixture of t-Boc-D-tyrosine benzyl ester (2 grams, 5.38 mmol; synthesized as described above), 1,4-dibromobutane (1.9 ml, 16.2 mmol; Aldrich), potassium carbonate (5 g) and 18-crown-6 (0.1 g; Aldrich), was heated at 80° C. for 12 hours. After cooling, the precipitate was filtered off and the reaction mixture was evaporated to dryness in vacuo. The crude product was then purified by crystallization using 100% hexane to yield 2.5 g (92%) of Compound 200.

3) Compound 300; (R)-3-(4-(4-Azidobutyloxy)phenyl-2-N-tert-butyloxycarbonyl-propionic Acid Benzyl Ester as Illustrated in FIG. 12 Step ii

COMPOUND 300

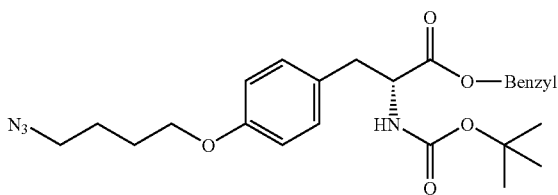

Compound 200 (2.5 g, 4.9 mmol) was stirred with sodium azide (1.6 g, 25 mmol) in dimethylformamide (DMF) (20 ml) at 25° C. for 12 hours. The solvent was then evaporated and the residue was treated with water (approx 10 ml) and extracted twice with ethyl acetate. The organic layers were combined, dried via magnesium sulfate and evaporated to yield 2.0 grams (90%) of Compound 300 as a colorless syrup (FAB-MS: 469 (M+H$^+$).

4) Compound 400; (R)-3-(4-(4-Azidobutyloxy)phenyl-2-amino-propionic Acid Benzyl Ester as Illustrated in FIG. 12 Step iii

COMPOUND 400

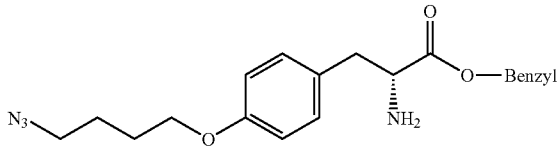

Compound 300 (2.0 g (4.4 mmol)) was dissolved in trifluoroacetic acid (TFA; 2 ml) and stirred for 3 hours at room temperature. Evaporation in vacuo yielded 1.6 grams (quantitative) of Compound 400 as a colorless syrup that was used without further purification for the next step. FAB-MS: 369 (M$^+$H$^+$).

5) Compound 500; (R)-3-(4-(4-Azidobutyloxy)phenyl-2-butylsulfonamido-propionic Acid Benzyl Ester as Illustrated in FIG. 12 Step iv

COMPOUND 500

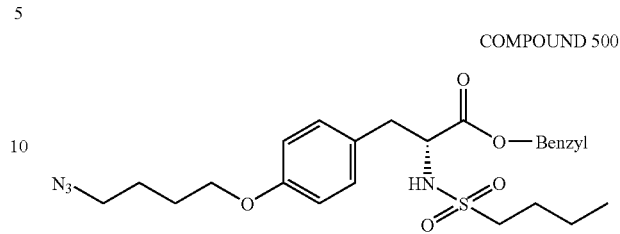

A mixture of Compound 400 (1.6 g; 4.3 mmol), butane sulfonic acid chloride (0.84 ml; 6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of Compound 500 as an amorphous solid.

6) Compound 600; (R)-3-(4-(4-Aminobutyloxy)phenyl-2-butylsulfonamido-propionic Acid as Illustrated in FIG. 12 Step v

COMPOUND 600

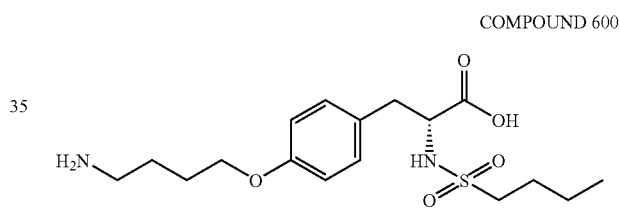

Compound 500 (1.3 g (2.6 mmol) was dissolved in 20 ml of ethyl acetate/methanol/water 5/3/1 and 0.2 ml trifluoroacetic acid (TFA) and hydrogenated under hydrogen (1 atmosphere; Parr Shaker apparatus) at 25° C. in the presence of 100 mg palladium (10% on charcoal). After 3 hours, the catalyst was filtered off and the solvent was evaporated to yield Compound 600 as an oily residue. After lyophilization from water 1.0 gram (quantitative) of Compound 600 was obtained as a white powder. FAB-MS: 373 (M$^+$H$^+$).

7) Compound 10; (R)-3-(4-(4-Guanidinobutyloxy)phenyl-2-butylsulfonamido-propionic Acid as Illustrated in FIG. 12 Step vi Compound 600 (200 mg; 0.5 mmol), 3,5-dimethylpyrazol-1-carboxamidine nitrate (DPFN) (170 mg; 0.8 mmol; Aldrich Chemical Company) and triethylamine (0.15 ml, 1.0 mmol) in dimethylformamide (DMF; 5 ml) were heated at 60° C. for 12 hours. After cooling, the solvent was evaporated in vacuo, and the residue was purified by HPLC (Lichrocart RP-18, gradient acetonitrile/water+0.3% TFA 99:1 to 1:99) to yield 50 mg (25%) of Compound 10 as a white, amorphous powder, after lyophilization. FAB-MS: 415 (M$^+$H$^+$), m.p.: 70° C.

K. Compound 11; (S)-3-(4-(4-Azidobutyloxy)phenyl-2-(10-camphorsulfonamido)-propionic Acid Benzyl Ester as Illustrated in FIG. 4

COMPOUND 11

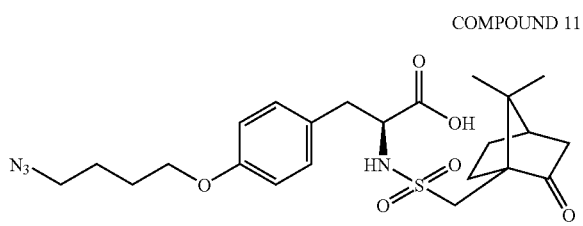

A mixture of Compound 4 (1.0 g; 2.7 mmol), 10-camphorsulfonic acid chloride (6.6 mmol; Aldrich Chemical Company) and triethyl amine (1.5 equivalents) were stirred in methylene chloride (20 mL) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield 1.4 grams (67%) of Compound 11 as an amorphous solid.

L. Compound 12; (S)-3-(4-(4-Guanidinobutyloxy)phenyl-2-(10-camphorsulfonamido)-propionic Acid as Illustrated in FIG. 4 Steps i–ii

COMPOUND 12

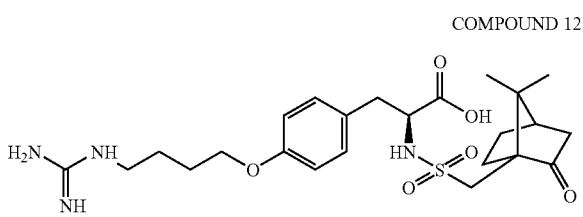

Compound 12 is obtained after hydrogenation and guanylation of compound 11 according to the following conditions:

Step i: Compound 11 (1.3 g (2.6 mmol) was dissolved in 20 mL of ethyl acetate/methanol/water 5/3/1 and 0.2 mL trifluoroacetic acid (TFA) and hydrogenated under hydrogen (1 atmosphere; Parr Shaker apparatus) at 25° C. in the presence of 100 mg palladium (10% on charcoal). After 3 hours, the catalyst was filtered off and the solvent was evaporated to yield the intermediate amine as an oily residue. After lyophilization from water 1.0 gram (quantitative) of the intermediate amine was obtained as a white powder, which was carried on as follows:

Step ii: The above formed intermediate amine compound (200 mg; 0.5 mmol), 3,5-dimethylpyrazol-1-carboxamidine nitrate (DPFN) (170 mg; 0.8 mmol; Aldrich Chemical Company) and triethylamine (0.15 mL, 1.0 mmol) in dimethylformamide (DMF; 5 mL) were heated at 60° C. for 12 hours. After cooling, the solvent was evaporated in vacuo, and the residue was purified by HPLC (Lichrocart RP-18, gradient acetonitrile/water+0.3% TFA 99:1 to 1:99) to yield 50 mg (25%) of compound 12 as a white, amorphous powder, after lyophilization. FAB-MS: 509.6 (M+H+).

Figure 13:
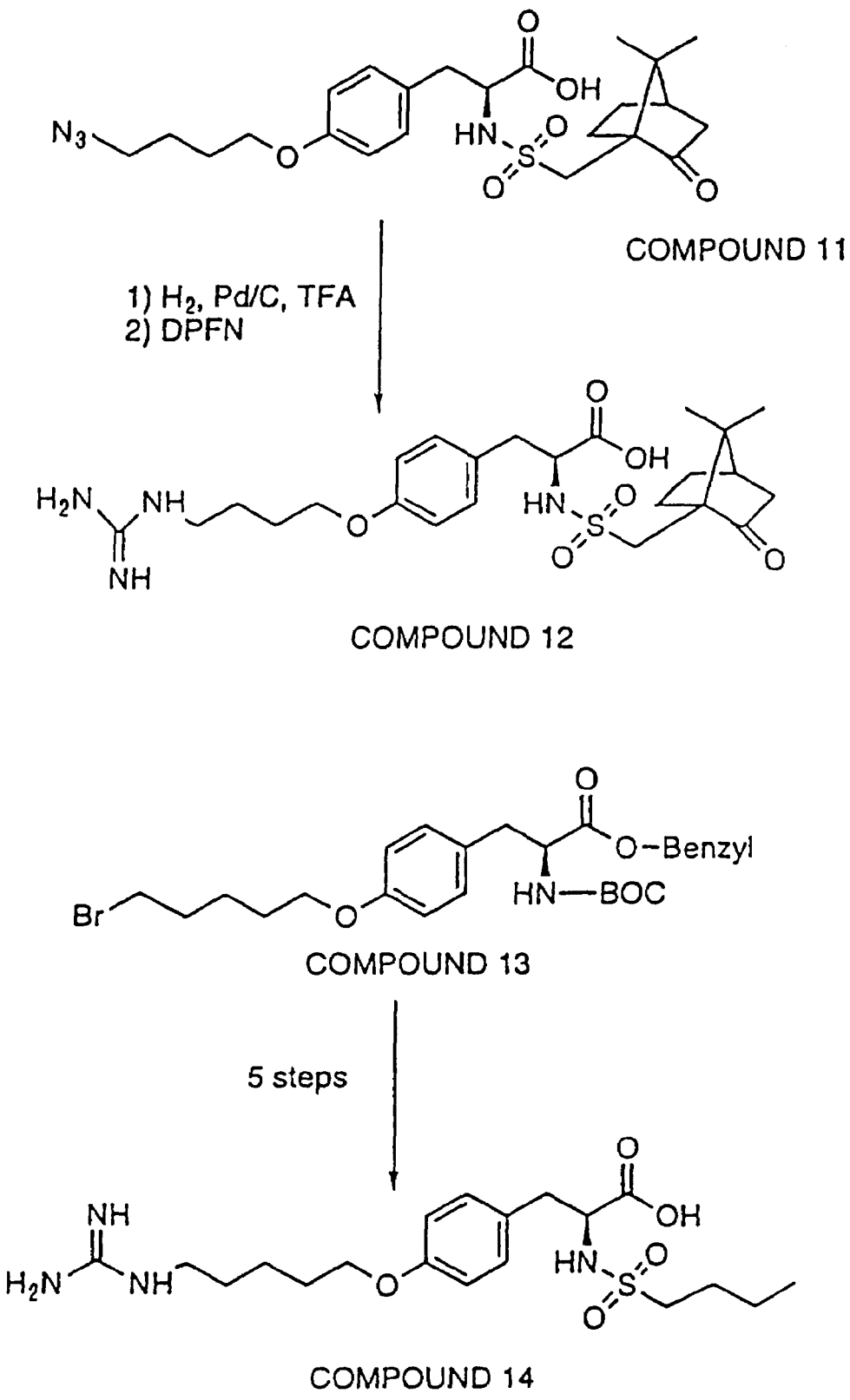
FIG. 13 illustrates the synthesis of Compound 12 and Compound 14 as respectively described in Example 10K–L and 10M–N.

M. Compound 13; (S)-3-(4-(5-Bromopentyloxy)phenyl-2-N-tert,butyloxycarbonyl-propionic Acid Benzyl Ester as Illustrated in FIG. 13

COMPOUND 13

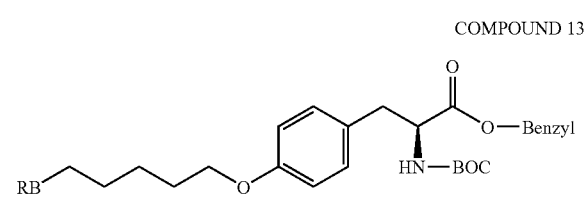

A mixture of t-Boc-L-tyrosine benzyl ester (4.5 grams, 12.1 mmol; Compound 1 synthesized as described above), 1,5-dibromopentane (5 ml, 36.7 mmol; Aldrich), potassium carbonate (10 g) and 18-crown-6 (0.25 g; Aldrich), was heated at 80° C. for 12 hours. After cooling, the precipitate was filtered off and the reaction mixture was evaporated to dryness in vacuo. The crude product was then purified by crystallization using 100% hexane to yield 5.35 g (85%) of Compound 13.

N. Compound 14; (S)-3-(4-(5-Guanidinopentyloxy)phenyl-2-butylsulfonamido-propionic Acid as Illustrated in FIG. 13 Steps i–v

COMPOUND 14

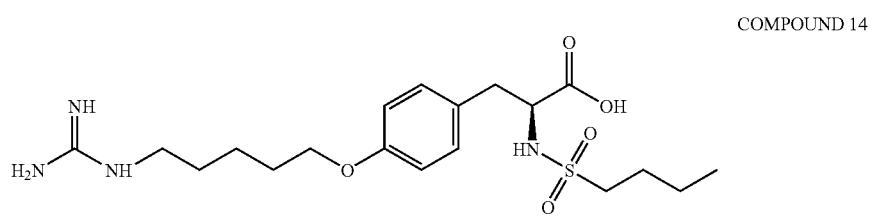

The 5 step reaction sequence of bromine-azide-exchange, Boc-cleavage, sulfonylation with butane sulfonic acid chloride, hydrogenation and guanylation with DPFN was carried out identically to the above procedures using intermediate Compounds 1–6 to form Compound 7 or the procedures using Compounds 100–600 to form Compound 10, as discussed above. Compound 14 was obtained as a white powder FAB-MS: 429 (M+H+).

O. Compound 15; 3-(4-Amidinophenyl)-5-(4-(2-carboxy-2-aminoethyl)phenoxy)methyl-2-oxazolidinone, Dihydrochloride as Shown in FIG. 14

1) Synthesis of Starting Material 2-N-Boc-amino-3-(4-hydroxyphenyl)propionate for Compound 15

COMPOUND 15

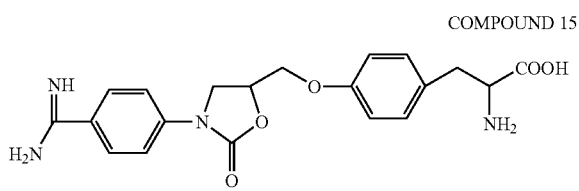

The starting material 2-N-BOC-amino-3-(4-hydroxy-phenyl)propionate was obtained via esterification of (D or L), N-(tert-butoxycarbonyl)-L(D)-tyrosine (t-Boc-L(D)-tyrosine) (1.0 equivalents; Sigma) in 0.10 M methanol and dilute 1% HCl. The reaction mixture was stirred at 25° C. for 12 hours and then neutralized via potassium carbonate and then diluted with ethyl acetate (0.10 M) and washed 2x with water, 1x brine and dried over magnesium sulfate. The solvent was then removed in vacuo and the crude product was then purified by silica gel column chromatography to obtain 2-N-BOC-amino-3-(4-hydroxy-phenyl)propionate.

2) Synthesis of Starting Material 3-p-N-BOC-amidino-phenyl-5-methanesulfonyloxy-methyl-2-oxazolidinone for Compound 15; 3-Step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25° C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25° C., was stirred with diethyl carbonate (1.1 equivalents; Aldrich) and potassium tert-butylate (1.1 equivalents; Aldrich) at 110° C. for 6 hours. Next, the reaction mixture was diluted with ethyl acetate (0.10 M) and washed 2x with water, 1x with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25° C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2x with water, 1x with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25° C. and stirred for 6 hours. Next, the reaction mixture was diluted with ethyl acetate (0.10 M) and washed 2x with water, 1x with brine and dried over magnesium sulfate. The solvent was then removed in vacuo and the crude product was then esterified in 0.10 M methylene chloride and 1.1 equivalents methanesulfonyl chloride. The reaction mixture was stirred at 0° C. for 6 hours and then quenched with water (5 equivalents) and then diluted with ethyl acetate (0.10 M) and washed 2x with water, 1x with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of Intermediates 2-N-BOC-amino-3-(4-hydroxyphenyl)propionate with 3-p-N-BOC-amidino-phenyl-5-methanesulfonyloxy-methyl-2-oxazolidinone to Form Protected Form of Compound 15, 3-(4-BOC-amidinophenyl)-5-(4-(2-methoxy-carbonyl-2N-BOC-aminoethyl) phenyoxylmethyl-2-oxazolidinone A mixture of 1.9 grams 2-N-BOC-amino-3-(4-hydroxyphenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2x with water, 1x with brine and dried over magnesium sulfate. The solvent was then removed in vacuo and the crude product was then purified by silica gel column chromatography to obtain protected form of Compound 15, 3-(4-BOC-amidinophenyl)-5-(4-methoxy-carbonyl-2N-BOC-aminoethyl) phenyoxylmethyl-2-oxazolidinone which was carried onto the next step.

4) Deprotection of Protected Form of Compound 15 to Form Compound 15: 3-(4-Amidinophenyl)-5-(4-(2-carboxy-2-amino-ethyl)phenoxy)methyl-2-oxazolidinone, Dihydrochloride, FIG. 14

Treatment of the protected form of Compound 15, 3-(4-BOC-amidinophenyl)-5-(4-(2-methoxy-carbonyl-2N-BOC-aminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0° C. to 25° C. for 3 hours. The reaction mixture was then quenched with sodium bicarbonate (5 equivalents) and then diluted with ethyl acetate (0.10 M) and washed 2x with water, 1x with brine and dried over magnesium sulfate. The solvent was then removed in vacuo and the crude product was then purified by silica gel column chromatography to obtain Compound 15: 3-(4-amidinophenyl)-5-(4-(2-carboxy-2-amino-ethyl)phenoxy)methyl-2-oxazolidinone, dihydrochloride; m.p. 165° C. (d).

P. Compound 16; 3-(4-Amidinophenyl)-5-(4-(2-carboxy-2-N-butylsulfonylaminoethyl)phenoxy)methyl-2-oxazolidinone as Shown in FIG. 14

1) Synthesis of Starting Material 2-N-butylsulfonylamino-3-(4-hydroxyphenyl)propionate for Compound 16

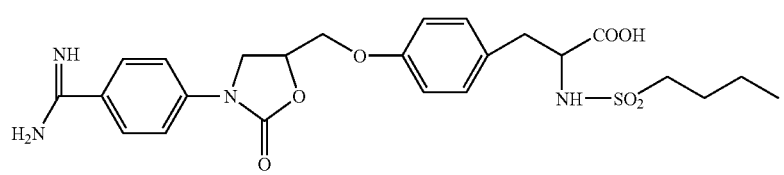

COMPOUND 16

The starting material 2-N-butylsulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25° C. for 12 hours and then neutralized via potassium carbonate and then diluted with ethyl acetate (0.10 M) and washed 2× with water, 1× with brine and dried over magnesium sulfate. The solvent was then removed in vacuo and the crude product was then carried on as follows:

A mixture of the above compound (4.3 mmol), butane sulfonic acid chloride (6.6 mmol) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of Starting Material 3-p-N-BOC-amidino-phenyl-5-methanesulfonyloxy-methyl-2-oxazolidinone for Compound 16; 3-Step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25° C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25° C., was stirred with diethyl carbonate (1.1 equivalents; Aldrich) and potassium tert-butylate (1.1 equivalents; Aldrich) at 110° C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25° C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25° C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 equivalents methanesulfonyl chloride. The reaction mixture was stirred at 0° C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of Intermediates 2-N-butylsulfonylamino-3-(4-hydroxyphenyl)propionate with 3-p-N-BOC-amidino-phenyl-5-methanesulfonyloxy-methyl-2-oxazolidinone to Form Protected Form of Compound 16, 3-(4-BOC-amidinophenyl)-5-(4-(2-methoxy-carbonyl-2-N-butylsulfonylaminoethyl)phenyoxylmethyl-2-oxazolidinone A mixture of 1.9 grams 2-N-butylsulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 16, 3-(4-BOC-amidinophenyl)-5-(4-(2-methoxy-carbonyl-2-N-butylsulfonylaminoethyl)phenyoxylmethyl-2-oxazolidinone which was carried onto the next step.

4) Deprotection of Protected Form of Compound 16 to Form Compound 16; 3-(4-Amidinophenyl)-5-(4-(2-carboxy-2-N-butylsulfonylaminoethyl)phenoxy)methyl-2-oxazolidinone, FIG. 14

Treatment of the protected form of Compound 16, 3-(4-BOC-amidinophenyl)-5-(4-(2-methoxy-carbonyl-2-N-butylsulfonylaminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0° C. to 25° C. for 3 hours. The reaction mixture was then quenched with sodium bicarbonate (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain Compound 16: 3-(4-amidinophenyl)-5-(4-(2-carboxy-2-N-butylsulfonylaminoethyl)phenoxy)methyl-2-oxazolidinone; m.p. 236–237° C.

Q. Compound 17; 3-(4-Amidinophenyl)-5-(4-(2-carboxy-2-N-propylsulfonylaminoethyl)phenoxy)methyl-2-oxazolidinone as Shown in FIG. 14

1) Synthesis of Starting Material 2-N-propyl-sulfonylamino-3-(4-hydroxyphenyl)propionate for Compound 17;

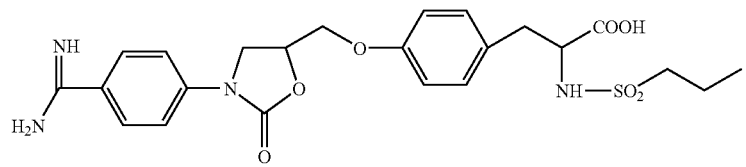

COMPOUND 17

The starting material 2-N-propyl-sulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25° C. for 12 hours and then neutralized via potassium carbonate and then diluted with ethyl acetate (0.10 M) and washed 2× with water, 1× with brine and dried over magnesium sulfate. The solvent was then removed in vacuo and the crude product was then carried on as follows:

A mixture of the above compound (4.3 mmol), propyl sulfonic acid chloride (6.6 mmol; Aldrich) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of Starting Material 3-p-N-BOC-amidino-phenyl-5-methanesulfonyloxy-methyl-2-oxazolidinone for Compound 17; 3-Step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25° C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25° C., was stirred with diethyl carbonate (1.1 equivalents; Aldrich) and potassium tert-butylate (1.1 equivalents; Aldrich) at 110° C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25° C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25° C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 equivalents methanesulfonyl chloride. The reaction mixture was stirred at 0° C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of Intermediates 2-N-propyl-sulfonylamino-3-(4-hydroxyphenyl)propionate with 3-p-N-BOC-amidino-phenyl-5-methanesulfonyloxy-methyl-2-oxazolidinone to Form Protected Form of Compound 17, 3-(4-BOC-amidinophenyl)-5-(4-(2-methoxy-carbonyl-2-N-propyl-sulfonylaminoethyl)-phenyoxylmethyl-2-oxazolidinone A mixture of 1.9 grams 2-N-propyl-sulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 17, 3-(4-BOC-amidinophenyl)-5-(4-(2-methoxy-carbonyl-2-N-propyl-sulfonylaminoethyl)phenyoxylmethyl-2-oxazolidinone which was carried onto the next step.

4) Deprotection of Protected Form of Compound 17 to Form Compound 17; 3-(4-Amidinophenyl)-5-(4-(2-carboxy-2-N-propylsulfonylaminoethyl)phenoxy)methyl-2-oxazolidinone, FIG. 14

Treatment of the protected form of Compound 17, 3-(4-BOC-amidinophenyl)-5-(4-(2-methoxy-carbonyl-2-N-propylsulfonylaminoethyl)phenyoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0° C. to 25° C. for 3 hours. The reaction mixture was then quenched with sodium bicarbonate (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain Compound 17: 3-(4-amidinophenyl)-5-(4-(2-carboxy-2-N-propylsulfonylaminoethyl)phenoxy)methyl-2-oxazolidinone; m.p. 200° C. (d).

R. Compound 18; 3-(4-Amidinophenyl)-5-(4-(2-carboxy-2-N-ethylsulfonylaminoethyl)phenoxy)methyl-2-oxazolidinone as Shown in FIG. 14

1) Synthesis of Starting Material 2-N-ethyl-sulfonylamino-3-(4-hydroxyphenyl)propionate for Compound 18;

COMPOUND 18

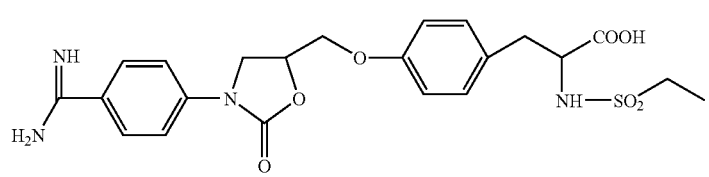

The starting material 2-N-ethyl-sulfonylamino-3-(4-hydroxy-phenyl)propionate was obtained via esterification of ((D or L) tyrosine) (1.0 equivalents; Sigma) in 0.10 M methanol and dilute 1% HCl. The reaction mixture was stirred at 25° C. for 12 hours and then neutralized via potassium carbonate and then diluted with ethyl acetate (0.10 M) and washed 2× with water, 1× with brine and dried over magnesium sulfate. The solvent was then removed in vacuo and the crude product was then carried on as follows:

A mixture of the above compound (4.3 mmol), ethyl sulfonic acid chloride (6.6 mmol; Aldrich) and triethyl amine (1.5 equivalents) were stirred in methylene chloride (20 ml) for 12 hours at room temperature. The reaction mixture was then evaporated and the residue was dissolved in ethylacetate, washed with dilute HCl, aqueous sodium bicarbonate and water. After evaporation to dryness the crude product was purified by flash chromatography (silica gel, toluene/ethylacetate 15:1) to yield the title compound.

2) Synthesis of Starting Material 3-p-N-BOC-amidino-phenyl-5-methanesulfonyloxy-methyl-2-oxazolidinone for Compound 18; 3-Step Procedure as Follows:

p-amino-benzonitrile (1.0 equivalents; Aldrich) in methylene chloride (0.10 M) was stirred with 2,3-epoxypropanol (1.0 equivalents; Aldrich) for 12 hours at 25° C. The solvent was next removed in vacuo and the crude 4-(2,3-dihydroxypropylamino)benzonitrile was carried onto the next step as follows:

4-(2,3-dihydroxypropylamino)benzonitrile (1.0 equivalents; as described above), in dimethylformamide (0.10 M), at 25° C., was stirred with diethyl carbonate (1.1 equivalents; Aldrich) and potassium tert-butylate (1.1 equivalents; Aldrich) at 110° C. for 6 hours. Next, the reaction mixture was diluted with ethyl acetate (0.10 M) and washed 2× with water, 1× with brine and dried over magnesium sulfate. The solvent was then removed in vacuo and the crude product was then purified by silica gel column chromatography to obtain 3-(4-cyanophenyl)-5-hydroxymethyl-2-oxazolidine and carried onto the next step as follows:

3-(4-cyanophenyl)-5-hydroxymethyl-2-oxazolidine (1.0 equivalents; as described above), in methylene chloride (0.10 M) at 25° C. was stirred with 1.1 equivalents hydrogen sulfide, 1.1 equivalents methyl iodide, and 1.1 equivalents ammonium acetate. The reaction mixture was stirred for 6 hours and then diluted with ethyl acetate (0.10 M) and washed 2× with water, 1× with brine and dried over magnesium sulfate. The solvent was then removed in vacuo and the crude product was then purified by silica gel column chromatography to obtain the amidine which was carried onto the next step as follows:

1.0 equivalents of the amidine, synthesized as described above, was protected with 1.1 equivalents of BOC-ON (2-(BOC-oxyimino)-2-phenylacetonitrile; Aldrich) in methylene chloride (0.10 M) at 25° C. and stirred for 6 hours. Next, the reaction mixture was diluted with ethyl acetate (0.10 M) and washed 2× with water, 1× with brine and dried over magnesium sulfate. The solvent was then removed in vacuo and the crude product was then esterified in 0.10 M methylene chloride and 1.1 equivalents methanesulfonyl chloride. The reaction mixture was stirred at 0° C. for 6 hours and then quenched with water (5 equivalents) and then diluted with ethyl acetate (0.10 M) and washed 2× with water, 1× with brine and dried over magnesium sulfate. The solvent was then removed in vacuo and the crude product was then purified by silica gel column chromatography to obtain 3-p-N-BOC-amidino-phenyl-5-methanesulfonyloxy-methyl-2-oxazolidinone.

3) Coupling of Intermediates 2-N-ethyl-sulfonylamino-3-(4-hydroxyphenyl)propionate with 3-p-N-BOC-amidino-phenyl-5-methanesulfonyloxy-methyl-2-oxazolidinone to Form Protected Form of Compound 18, 3-(4-BOC-amidinophenyl)-5-(4-(2-methoxy-carbonyl-2-N-ethyl-sulfonylaminoethyl)-phenoxylmethyl-2-oxazolidinone A mixture of 1.9 grams 2-N-ethyl-sulfonylamino-3-(4-hydroxy-phenyl)propionate (as described above), 20 ml dimethylformamide (DMF) and NaH (1.0 equivalent), was stirred for 30 minutes at room temperature. After stirring, 1.8 grams 3-p-N-BOC-amidino-phenyl-5-methanesulfonyloxy-methyl-2-oxazolidinone (as described above) in 10 ml dimethylformamide (DMF) was added and stirred again for 15 minutes at room temperature. The reaction mixture was then diluted with ethyl acetate (0.10 M) and washed 2× with water, 1× with brine and dried over magnesium sulfate. The solvent was then removed in vacuo and the crude product was then purified by silica gel column chromatography to obtain protected form of Compound 18, 3-(4-BOC-amidinophenyl)-5-(4-(2-methoxy-carbonyl-2-N-ethyl-sulfonylaminoethyl)phenoxylmethyl-2-oxazolidinone which was carried onto the next step.

4) Deprotection of Protected Form of Compound 18 to Form Compound 18; 3-(4-Amidinophenyl)-5-(4-(2-carboxy-2-N-ethylsulfonylaminoethyl)phenoxy)methyl-2-oxazolidinone, FIG. 14

Treatment of the protected form of Compound 18, 3-(4-BOC-amidinophenyl)-5-(4-(2-methoxy-carbonyl-2-N-ethylsulfonylaminoethyl)phenoxylmethyl-2-oxazolidinone (1.0 equivalents; synthesized as described above), with 4 ml 2N NaOH for 4 hours at room temperature. The mixture was then followed with 40 ml 2N HCl-solution in dioxane added dropwise at 0° C. to 25° C. for 3 hours. The reaction mixture was then quenched with sodium bicarbonate (5 equivalents)

and then diluted with ethyl acetate (0.10 M) and washed 2× with water, 1× with brine and dried over magnesium sulfate. The solvent was then removed in vacuo and the crude product was then purified by silica gel column chromatography to obtain Compound 18: 3-(4-amidinophenyl)-5-(4-(2-carboxy-2-N-ethylsulfonylaminoethyl)phenoxy)methyl-2-oxazolidinone; m.p. 212° C. (d).

The foregoing written specification is considered to be sufficient to enable one skilled in the art to practice the invention. Indeed, various modifications of the invention in addition to those shown and described herein will become apparent to those skilled in the art from the foregoing description and fall within the scope of the appended claims.

What is claimed is:

1. A method for inhibiting $\alpha_v\beta_5$ mediated angiogenesis in a tissue comprising administering to said tissue a composition comprising an angiogenesis-inhibiting amount of an $\alpha_v\beta_5$ antagonist, wherein said antagonist is a matrix metalloproteinase polypeptide consisting of: SEQ ID NO 11, 12, 13, 14, 15, 16, 17, 18, 19, 20, 21 or 22.

2. The method of claim 1 wherein said tissue is human tissue.

3. The method of claim 2 wherein said tissue is inflamed and said angiogenesis is inflamed tissue angiogenesis.

4. The method of claim 1 wherein said tissue is arthritic.

5. The method of claim 4 wherein said arthritic tissue is present in a mammal with rheumatoid arthritis.

6. The method of claim 1 wherein said tissue is the retinal tissue and said angiogenesis is retinal angiogenesis.

7. The method of claim 6 wherein said retinal tissue is in a patient with diabetic retinopathy or macular degeneration.

8. The method of claim 1 wherein said tissue is a solid tumor or a solid tumor metastasis and said angiogenesis is tumor angiogenesis.

9. The method of claim 8 wherein said tissue is a carcinoma.

10. The method of claim 8 wherein said solid tumor is a tumor of lung, pancreas, breast, colon, larynx or ovary.

11. The method of claim 8 wherein said administering is conducted in conjunction with chemotherapy.

12. The method of claim 1 wherein said administering comprises intravenous, transdermal, intrasynovial, intramuscular, or oral administration.

13. The method of claim 1 wherein said angiogenesis-inhibiting amount is from about 0.1 mg/kg to about 300 mg/kg.

14. The method of claim 1 wherein said therapeutically effective amount is from about 0.1 mg/kg to about 300 mg/kg.

15. The method of claim 1 wherein said administering comprises a single dose intravenously.

16. The method of claim 1 wherein said administering comprises one or more dose administrations daily for one or more days.

17. The method of claim 1 wherein said angiogenesis is present in a patient having an eye disease selected from the group of eye diseases consisting of diabetic retinopathy, age-related macular degeneration, presumed ocular histoplasmosis, retinopathy of prematurity and neovascular glaucoma.

18. The method of claim 1 wherein said angiogenesis is present in a patient having a corneal neovascular disorder selected from the group of disorders consisting of corneal transplantation, herpetic keratitis, luetic keratitis, pterygium and neovascular pannus associated with contact lens use.

19. The method of claim 1 wherein said angiogenesis is induced by a cytokine.

20. The method of claim 19 wherein said cytokine is selected from the group consisting of vascular endothelial growth factor, transforming growth factor-α and epidermal growth factor.

21. The method of claim 19 wherein said cytokine is vascular endothelial growth factor and said angiogenesis is selected from the group consisting of retinal angiogenesis, corneal angiogenesis, tumor angiogenesis and inflamed tissue angiogenesis.

22. A method for inhibiting $\alpha_v\beta_5$ mediated angiogenesis in a tissue comprising administering to said tissue a composition comprising an angiogenesis-inhibiting amount of an $\alpha_v\beta_5$ antagonist, wherein said antagonist is an organic compound selected from the group consisting of compounds represented by the following structures:

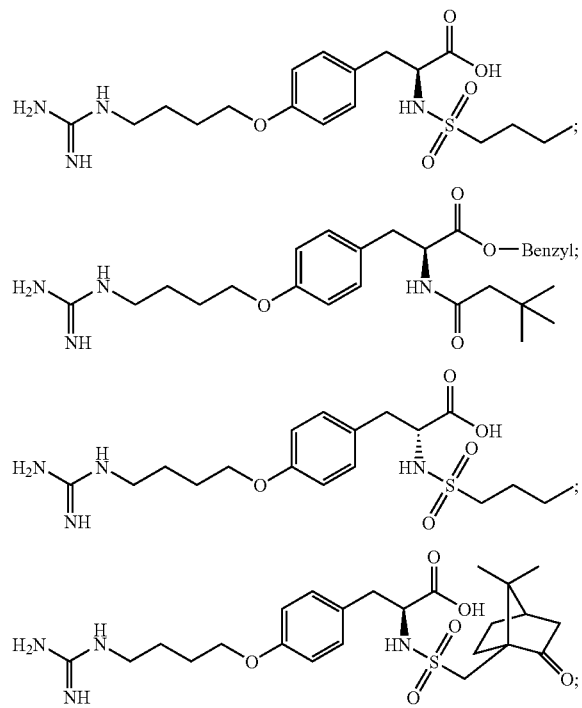

-continued

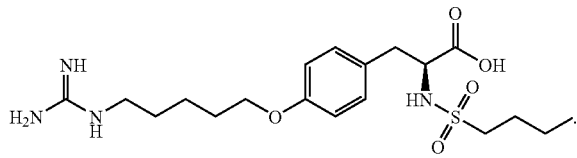

23. The method of claim 22 wherein said tissue is human tissue.

24. The method of claim 23 wherein said tissue is inflamed and said angiogenesis is inflamed tissue angiogenesis.

25. The method of claim 22 wherein said tissue is arthritic.

26. The method of claim 25 wherein said arthritic tissue is present in a mammal with rheumatoid arthritis.

27. The method of claim 22 wherein said tissue is the retinal tissue and said angiogenesis is retinal angiogenesis.

28. The method of claim 27 wherein said retinal tissue is in a patient with diabetic retinopathy or macular degeneration.

29. The method of claim 22 wherein said tissue is a solid tumor or a solid tumor metastasis and said angiogenesis is tumor angiogenesis.

30. The method of claim 29 wherein said tissue is a carcinoma.

31. The method of claim 29 wherein said solid tumor is a tumor of lung, pancreas, breast, colon, larynx or ovary.

32. The method of claim 29 wherein said administering is conducted in conjunction with chemotherapy.

33. The method of claim 22 wherein said administering comprises intravenous, transdermal, intrasynovial, intramuscular, or oral administration.

34. The method of claim 22 wherein said angiogenesis-inhibiting amount is from about 0.1 mg/kg to about 300 mg/kg.

35. The method of claim 22 wherein said therapeutically effective amount is from about 0.1 mg/kg to about 300 mg/kg.

36. The method of claim 22 wherein said administering comprises a single dose intravenously.

37. The method of claim 22 wherein said administering comprises one or more dose administrations daily for one or more days.

38. The method of claim 22 wherein said angiogenesis is present in a patient having an eye disease selected from the group of eye diseases consisting of diabetic retinopathy, age-related macular degeneration, presumed ocular histoplasmosis, retinopathy of prematurity and neovascular glaucoma.

39. The method of claim 22 wherein said angiogenesis is present in a patient having a corneal neovascular disorder selected from the group of disorders consisting of corneal transplantation, herpetic keratitis, luetic keratitis, pterygium and neovascular pannus associated with contact lens use.

40. The method of claim 22 wherein said angiogenesis is induced by a cytokine.

41. The method of claim 40 wherein said cytokine is selected from the group consisting of vascular endothelial growth factor, transforming growth factor-α and epidermal growth factor.

42. The method of claim 40 wherein said cytokine is vascular endothelial growth factor and said angiogenesis is selected from the group consisting of retinal angiogenesis, corneal angiogenesis, tumor angiogenesis and inflamed tissue angiogenesis.

* * * * *

UNITED STATES PATENT AND TRADEMARK OFFICE
CERTIFICATE OF CORRECTION

| | | |
|---|---|---|
| PATENT NO. | : 7,053,041 B1 | Page 1 of 1 |
| APPLICATION NO. | : 09/194552 | |
| DATED | : May 30, 2006 | |
| INVENTOR(S) | : Peter C. Brooks, David A. Cheresh and Martin Friedlander | |

It is certified that error appears in the above-identified patent and that said Letters Patent is hereby corrected as shown below:

Column 1, line 16, should read:

--This invention was made with government support under Contract Nos. CA50286, CA45726, HL54444, T32 A107244-11 and F32 CA72192 by the National Institutes of Health. The Government has certain rights in the invention.--

Signed and Sealed this

Eighteenth Day of December, 2007

JON W. DUDAS
*Director of the United States Patent and Trademark Office*

SEQUENCE LISTING

```
<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (1)..(5)
<223> OTHER INFORMATION: BOC signifies the N-terminal protecting group
      butyloxycarbonyl; OMe signifies a C-terminal
      methyl ester; arginine in the first position.
<220> FEATURE:
<221> NAME/KEY: PEPTIDE
<222> LOCATION: (1)..(5)
<223> OTHER INFORMATION: OMe signifies the C-terminal protecting group
      methyl ester.
<220> FEATURE:
<221> NAME/KEY: PEPTIDE
<222> LOCATION: (1)..(5)
<223> OTHER INFORMATION: A prefix "D" in D-phe signifies that the
      phenylalanine in position 4 is a D-amino acid.

<400> SEQUENCE: 1

Arg Gly Asp Phe Val
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (1)..(5)
<223> OTHER INFORMATION: BOC signifies the N-terminal blocking group
      tertbutyloxycarbonyl.
<220> FEATURE:
<221> NAME/KEY: PEPTIDE
<222> LOCATION: (1)..(5)
<223> OTHER INFORMATION: OH signifies a free C-terminal carboxylic acid.
<220> FEATURE:
<221> NAME/KEY: PEPTIDE
<222> LOCATION: (1)..(5)
<223> OTHER INFORMATION: A prefix "D" in D-Phe signifies that the
      phenylalanine in position 4 is a D-amino acid.

<400> SEQUENCE: 2

Arg Gly Asp Phe Val
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
```

```
<222> LOCATION: (1)..(5)
<223> OTHER INFORMATION: H signifies a free N-terminal amine.
<220> FEATURE:
<221> NAME/KEY: PEPTIDE
<222> LOCATION: (1)..(5)
<223> OTHER INFORMATION: OH signifies a free C-terminal carboxylic acid.
<220> FEATURE:
<221> NAME/KEY: PEPTIDE
<222> LOCATION: (1)..(5)
<223> OTHER INFORMATION: A prefix "D" in D-phe at position 4, signifies
      that the phenylalanine is a D-amino acid.

<400> SEQUENCE: 3

Arg Gly Asp Phe Val
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: PEPTIDE
<222> LOCATION: (1)..(5)
<223> OTHER INFORMATION: Phe is a D-amino acid.

<400> SEQUENCE: 4

Arg Gly Asp Phe Val
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: PEPTIDE
<222> LOCATION: (1)..(5)
<223> OTHER INFORMATION: Phe is a D-amino acid.

<400> SEQUENCE: 5

Arg Ala Asp Phe Val
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: PEPTIDE
<222> LOCATION: (1)..(6)
<223> OTHER INFORMATION: Arg is a D-amino acid.

<400> SEQUENCE: 6

Gly Arg Gly Asp Phe Val
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: PEPTIDE
<222> LOCATION: (1)..(5)
<223> OTHER INFORMATION: Val is a D-amino acid.
```

-continued

<400> SEQUENCE: 7

Arg Gly Asp Phe Val
 1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Peptide

<400> SEQUENCE: 8

Tyr Thr Ala Glu Cys Lys Pro Gln Val Thr Arg Gly Asp Val Phe
 1               5                  10                  15

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (1)..(6)
<223> OTHER INFORMATION: N-methylated valine.
<220> FEATURE:
<221> NAME/KEY: PEPTIDE
<222> LOCATION: (1)..(6)
<223> OTHER INFORMATION: Phe is a D-amino acid.

<400> SEQUENCE: 9

Arg Gly Asp Phe Asn Val
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (1)..(5)
<223> OTHER INFORMATION: Phe is a D-amino acid.
<220> FEATURE:
<221> NAME/KEY: PEPTIDE
<222> LOCATION: (5)..(5)
<223> OTHER INFORMATION: N-methylated valine

<400> SEQUENCE: 10

Arg Gly Glu Phe Val
 1               5

<210> SEQ ID NO 11
<211> LENGTH: 222
<212> TYPE: PRT
<213> ORGANISM: Homo sapiens

<400> SEQUENCE: 11

Lys Gly Ile Gln Glu Leu Tyr Gly Ala Ser Pro Asp Ile Asp Leu Gly
 1               5                  10                  15

Thr Gly Pro Thr Pro Thr Leu Gly Pro Val Thr Pro Glu Ile Cys Lys
                 20                  25                  30

Gln Asp Ile Val Phe Asp Gly Ile Ala Gln Ile Arg Gly Glu Ile Phe
             35                  40                  45

Phe Phe Lys Asp Arg Phe Ile Trp Arg Thr Val Thr Pro Arg Asp Lys

```
            50                  55                  60
Pro Met Gly Pro Leu Leu Val Ala Thr Phe Trp Pro Glu Leu Pro Glu
65                  70                  75                  80

Lys Ile Asp Ala Val Tyr Glu Ala Pro Gln Glu Glu Lys Ala Val Phe
                85                  90                  95

Phe Ala Gly Asn Glu Tyr Trp Ile Tyr Ser Ala Ser Thr Leu Glu Arg
            100                 105                 110

Gly Tyr Pro Lys Pro Leu Thr Ser Leu Gly Leu Pro Pro Asp Val Gln
        115                 120                 125

Arg Val Asp Ala Ala Phe Asn Trp Ser Lys Asn Lys Thr Tyr Ile
130                 135                 140

Phe Ala Gly Asp Lys Phe Trp Arg Tyr Asn Glu Val Lys Lys Met
145                 150                 155                 160

Asp Pro Gly Phe Pro Lys Leu Ile Ala Asp Ala Trp Asn Ala Ile Pro
                165                 170                 175

Asp Asn Leu Asp Ala Val Val Asp Leu Gln Gly Gly His Ser Tyr
            180                 185                 190

Phe Phe Lys Gly Ala Tyr Tyr Leu Lys Leu Glu Asn Gln Ser Leu Lys
        195                 200                 205

Ser Val Lys Phe Gly Ser Ile Lys Ser Asp Trp Leu Gly Cys
    210                 215                 220

<210> SEQ ID NO 12
<211> LENGTH: 193
<212> TYPE: PRT
<213> ORGANISM: Homo sapiens

<400> SEQUENCE: 12

Ile Cys Lys Gln Asp Ile Val Phe Asp Gly Ile Ala Gln Ile Arg Gly
1               5                   10                  15

Glu Ile Phe Phe Phe Lys Asp Arg Phe Ile Trp Arg Thr Val Thr Pro
            20                  25                  30

Arg Asp Lys Pro Met Gly Pro Leu Leu Val Ala Thr Phe Trp Pro Glu
        35                  40                  45

Leu Pro Glu Lys Ile Asp Ala Val Tyr Glu Ala Pro Gln Glu Glu Lys
    50                  55                  60

Ala Val Phe Phe Ala Gly Asn Glu Tyr Trp Ile Tyr Ser Ala Ser Thr
65                  70                  75                  80

Leu Glu Arg Gly Tyr Pro Lys Pro Leu Thr Ser Leu Gly Leu Pro Pro
                85                  90                  95

Asp Val Gln Arg Val Asp Ala Ala Phe Asn Trp Ser Lys Asn Lys Lys
            100                 105                 110

Thr Tyr Ile Phe Ala Gly Asp Lys Phe Trp Arg Tyr Asn Glu Val Lys
        115                 120                 125

Lys Lys Met Asp Pro Gly Phe Pro Lys Leu Ile Ala Asp Ala Trp Asn
130                 135                 140

Ala Ile Pro Asp Asn Leu Asp Ala Val Val Asp Leu Gln Gly Gly Gly
145                 150                 155                 160

His Ser Tyr Phe Phe Lys Gly Ala Tyr Tyr Leu Lys Leu Glu Asn Gln
                165                 170                 175

Ser Leu Lys Ser Val Lys Phe Gly Ser Ile Lys Ser Asp Trp Leu Gly
            180                 185                 190

Cys
```

-continued

<210> SEQ ID NO 13
<211> LENGTH: 74
<212> TYPE: PRT
<213> ORGANISM: Homo sapiens

<400> SEQUENCE: 13

```
Ile Cys Lys Gln Asp Ile Val Phe Asp Gly Ile Ala Gln Ile Arg Gly
 1               5                  10                  15

Glu Ile Phe Phe Phe Lys Asp Arg Phe Ile Trp Arg Thr Val Thr Pro
                20                  25                  30

Arg Asp Lys Pro Met Gly Pro Leu Leu Val Ala Thr Phe Trp Pro Glu
            35                  40                  45

Leu Pro Glu Lys Ile Asp Ala Val Tyr Glu Ala Pro Gln Glu Glu Lys
        50                  55                  60

Ala Val Phe Phe Ala Gly Asn Glu Tyr Trp
    65                  70
```

<210> SEQ ID NO 14
<211> LENGTH: 108
<212> TYPE: PRT
<213> ORGANISM: Homo sapiens

<400> SEQUENCE: 14

```
Ile Cys Lys Gln Asp Ile Val Phe Asp Gly Ile Ala Gln Ile Arg Gly
 1               5                  10                  15

Glu Ile Phe Phe Phe Lys Asp Arg Phe Ile Trp Arg Thr Val Thr Pro
                20                  25                  30

Arg Asp Lys Pro Met Gly Pro Leu Leu Val Ala Thr Phe Trp Pro Glu
            35                  40                  45

Leu Pro Glu Lys Ile Asp Ala Val Tyr Glu Ala Pro Gln Glu Glu Lys
        50                  55                  60

Ala Val Phe Phe Ala Gly Asn Glu Tyr Trp Ile Tyr Ser Ala Ser Thr
    65                  70                  75                  80

Leu Glu Arg Gly Tyr Pro Lys Pro Leu Thr Ser Leu Gly Leu Pro Pro
                85                  90                  95

Asp Val Gln Arg Val Asp Ala Ala Phe Asn Trp Ser
            100                 105
```

<210> SEQ ID NO 15
<211> LENGTH: 122
<212> TYPE: PRT
<213> ORGANISM: Homo sapiens

<400> SEQUENCE: 15

```
Glu Tyr Trp Ile Tyr Ser Ala Ser Thr Leu Glu Arg Gly Tyr Pro Lys
 1               5                  10                  15

Pro Leu Thr Ser Leu Gly Leu Pro Pro Asp Val Gln Arg Val Asp Ala
                20                  25                  30

Ala Phe Asn Trp Ser Lys Asn Lys Lys Thr Tyr Ile Phe Ala Gly Asp
            35                  40                  45

Lys Phe Trp Arg Tyr Asn Glu Val Lys Lys Met Asp Pro Gly Phe
        50                  55                  60

Pro Lys Leu Ile Ala Asp Ala Trp Asn Ala Ile Pro Asp Asn Leu Asp
    65                  70                  75                  80

Ala Val Val Asp Leu Gln Gly Gly Gly His Ser Tyr Phe Phe Lys Gly
                85                  90                  95

Ala Tyr Tyr Leu Lys Leu Glu Asn Gln Ser Leu Lys Ser Val Lys Phe
            100                 105                 110
```

```
Gly Ser Ile Lys Ser Asp Trp Leu Gly Cys
        115                 120
```

<210> SEQ ID NO 16
<211> LENGTH: 89
<212> TYPE: PRT
<213> ORGANISM: Homo sapiens

<400> SEQUENCE: 16

```
Phe Asn Trp Ser Lys Asn Lys Thr Tyr Ile Phe Ala Gly Asp Lys
 1               5                  10                  15

Phe Trp Arg Tyr Asn Glu Val Lys Lys Met Asp Pro Gly Phe Pro
            20                  25                  30

Lys Leu Ile Ala Asp Ala Trp Asn Ala Ile Pro Asp Asn Leu Asp Ala
        35                  40                  45

Val Val Asp Leu Gln Gly Gly His Ser Tyr Phe Phe Lys Gly Ala
    50                  55                  60

Tyr Tyr Leu Lys Leu Glu Asn Gln Ser Leu Lys Ser Val Lys Phe Gly
 65                  70                  75                  80

Ser Ile Lys Ser Asp Trp Leu Gly Cys
                85
```

<210> SEQ ID NO 17
<211> LENGTH: 228
<212> TYPE: PRT
<213> ORGANISM: Gallus gallus

<400> SEQUENCE: 17

```
Lys Gly Ile Gln Glu Leu Tyr Glu Val Ser Pro Asp Val Glu Pro Gly
 1               5                  10                  15

Pro Gly Pro Gly Pro Gly Pro Gly Pro Arg Pro Thr Leu Gly Pro Val
            20                  25                  30

Thr Pro Glu Leu Cys Lys His Asp Ile Val Phe Asp Gly Val Ala Gln
        35                  40                  45

Ile Arg Gly Glu Ile Phe Phe Phe Lys Asp Arg Phe Met Trp Arg Thr
    50                  55                  60

Val Asn Pro Arg Gly Lys Pro Thr Gly Pro Leu Leu Val Ala Thr Phe
 65                  70                  75                  80

Trp Pro Asp Leu Pro Glu Lys Ile Asp Ala Val Tyr Glu Ser Pro Gln
                85                  90                  95

Asp Glu Lys Ala Val Phe Phe Ala Gly Asn Glu Tyr Trp Val Tyr Thr
            100                 105                 110

Ala Ser Asn Leu Asp Arg Gly Tyr Pro Lys Lys Leu Thr Ser Leu Gly
        115                 120                 125

Leu Pro Pro Asp Val Gln Arg Ile Asp Ala Ala Phe Asn Trp Gly Arg
    130                 135                 140

Asn Lys Lys Thr Tyr Ile Phe Ser Gly Asp Arg Tyr Trp Lys Tyr Asn
145                 150                 155                 160

Glu Glu Lys Lys Lys Met Glu Leu Ala Thr Pro Lys Phe Ile Ala Asp
                165                 170                 175

Ser Trp Asn Gly Val Pro Asp Asn Leu Asp Ala Val Leu Gly Leu Thr
            180                 185                 190

Asp Ser Gly Tyr Thr Tyr Phe Phe Lys Asp Gln Tyr Tyr Leu Gln Met
        195                 200                 205

Glu Asp Lys Ser Leu Lys Ile Val Lys Ile Gly Lys Ile Ser Ser Asp
    210                 215                 220
```

```
Trp Leu Gly Cys
225

<210> SEQ ID NO 18
<211> LENGTH: 193
<212> TYPE: PRT
<213> ORGANISM: Gallus gallus

<400> SEQUENCE: 18

Leu Cys Lys His Asp Ile Val Phe Asp Gly Val Ala Gln Ile Arg Gly
  1               5                  10                  15

Glu Ile Phe Phe Phe Lys Asp Arg Phe Met Trp Arg Thr Val Asn Pro
             20                  25                  30

Arg Gly Lys Pro Thr Gly Pro Leu Leu Val Ala Thr Phe Trp Pro Asp
         35                  40                  45

Leu Pro Glu Lys Ile Asp Ala Val Tyr Glu Ser Pro Gln Asp Glu Lys
     50                  55                  60

Ala Val Phe Phe Ala Gly Asn Glu Tyr Trp Val Tyr Thr Ala Ser Asn
 65                  70                  75                  80

Leu Asp Arg Gly Tyr Pro Lys Lys Leu Thr Ser Leu Gly Leu Pro Pro
                 85                  90                  95

Asp Val Gln Arg Ile Asp Ala Ala Phe Asn Trp Gly Arg Asn Lys Lys
            100                 105                 110

Thr Tyr Ile Phe Ser Gly Asp Arg Tyr Trp Lys Tyr Asn Glu Glu Lys
        115                 120                 125

Lys Lys Met Glu Leu Ala Thr Pro Lys Phe Ile Ala Asp Ser Trp Asn
130                 135                 140

Gly Val Pro Asp Asn Leu Asp Ala Val Leu Gly Leu Thr Asp Ser Gly
145                 150                 155                 160

Tyr Thr Tyr Phe Phe Lys Asp Gln Tyr Tyr Leu Gln Met Glu Asp Lys
                165                 170                 175

Ser Leu Lys Ile Val Lys Ile Gly Lys Ile Ser Ser Asp Trp Leu Gly
            180                 185                 190

Cys

<210> SEQ ID NO 19
<211> LENGTH: 74
<212> TYPE: PRT
<213> ORGANISM: Gallus gallus

<400> SEQUENCE: 19

Leu Cys Lys His Asp Ile Val Phe Asp Gly Val Ala Gln Ile Arg Gly
  1               5                  10                  15

Glu Ile Phe Phe Phe Lys Asp Arg Phe Met Trp Arg Thr Val Asn Pro
             20                  25                  30

Arg Gly Lys Pro Thr Gly Pro Leu Leu Val Ala Thr Phe Trp Pro Asp
         35                  40                  45

Leu Pro Glu Lys Ile Asp Ala Val Tyr Glu Ser Pro Gln Asp Glu Lys
     50                  55                  60

Ala Val Phe Phe Ala Gly Asn Glu Tyr Trp
 65                  70

<210> SEQ ID NO 20
<211> LENGTH: 108
<212> TYPE: PRT
<213> ORGANISM: Gallus gallus
```

-continued

```
<400> SEQUENCE: 20

Leu Cys Lys His Asp Ile Val Phe Asp Gly Val Ala Gln Ile Arg Gly
  1               5                  10                  15

Glu Ile Phe Phe Phe Lys Asp Arg Phe Met Trp Arg Thr Val Asn Pro
             20                  25                  30

Arg Gly Lys Pro Thr Gly Pro Leu Leu Val Ala Thr Phe Trp Pro Asp
         35                  40                  45

Leu Pro Glu Lys Ile Asp Ala Val Tyr Glu Ser Pro Gln Asp Glu Lys
     50                  55                  60

Ala Val Phe Phe Ala Gly Asn Glu Tyr Trp Val Tyr Thr Ala Ser Asn
 65                  70                  75                  80

Leu Asp Arg Gly Tyr Pro Lys Lys Leu Thr Ser Leu Gly Leu Pro Pro
                 85                  90                  95

Asp Val Gln Arg Ile Asp Ala Ala Phe Asn Trp Gly
            100                 105

<210> SEQ ID NO 21
<211> LENGTH: 122
<212> TYPE: PRT
<213> ORGANISM: Gallus gallus

<400> SEQUENCE: 21

Glu Tyr Trp Val Tyr Thr Ala Ser Asn Leu Asp Arg Gly Tyr Pro Lys
  1               5                  10                  15

Lys Leu Thr Ser Leu Gly Leu Pro Pro Asp Val Gln Arg Ile Asp Ala
             20                  25                  30

Ala Phe Asn Trp Gly Arg Asn Lys Lys Thr Tyr Ile Phe Ser Gly Asp
         35                  40                  45

Arg Tyr Trp Lys Tyr Asn Glu Glu Lys Lys Lys Met Glu Leu Ala Thr
     50                  55                  60

Pro Lys Phe Ile Ala Asp Ser Trp Asn Gly Val Pro Asp Asn Leu Asp
 65                  70                  75                  80

Ala Val Leu Gly Leu Thr Asp Ser Gly Tyr Thr Tyr Phe Phe Lys Asp
                 85                  90                  95

Gln Tyr Tyr Leu Gln Met Glu Asp Lys Ser Leu Lys Ile Val Lys Ile
            100                 105                 110

Gly Lys Ile Ser Ser Asp Trp Leu Gly Cys
        115                 120

<210> SEQ ID NO 22
<211> LENGTH: 89
<212> TYPE: PRT
<213> ORGANISM: Gallus gallus

<400> SEQUENCE: 22

Phe Asn Trp Gly Arg Asn Lys Lys Thr Tyr Ile Phe Ser Gly Asp Arg
  1               5                  10                  15

Tyr Trp Lys Tyr Asn Glu Glu Lys Lys Lys Met Glu Leu Ala Thr Pro
             20                  25                  30

Lys Phe Ile Ala Asp Ser Trp Asn Gly Val Pro Asp Asn Leu Asp Ala
         35                  40                  45

Val Leu Gly Leu Thr Asp Ser Gly Tyr Thr Tyr Phe Phe Lys Asp Gln
     50                  55                  60

Tyr Tyr Leu Gln Met Glu Asp Lys Ser Leu Lys Ile Val Lys Ile Gly
 65                  70                  75                  80

Lys Ile Ser Ser Asp Trp Leu Gly Cys
```

-continued

85

<210> SEQ ID NO 23
<211> LENGTH: 2123
<212> TYPE: DNA
<213> ORGANISM: Gallus gallus
<220> FEATURE:
<221> NAME/KEY: CDS
<222> LOCATION: (132)..(2123)

<400> SEQUENCE: 23

```
aattccggca aaagagaaaa cggtgcagag agttaagatg tgcagataag caactagtgc      60
actgtgcagc caaagtaact gacagtcagt cagagaaatc ttttaaagag gattgcaaaa     120
atataggcag a atg aag act cac agt gtt ttt ggc ttc ttt ttt aaa gta     170
            Met Lys Thr His Ser Val Phe Gly Phe Phe Phe Lys Val
              1               5                  10 cta tta atc caa gtg tat ctt ttt aac aaa act tta gct gca ccg tca     218
Leu Leu Ile Gln Val Tyr Leu Phe Asn Lys Thr Leu Ala Ala Pro Ser
         15                  20                  25 cca atc att aag ttc cct gga gac agc act cca aaa aca gac aaa gag     266
Pro Ile Ile Lys Phe Pro Gly Asp Ser Thr Pro Lys Thr Asp Lys Glu
 30                  35                  40                  45 cta gca gtg caa tac ctg aat aaa tat tat gga tgc cca aaa gac aat     314
Leu Ala Val Gln Tyr Leu Asn Lys Tyr Tyr Gly Cys Pro Lys Asp Asn
                 50                  55                  60 tgc aac tta ttt gta ttg aaa gat act ttg aag aaa atg cag aaa ttt     362
Cys Asn Leu Phe Val Leu Lys Asp Thr Leu Lys Lys Met Gln Lys Phe
             65                  70                  75 ttt ggg ctg cct gaa aca gga gat ttg gat caa aac aca att gag aca     410
Phe Gly Leu Pro Glu Thr Gly Asp Leu Asp Gln Asn Thr Ile Glu Thr
         80                  85                  90 atg aag aaa ccc cgc tgt ggt aac ccc gat gtg gcc aat tac aac ttc     458
Met Lys Lys Pro Arg Cys Gly Asn Pro Asp Val Ala Asn Tyr Asn Phe
 95                 100                 105 ttt cca aga aag cca aaa tgg gaa aag aat cat ata aca tac agg att     506
Phe Pro Arg Lys Pro Lys Trp Glu Lys Asn His Ile Thr Tyr Arg Ile
110                 115                 120                 125 ata ggc tat acc ccg gat ttg gat cct gag aca gta gat gat gcc ttt     554
Ile Gly Tyr Thr Pro Asp Leu Asp Pro Glu Thr Val Asp Asp Ala Phe
                130                 135                 140 gcc cga gcc ttt aaa gtc tgg agt gat gtc acg cca ctg aga ttt aac     602
Ala Arg Ala Phe Lys Val Trp Ser Asp Val Thr Pro Leu Arg Phe Asn
            145                 150                 155 cga ata aat gat gga gag gca gac att atg att aat ttt ggc cga tgg     650
Arg Ile Asn Asp Gly Glu Ala Asp Ile Met Ile Asn Phe Gly Arg Trp
        160                 165                 170 gaa cat ggt gat ggc tat cca ttt gat ggc aaa gat ggt ctc ctg gct     698
Glu His Gly Asp Gly Tyr Pro Phe Asp Gly Lys Asp Gly Leu Leu Ala
    175                 180                 185 cac gcc ttt gca ccg ggg cca gga att gga gga gac tcc cat ttt gat     746
His Ala Phe Ala Pro Gly Pro Gly Ile Gly Gly Asp Ser His Phe Asp
190                 195                 200                 205 gat gat gaa ctg tgg act ctt gga gaa ggg caa gtg gtt aga gta aag     794
Asp Asp Glu Leu Trp Thr Leu Gly Glu Gly Gln Val Val Arg Val Lys
                210                 215                 220 tat gga aat gca gat ggt gaa tac tgc aaa ttt ccc ttc tgg tca aat     842
Tyr Gly Asn Ala Asp Gly Glu Tyr Cys Lys Phe Pro Phe Trp Ser Asn
            225                 230                 235 ggt aag gaa tac aac agc tgc aca gat gca gga cgt aat gat gga ttc     890
Gly Lys Glu Tyr Asn Ser Cys Thr Asp Ala Gly Arg Asn Asp Gly Phe
```

-continued

```
                 240                 245                  250
ctc tgg tgt tcc aca acc aaa gac ttt gat gca gat ggc aaa tat ggc      938
Leu Trp Cys Ser Thr Thr Lys Asp Phe Asp Ala Asp Gly Lys Tyr Gly
    255                 260                 265 ttt tgt ccc cat gag tca ctt ttt aca atg ggt ggc aat ggt gat gga      986
Phe Cys Pro His Glu Ser Leu Phe Thr Met Gly Gly Asn Gly Asp Gly
270                 275                 280                 285 cag ccc tgc aag ttt ccc ttt aaa ttt caa ggc cag tcc tat gac cag     1034
Gln Pro Cys Lys Phe Pro Phe Lys Phe Gln Gly Gln Ser Tyr Asp Gln
                290                 295                 300 tgt aca aca gaa ggc agg aca gat gga tac aga tgg tgt gga acc act     1082
Cys Thr Thr Glu Gly Arg Thr Asp Gly Tyr Arg Trp Cys Gly Thr Thr
305                 310                 315 gaa gac tat gat aga gat aag aaa tac gga ttc tgc cca gaa act gcc     1130
Glu Asp Tyr Asp Arg Asp Lys Lys Tyr Gly Phe Cys Pro Glu Thr Ala
320                 325                 330 atg tca aca gtt ggt gga aat tca gaa gga gct cct tgt gta ttc ccc     1178
Met Ser Thr Val Gly Gly Asn Ser Glu Gly Ala Pro Cys Val Phe Pro
    335                 340                 345 ttc atc ttc ctt ggg aat aaa tac gac tcc tgt aca agt gca ggt cgc     1226
Phe Ile Phe Leu Gly Asn Lys Tyr Asp Ser Cys Thr Ser Ala Gly Arg
350                 355                 360                 365 aat gat ggc aag ctg tgg tgt gct tct acc agc agc tat gat gat gac     1274
Asn Asp Gly Lys Leu Trp Cys Ala Ser Thr Ser Ser Tyr Asp Asp Asp
                370                 375                 380 cgc aag tgg ggc ttt tgt cca gat caa gga tac agt ctc ttc ttg gtt     1322
Arg Lys Trp Gly Phe Cys Pro Asp Gln Gly Tyr Ser Leu Phe Leu Val
            385                 390                 395 gct gcc cac gaa ttt ggc cat gcg atg gga tta gag cac tcc gag gac     1370
Ala Ala His Glu Phe Gly His Ala Met Gly Leu Glu His Ser Glu Asp
        400                 405                 410 cca gga gct ctc atg gcc ccg atc tac acc tac acc aag aac ttc cgc     1418
Pro Gly Ala Leu Met Ala Pro Ile Tyr Thr Tyr Thr Lys Asn Phe Arg
    415                 420                 425 ctt tct cag gat gac att aag ggg att cag gag cta tat gaa gta tca     1466
Leu Ser Gln Asp Asp Ile Lys Gly Ile Gln Glu Leu Tyr Glu Val Ser
430                 435                 440                 445 cct gat gtg gaa cct gga cca ggg cca gga cca ggg cca gga cca cgt     1514
Pro Asp Val Glu Pro Gly Pro Gly Pro Gly Pro Gly Pro Gly Pro Arg
                450                 455                 460 cct acc ctt gga cct gtc act cca gag ctc tgc aag cac gac att gta     1562
Pro Thr Leu Gly Pro Val Thr Pro Glu Leu Cys Lys His Asp Ile Val
            465                 470                 475 ttt gat gga gtt gca caa att aga gga gaa ata ttt ttc ttc aaa gac     1610
Phe Asp Gly Val Ala Gln Ile Arg Gly Glu Ile Phe Phe Phe Lys Asp
        480                 485                 490 aga ttc atg tgg agg act gta aac cct cga gga aaa ccc aca ggt cct     1658
Arg Phe Met Trp Arg Thr Val Asn Pro Arg Gly Lys Pro Thr Gly Pro
    495                 500                 505 ctt ctc gtt gct aca ttc tgg cct gat ctg cca gag aaa atc gat gct     1706
Leu Leu Val Ala Thr Phe Trp Pro Asp Leu Pro Glu Lys Ile Asp Ala
510                 515                 520                 525 gtc tac gag tcc cct cag gat gag aag gct gta ttt ttt gca gga aat     1754
Val Tyr Glu Ser Pro Gln Asp Glu Lys Ala Val Phe Phe Ala Gly Asn
                530                 535                 540 gag tac tgg gtt tat aca gcc agc aac ctg gat agg ggc tat cca aag     1802
Glu Tyr Trp Val Tyr Thr Ala Ser Asn Leu Asp Arg Gly Tyr Pro Lys
            545                 550                 555 aaa ctc acc agc ctg gga cta ccc cct gat gtg caa cgc att gat gca     1850
Lys Leu Thr Ser Leu Gly Leu Pro Pro Asp Val Gln Arg Ile Asp Ala
```

-continued

```
Lys Leu Thr Ser Leu Gly Leu Pro Pro Asp Val Gln Arg Ile Asp Ala
            560                 565                 570 gcc ttc aac tgg ggc aga aac aag aag aca tat att ttc tct gga gac      1898
Ala Phe Asn Trp Gly Arg Asn Lys Lys Thr Tyr Ile Phe Ser Gly Asp
        575                 580                 585 aga tac tgg aag tac aat gaa gaa aag aaa atg gag ctt gca acc          1946
Arg Tyr Trp Lys Tyr Asn Glu Glu Lys Lys Met Glu Leu Ala Thr
590                 595                 600                 605 cca aaa ttc att gcg gat tct tgg aat gga gtt cca gat aac ctc gat      1994
Pro Lys Phe Ile Ala Asp Ser Trp Asn Gly Val Pro Asp Asn Leu Asp
            610                 615                 620 gct gtc ctg ggt ctt act gac agc ggg tac acc tat ttt ttc aaa gac      2042
Ala Val Leu Gly Leu Thr Asp Ser Gly Tyr Thr Tyr Phe Phe Lys Asp
            625                 630                 635 cag tac tat cta caa atg gaa gac aag agt ttg aag att gtt aaa att      2090
Gln Tyr Tyr Leu Gln Met Glu Asp Lys Ser Leu Lys Ile Val Lys Ile
            640                 645                 650 ggc aag ata agt tct gac tgg ttg ggt tgc tga                          2123
Gly Lys Ile Ser Ser Asp Trp Leu Gly Cys
            655                 660
```

<210> SEQ ID NO 24
<211> LENGTH: 663
<212> TYPE: PRT
<213> ORGANISM: Gallus gallus

<400> SEQUENCE: 24

```
Met Lys Thr His Ser Val Phe Gly Phe Phe Lys Val Leu Leu Ile
1               5                   10                  15

Gln Val Tyr Leu Phe Asn Lys Thr Leu Ala Ala Pro Ser Pro Ile Ile
            20                  25                  30

Lys Phe Pro Gly Asp Ser Thr Pro Lys Thr Asp Lys Glu Leu Ala Val
        35                  40                  45

Gln Tyr Leu Asn Lys Tyr Tyr Gly Cys Pro Lys Asp Asn Cys Asn Leu
    50                  55                  60

Phe Val Leu Lys Asp Thr Leu Lys Lys Met Gln Lys Phe Phe Gly Leu
65                  70                  75                  80

Pro Glu Thr Gly Asp Leu Asp Gln Asn Thr Ile Glu Thr Met Lys Lys
                85                  90                  95

Pro Arg Cys Gly Asn Pro Asp Val Ala Asn Tyr Asn Phe Phe Pro Arg
            100                 105                 110

Lys Pro Lys Trp Glu Lys Asn His Ile Thr Tyr Arg Ile Ile Gly Tyr
        115                 120                 125

Thr Pro Asp Leu Asp Pro Glu Thr Val Asp Asp Ala Phe Ala Arg Ala
    130                 135                 140

Phe Lys Val Trp Ser Asp Val Thr Pro Leu Arg Phe Asn Arg Ile Asn
145                 150                 155                 160

Asp Gly Glu Ala Asp Ile Met Ile Asn Phe Gly Arg Trp Glu His Gly
                165                 170                 175

Asp Gly Tyr Pro Phe Asp Gly Lys Asp Gly Leu Leu Ala His Ala Phe
            180                 185                 190

Ala Pro Gly Pro Gly Ile Gly Gly Asp Ser His Phe Asp Asp Glu
        195                 200                 205

Leu Trp Thr Leu Gly Glu Gly Gln Val Val Arg Val Lys Tyr Gly Asn
    210                 215                 220

Ala Asp Gly Glu Tyr Cys Lys Phe Pro Phe Trp Phe Asn Gly Lys Glu
225                 230                 235                 240
```

-continued

```
Tyr Asn Ser Cys Thr Asp Ala Gly Arg Asn Asp Gly Phe Leu Trp Cys
                245                 250                 255
Ser Thr Thr Lys Asp Phe Asp Ala Asp Gly Lys Tyr Gly Phe Cys Pro
            260                 265                 270
His Glu Ser Leu Phe Thr Met Gly Asn Gly Asp Gly Gln Pro Cys
        275                 280                 285
Lys Phe Pro Phe Lys Phe Gln Gly Gln Ser Tyr Asp Gln Cys Thr Thr
    290                 295                 300
Glu Gly Arg Thr Asp Gly Tyr Arg Trp Cys Gly Thr Thr Glu Asp Tyr
305                 310                 315                 320
Asp Arg Asp Lys Lys Tyr Gly Phe Cys Pro Glu Thr Ala Met Ser Thr
                325                 330                 335
Val Gly Gly Asn Ser Glu Gly Ala Pro Cys Val Phe Pro Phe Ile Phe
            340                 345                 350
Leu Gly Asn Lys Tyr Asp Ser Cys Thr Ser Ala Gly Arg Asn Asp Gly
        355                 360                 365
Lys Leu Trp Cys Ala Ser Thr Ser Ser Tyr Asp Asp Asp Arg Lys Trp
    370                 375                 380
Gly Phe Cys Pro Asp Gln Gly Tyr Ser Leu Phe Leu Val Ala Ala His
385                 390                 395                 400
Glu Phe Gly His Ala Met Gly Leu Glu His Ser Glu Asp Pro Gly Ala
                405                 410                 415
Leu Met Ala Pro Ile Tyr Thr Tyr Thr Lys Asn Phe Arg Leu Ser Gln
            420                 425                 430
Asp Asp Ile Lys Gly Ile Gln Glu Leu Tyr Glu Val Ser Pro Asp Val
        435                 440                 445
Glu Pro Gly Pro Gly Pro Gly Pro Gly Pro Arg Pro Thr Leu
    450                 455                 460
Gly Pro Val Thr Pro Glu Leu Cys Lys His Asp Ile Val Phe Asp Gly
465                 470                 475                 480
Val Ala Gln Ile Arg Gly Glu Ile Phe Phe Phe Lys Asp Arg Phe Met
                485                 490                 495
Trp Arg Thr Val Asn Pro Arg Gly Lys Pro Thr Gly Pro Leu Leu Val
            500                 505                 510
Ala Thr Phe Trp Pro Asp Leu Pro Glu Lys Ile Asp Ala Val Tyr Glu
        515                 520                 525
Ser Pro Gln Asp Glu Lys Ala Val Phe Phe Ala Gly Asn Glu Tyr Trp
    530                 535                 540
Val Tyr Thr Ala Ser Asn Leu Asp Arg Gly Tyr Pro Lys Lys Leu Thr
545                 550                 555                 560
Ser Leu Gly Leu Pro Pro Asp Val Gln Arg Ile Asp Ala Ala Phe Asn
                565                 570                 575
Trp Gly Arg Asn Lys Lys Thr Tyr Ile Phe Ser Gly Asp Arg Tyr Trp
            580                 585                 590
Lys Tyr Asn Glu Glu Lys Lys Lys Met Glu Leu Ala Thr Pro Lys Phe
        595                 600                 605
Ile Ala Asp Ser Trp Asn Gly Val Pro Asp Asn Leu Asp Ala Val Leu
    610                 615                 620
Gly Leu Thr Asp Ser Gly Tyr Thr Tyr Phe Phe Lys Asp Gln Tyr Tyr
625                 630                 635                 640
Leu Gln Met Glu Asp Lys Ser Leu Lys Ile Val Lys Ile Gly Lys Ile
                645                 650                 655
```

-continued

```
Ser Ser Asp Trp Leu Gly Cys
            660

<210> SEQ ID NO 25
<211> LENGTH: 631
<212> TYPE: PRT
<213> ORGANISM: Homo sapiens

<400> SEQUENCE: 25

Ala Pro Ser Pro Ile Ile Lys Phe Pro Gly Asp Val Ala Pro Lys Thr
  1               5                  10                  15

Asp Lys Glu Leu Ala Val Gln Tyr Leu Asn Thr Phe Tyr Gly Cys Pro
             20                  25                  30

Lys Glu Ser Cys Asn Leu Phe Val Leu Lys Asp Thr Leu Lys Lys Met
         35                  40                  45

Gln Lys Phe Phe Gly Leu Pro Gln Thr Gly Asp Leu Asp Gln Asn Thr
     50                  55                  60

Ile Glu Thr Met Arg Lys Pro Arg Cys Gly Asn Pro Asp Val Ala Asn
 65                  70                  75                  80

Tyr Asn Phe Phe Pro Arg Lys Pro Lys Trp Asp Lys Asn Gln Ile Thr
                 85                  90                  95

Tyr Arg Ile Ile Gly Tyr Thr Pro Asp Leu Asp Pro Glu Thr Val Asp
            100                 105                 110

Asp Ala Phe Ala Arg Ala Phe Gln Val Trp Ser Asp Val Thr Pro Leu
        115                 120                 125

Arg Phe Ser Arg Ile His Asp Gly Glu Ala Asp Ile Met Ile Asn Phe
    130                 135                 140

Gly Arg Trp Glu His Gly Asp Gly Tyr Pro Phe Asp Gly Lys Asp Gly
145                 150                 155                 160

Leu Leu Ala His Ala Phe Ala Pro Gly Thr Gly Val Gly Gly Asp Ser
                165                 170                 175

His Phe Asp Asp Asp Glu Leu Trp Thr Leu Gly Glu Gly Gln Val Val
            180                 185                 190

Arg Val Lys Tyr Gly Asn Ala Asp Gly Glu Tyr Cys Lys Phe Pro Phe
        195                 200                 205

Leu Phe Asn Gly Lys Glu Tyr Asn Ser Cys Thr Asp Thr Gly Arg Ser
    210                 215                 220

Asp Gly Phe Leu Trp Cys Ser Thr Thr Tyr Asn Phe Glu Lys Asp Gly
225                 230                 235                 240

Lys Tyr Gly Phe Cys Pro His Glu Ala Leu Phe Thr Met Gly Gly Asn
                245                 250                 255

Ala Glu Gly Gln Pro Cys Lys Phe Pro Phe Arg Phe Gln Gly Thr Ser
            260                 265                 270

Tyr Asp Ser Cys Thr Thr Glu Gly Arg Thr Asp Gly Tyr Arg Trp Cys
        275                 280                 285

Gly Thr Thr Glu Asp Tyr Asp Arg Asp Lys Lys Tyr Gly Phe Cys Pro
    290                 295                 300

Glu Thr Ala Met Ser Thr Val Gly Gly Asn Ser Glu Gly Ala Pro Cys
305                 310                 315                 320

Val Phe Pro Phe Thr Phe Leu Gly Asn Lys Tyr Glu Ser Cys Thr Ser
                325                 330                 335

Ala Gly Arg Ser Asp Gly Lys Met Trp Cys Ala Thr Thr Ala Asn Tyr
            340                 345                 350

Asp Asp Asp Arg Lys Trp Gly Phe Cys Pro Asp Gln Gly Tyr Ser Leu
        355                 360                 365
```

Phe Leu Val Ala Ala His Glu Phe Gly His Ala Met Gly Leu Glu His
    370                 375                 380

Ser Gln Asp Pro Gly Ala Leu Met Ala Pro Ile Tyr Thr Tyr Thr Lys
385                 390                 395                 400

Asn Phe Arg Leu Ser Gln Asp Ile Lys Gly Ile Gln Glu Leu Tyr
                405                 410                 415

Gly Ala Ser Pro Asp Ile Asp Leu Gly Thr Gly Pro Thr Pro Thr Leu
                420                 425                 430

Gly Pro Val Thr Pro Glu Ile Cys Lys Gln Asp Ile Val Phe Asp Gly
                435                 440                 445

Ile Ala Gln Ile Arg Gly Glu Ile Phe Phe Lys Asp Arg Phe Ile
    450                 455                 460

Trp Arg Thr Val Thr Pro Arg Asp Lys Pro Met Gly Pro Leu Leu Val
465                 470                 475                 480

Ala Thr Phe Trp Pro Glu Leu Pro Glu Lys Ile Asp Ala Val Tyr Glu
                485                 490                 495

Ala Pro Gln Glu Glu Lys Ala Val Phe Phe Ala Gly Asn Glu Tyr Trp
                500                 505                 510

Ile Tyr Ser Ala Ser Thr Leu Glu Arg Gly Tyr Pro Lys Pro Leu Thr
    515                 520                 525

Ser Leu Gly Leu Pro Pro Asp Val Gln Arg Val Asp Ala Ala Phe Asn
    530                 535                 540

Trp Ser Lys Asn Lys Lys Thr Tyr Ile Phe Ala Gly Asp Lys Phe Trp
545                 550                 555                 560

Arg Tyr Asn Glu Val Lys Lys Met Asp Pro Gly Phe Pro Lys Leu
                565                 570                 575

Ile Ala Asp Ala Trp Asn Ala Ile Pro Asp Asn Leu Asp Ala Val Val
                580                 585                 590

Asp Leu Gln Gly Gly Gly His Ser Tyr Phe Phe Lys Gly Ala Tyr Tyr
    595                 600                 605

Leu Lys Leu Glu Asn Gln Ser Leu Lys Ser Val Lys Phe Gly Ser Ile
    610                 615                 620

Lys Ser Asp Trp Leu Gly Cys
625                 630

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
attgaattct tctacagttc a                                      21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 27
atgggatcca ctgcaaattt c                                      21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 28
gccggatcca tgaccagtgt a                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 29
gtgggatccc tgaagactat g                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 30
aggggatcct taagggatt c                                               21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 31
ctcggatcct ctgcaagcac g                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 32
ctcggatcct ctgcaagcac g                                              21

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 33
gcaggatccg agtgctgggt ttatac                                         26

<210> SEQ ID NO 34

```
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 34
gcagaattca actgtggcag aaacaag                                              27

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 35
gtagaattcc agcactcatt tcctgc                                               26

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 36
tctgaattct gccacagttg aagg                                                 24

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 37
attgaattct tctacagttc a                                                    21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 38
gatgaattct actgcaagtt                                                      20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 39
cactgaattc atctgcaaac a                                                    21

<210> SEQ ID NO 40
<211> LENGTH: 429
```

<212> TYPE: PRT
<213> ORGANISM: Artificial Sequence
<220> FEATURE:
<223> OTHER INFORMATION: Description of Artificial Sequence: Human MMP-2 fusion protein

<400> SEQUENCE: 40

```
Tyr Cys Lys Phe Pro Phe Leu Phe Asn Gly Lys Glu Tyr Asn Ser Cys
 1               5                  10                  15

Thr Asp Thr Gly Arg Ser Asp Gly Phe Leu Trp Cys Ser Thr Thr Tyr
            20                  25                  30

Asn Phe Glu Lys Asp Gly Lys Tyr Gly Phe Cys Pro His Glu Ala Leu
        35                  40                  45

Phe Thr Met Gly Gly Asn Ala Glu Gly Gln Pro Cys Lys Phe Pro Phe
    50                  55                  60

Arg Phe Gln Gly Thr Ser Tyr Asp Ser Cys Thr Thr Glu Gly Arg Thr
65                  70                  75                  80

Asp Gly Tyr Arg Trp Cys Gly Thr Thr Glu Asp Tyr Asp Arg Asp Lys
                85                  90                  95

Lys Tyr Gly Phe Cys Pro Glu Thr Ala Met Ser Thr Val Gly Gly Asn
            100                 105                 110

Ser Glu Gly Ala Pro Cys Val Phe Pro Phe Thr Phe Leu Gly Asn Lys
        115                 120                 125

Tyr Glu Ser Cys Thr Ser Ala Gly Arg Ser Asp Gly Lys Met Trp Cys
    130                 135                 140

Ala Thr Thr Ala Asn Tyr Asp Asp Asp Arg Lys Trp Gly Phe Cys Pro
145                 150                 155                 160

Asp Gln Gly Tyr Ser Leu Phe Leu Val Ala Ala His Glu Phe Gly His
                165                 170                 175

Ala Met Gly Leu Glu His Ser Gln Asp Pro Gly Ala Leu Met Ala Pro
            180                 185                 190

Ile Tyr Thr Tyr Thr Lys Asn Phe Arg Leu Ser Gln Asp Asp Ile Lys
        195                 200                 205

Gly Ile Gln Glu Leu Tyr Gly Ala Ser Pro Asp Ile Asp Leu Gly Thr
    210                 215                 220

Gly Pro Thr Pro Thr Leu Gly Pro Val Thr Pro Glu Ile Cys Lys Gln
225                 230                 235                 240

Asp Ile Val Phe Asp Gly Ile Ala Gln Ile Arg Gly Glu Ile Phe Phe
                245                 250                 255

Phe Lys Asp Arg Phe Ile Trp Arg Thr Val Thr Pro Arg Asp Lys Pro
            260                 265                 270

Met Gly Pro Leu Leu Val Ala Thr Phe Trp Pro Glu Leu Pro Glu Lys
        275                 280                 285

Ile Asp Ala Val Tyr Glu Ala Pro Gln Glu Glu Lys Ala Val Phe Phe
    290                 295                 300

Ala Gly Asn Glu Tyr Trp Ile Tyr Ser Ala Ser Thr Leu Glu Arg Gly
305                 310                 315                 320

Tyr Pro Lys Pro Leu Thr Ser Leu Gly Leu Pro Pro Asp Val Gln Arg
                325                 330                 335

Val Asp Ala Ala Phe Asn Trp Ser Lys Asn Lys Lys Thr Tyr Ile Phe
            340                 345                 350

Ala Gly Asp Lys Phe Trp Arg Tyr Asn Glu Val Lys Lys Lys Met Asp
        355                 360                 365

Pro Gly Phe Pro Lys Leu Ile Ala Asp Ala Trp Asn Ala Ile Pro Asp
    370                 375                 380
```

Asn Leu Asp Ala Val Val Asp Leu Gln Gly Gly Gly His Ser Tyr Phe
385                 390                 395                 400

Phe Lys Gly Ala Tyr Tyr Leu Lys Leu Glu Asn Gln Ser Leu Lys Ser
            405                 410                 415

Val Lys Phe Gly Ser Ile Lys Ser Asp Trp Leu Gly Cys
            420                 425

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (1)..(5)
<223> OTHER INFORMATION: Fmoc modified.
<220> FEATURE:
<221> NAME/KEY: PEPTIDE
<222> LOCATION: (1)..(5)
<223> OTHER INFORMATION: OButl modified at position 3.
<220> FEATURE:
<221> NAME/KEY: PEPTIDE
<222> LOCATION: (1)..(5)
<223> OTHER INFORMATION: Methylated valine at position 5.
<220> FEATURE:
<221> NAME/KEY: PEPTIDE
<222> LOCATION: (1)..(5)
<223> OTHER INFORMATION: Valine with a carboxy terminal ONa.

<400> SEQUENCE: 41

Arg Gly Asp Phe Val
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (1)..(5)
<223> OTHER INFORMATION: Fmoc modified
<220> FEATURE:
<221> NAME/KEY: PEPTIDE
<222> LOCATION: (1)..(5)
<223> OTHER INFORMATION: OButyl modified in position 3.
<220> FEATURE:
<221> NAME/KEY: PEPTIDE
<222> LOCATION: (1)..(5)
<223> OTHER INFORMATION: Methylated valine in position 5.
<220> FEATURE:
<221> NAME/KEY: PEPTIDE
<222> LOCATION: (1)..(5)
<223> OTHER INFORMATION: Valine with a hydroxyl group.

<400> SEQUENCE: 42

Arg Gly Asp Phe Val
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (1)..(5)
<223> OTHER INFORMATION: OButl modified at position 3.

```
<220> FEATURE:
<221> NAME/KEY: PEPTIDE
<222> LOCATION: (1)..(5)
<223> OTHER INFORMATION: Methylated valine at position 5.
<220> FEATURE:
<221> NAME/KEY: PEPTIDE
<222> LOCATION: (1)..(5)
<223> OTHER INFORMATION: Valine with a hydroxyl group.

<400> SEQUENCE: 43

Arg Gly Asp Phe Val
 1               5
```